US012357336B2

(12) United States Patent
Moungondo

(10) Patent No.: US 12,357,336 B2
(45) Date of Patent: Jul. 15, 2025

(54) MEDICAL INSTRUMENT FOR PERCUTANEOUS RELEASE PROCEDURES

(71) Applicant: SPIRECUT SA, Muttenz (CH)

(72) Inventor: Fabian Moungondo, Colfontaine (BE)

(73) Assignee: SPIRECUT SA, Muttenz (CH)

( * ) Notice: Subject to any disclaimer, the term of this patent is extended or adjusted under 35 U.S.C. 154(b) by 982 days.

(21) Appl. No.: 17/256,363

(22) PCT Filed: Jul. 1, 2019

(86) PCT No.: PCT/IB2019/055552
§ 371 (c)(1),
(2) Date: Dec. 28, 2020

(87) PCT Pub. No.: WO2020/003263
PCT Pub. Date: Jan. 2, 2020

(65) Prior Publication Data
US 2021/0369293 A1 Dec. 2, 2021

(30) Foreign Application Priority Data

Jun. 29, 2018 (EP) .................................... 18180894
Nov. 14, 2018 (EP) .................................... 18206119

(51) Int. Cl.
A61B 17/32 (2006.01)
A61B 17/00 (2006.01)
A61B 90/00 (2016.01)

(52) U.S. Cl.
CPC ............. A61B 17/320036 (2013.01); A61B 2017/00314 (2013.01); A61B 2017/00455 (2013.01);
(Continued)

(58) Field of Classification Search
CPC .... A61B 17/320036; A61B 17/320016; A61B 17/3209; A61B 17/32093; A61B 17/3211;
(Continued)

(56) References Cited

U.S. PATENT DOCUMENTS 4,955,894 A 9/1990 Herman
5,029,573 A * 7/1991 Chow ................ A61B 17/34
600/114

(Continued)

FOREIGN PATENT DOCUMENTS

CN 207654202 U 7/2018
KR 20130136333 A 12/2013
(Continued)

OTHER PUBLICATIONS

International Search Report; European Patent Office; International Application No. PCT/IB2019/055552; Aug. 16, 2019; 7 pages.
(Continued)

Primary Examiner — Brigid K Byrd
(74) Attorney, Agent, or Firm — Taft Stettinius & Hollister LLP

(57) ABSTRACT

A medical instrument for percutaneous release procedures, especially on upper or lower limbs, including percutaneous carpal tunnel release or percutaneous A1 pulley release. The medical instrument includes a handle portion to allow handling, orientation and manipulation of the medical instrument by a surgeon, and an elongated rod member secured to the handle portion and extending substantially within a defined plane. A first portion of the elongated rod member extends substantially along a first direction within the defined plane away from the handle portion, and a second portion of the elongated rod member is curved and/or bent within the defined plane. A free end of the elongated rod member, at a terminal end of the second portion, may be (Continued)

shaped as a beveled end including a beveled surface, which beveled end acts as a cutting device to sever tissue, and the beveled surface being inclined with respect to the defined plane.

35 Claims, 50 Drawing Sheets

(52) U.S. Cl.
 CPC .............. *A61B 2090/3925* (2016.02); *A61B 2090/3937* (2016.02)
(58) Field of Classification Search
 CPC ........ A61B 2017/320052; A61B 1/317; A61B 90/39; A61B 2017/00314; A61B 2017/00455; A61B 2090/3925; A61B 2090/3937; A61M 5/3286
 See application file for complete search history.

(56) References Cited

U.S. PATENT DOCUMENTS

| | | | |
|---|---|---|---|
| 5,222,977 A * | 6/1993 | Esser | A61B 17/06004 606/144 |
| 5,273,024 A | 12/1993 | Menon et al. | |
| 5,282,816 A * | 2/1994 | Miller | A61B 17/320036 606/167 |
| 5,411,510 A * | 5/1995 | Fugo | A61F 9/00754 606/166 |
| 5,507,800 A | 4/1996 | Strickland | |
| 5,769,865 A | 6/1998 | Kermode et al. | |
| 5,782,850 A | 7/1998 | Ro | |
| 5,827,311 A | 10/1998 | Berelsman et al. | |
| 5,908,433 A | 6/1999 | Eager et al. | |
| 6,019,774 A * | 2/2000 | Weiss | A61B 17/320036 606/167 |
| 8,603,124 B1 | 12/2013 | Hatch | |
| 8,608,765 B1 | 12/2013 | Jurbala | |
| 9,943,324 B2 | 4/2018 | Park | |
| 2007/0066887 A1 * | 3/2007 | Mire | A61B 90/39 600/424 |
| 2011/0306996 A1 * | 12/2011 | McCormack | A61B 17/320036 606/170 |
| 2012/0150208 A1 * | 6/2012 | Messmer | A61B 17/320016 606/167 |
| 2015/0080896 A1 * | 3/2015 | To | A61B 17/320016 606/79 |
| 2015/0133953 A1 * | 5/2015 | Seifert | A61B 17/3468 606/129 |
| 2016/0008141 A1 * | 1/2016 | Huffmaster | A61B 17/320016 623/17.16 |
| 2017/0181892 A1 * | 6/2017 | Kahook | A61F 9/0133 |

FOREIGN PATENT DOCUMENTS

| | | |
|---|---|---|
| WO | 2012023006 A1 | 2/2012 |
| WO | 2017176800 A1 | 10/2017 |

OTHER PUBLICATIONS

Written Opinion of the International Searching Authority; European Patent Office; International Application No. PCT/IB2019/055552; Aug. 16, 2019; 10 pages.
BK Meditech Co., Ltd.; Haki Knife for Percutaneous Release of Trigger Digits; 4 pages.

* cited by examiner

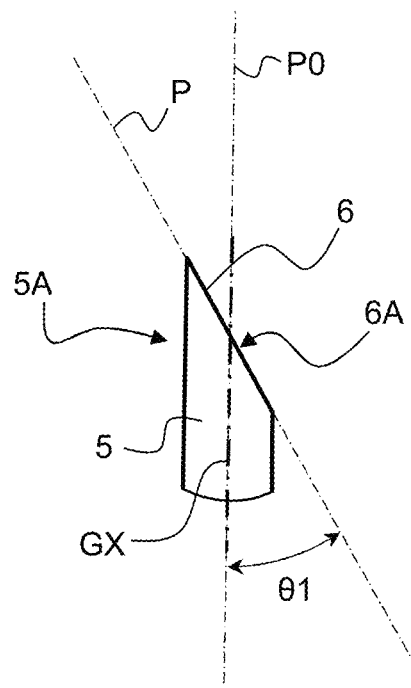
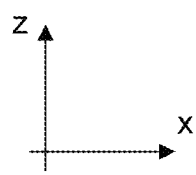
Fig. 6
(DETAIL A)

(DETAIL B)

(CROSS-SECTION C-C)

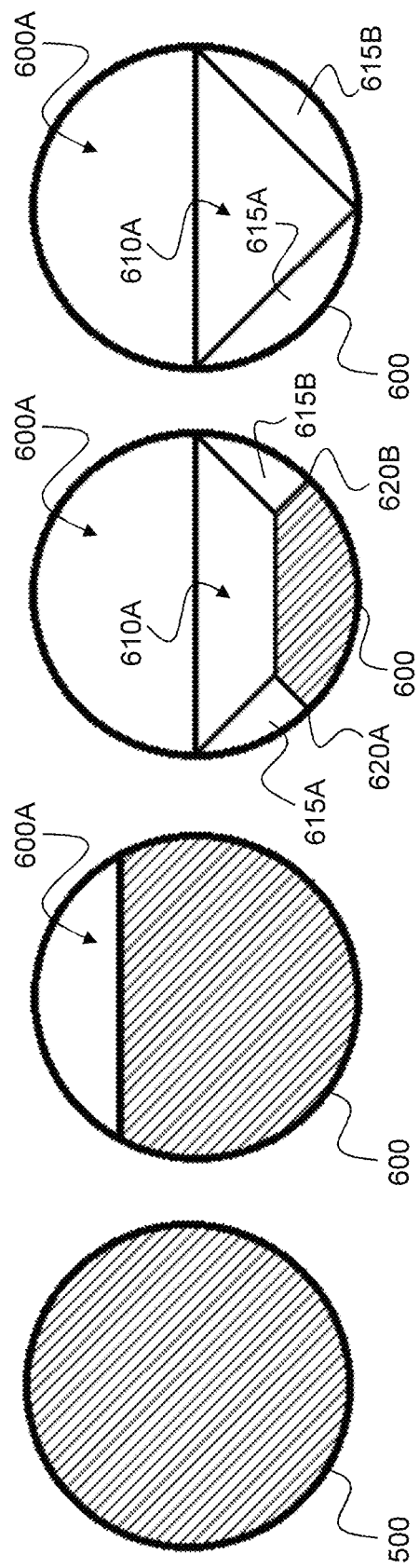

(CROSS-SECTION G-G)

(CROSS-SECTION H-H)

(CROSS-SECTION I-I)

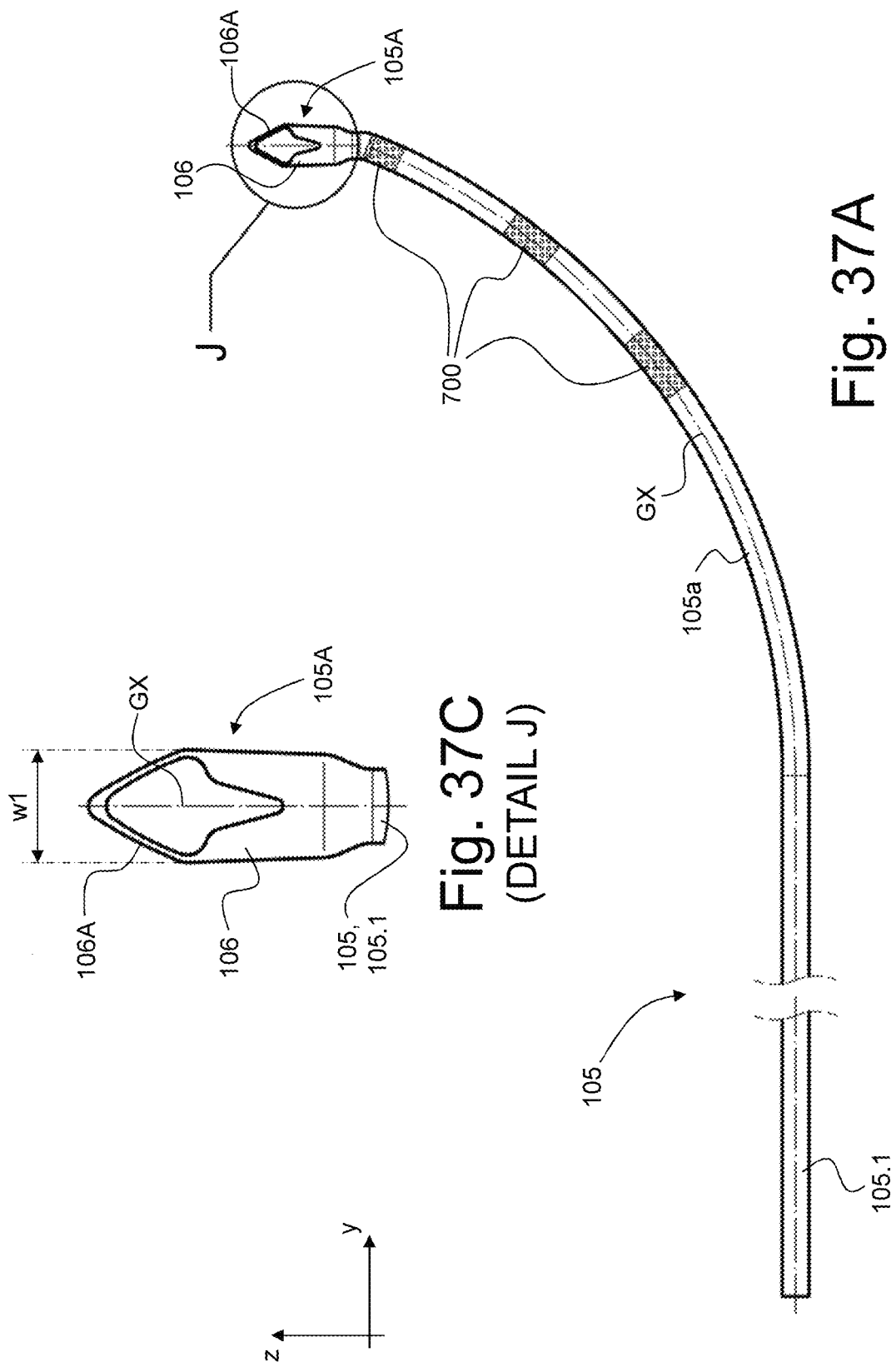

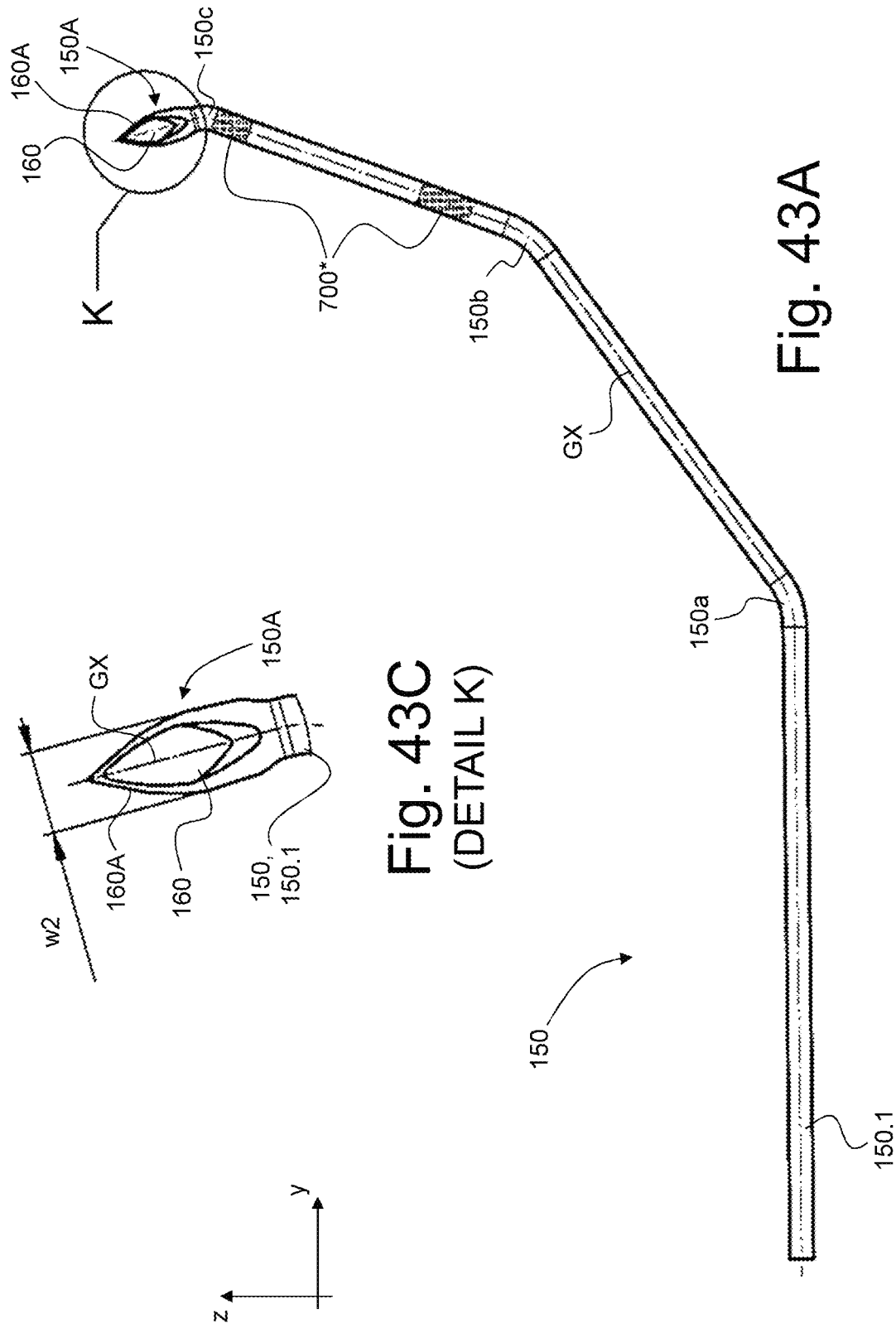

MEDICAL INSTRUMENT FOR PERCUTANEOUS RELEASE PROCEDURES

CROSS REFERENCE TO RELATED APPLICATIONS

This application is a U.S. national stage filing of International Patent Application No. PCT/IB2019/055552 filed Jul. 1, 2019, which claims priority to European Application No. 18180894.0 filed Jun. 29, 2018 and to European Application No. 18206119.2 filed Nov. 14, 2018, the contents of each application hereby incorporated by reference in their entirety.

TECHNICAL FIELD

The present invention generally relates to a medical instrument for percutaneous release procedures, especially percutaneous release procedures on upper or lower limbs, such as but not limited to percutaneous carpal tunnel release and percutaneous A1 pulley release. The invention is also applicable to other release procedures such as but not limited to tenolysis, tenotomy, tenotomy-lengthening, aponeurotomy, neurolysis and neurotomy.

BACKGROUND OF THE INVENTION

Carpal tunnel syndrome (CTS) and trigger finger syndrome (TFS) can conveniently be treated by surgical release procedures. These surgical release procedures are typically carried out using simple puncture needles or more complex hook knives or push knives. Such medical instruments may also be used for other surgical release procedures on upper or lower limbs, such as for the treatment of Morton's neuroma, tarsal tunnel release, de Quervain syndrome, epicondylalgy, shoulder surgery, and similar release procedures, which list is not meant to be exhaustive.

U.S. Pat. No. 5,507,800 A discloses a carpal tunnel tome for performing carpal tunnel release surgery, which tome comprises a handle portion attached to a stem having a head portion, or cutting head, integrally formed thereon. The head portion includes a blade having a cutting edge which is bounded on both sides by a blunt protuberance. During carpal tunnel release surgery, the medical instrument is held in a configuration such that the blade sits substantially vertically, with the blunt protuberances on the lower and upper sides of the blade straddling the ligament. The surgeon then uses the medical instrument as a push knife to progressively cut the ligament. The dimensions and configuration of the aforementioned carpal tunnel tome are such that carpal tunnel release surgery necessitates, as preliminary steps, an incision of the order of 1 to 2 cm on the palmar side of the patient's hand and a sharp dissection using a surgical retractor so as to expose a portion of the ligament. Only then can the carpal tunnel tome be inserted into the wound, with exposure being maintained by the surgical retractor, and be pushed so as to cut through the ligament.

A drawback of the carpal tunnel tome disclosed in U.S. Pat. No. 5,507,800 A therefore resides in the fact that the associated surgical operation is not strictly percutaneous and still requires a relatively large incision in the palmar side of the patient's hand, which necessitates corresponding sutures to close the incision following the surgical procedure.

U.S. Pat. No. 5,029,573 A discloses a system for endoscopic surgery as used for performing carpal tunnel release surgery. According to this patent publication, a probe knife, a triangular cutting instrument and a retrograde cutting instrument of relatively large dimensions are used in combination with a trocar and a sheath, acting as a guide member, that are first inserted underneath the carpal ligament, which requires entry and exit incisions of the order of 1 to 2 cm to be carried out both on the patient's wrist and on the palmar side of the patient's hand. A specific hand rest is furthermore necessary to secure the patient's hand in a hyperextended position to allow full insertion of the trocar and sheath through the carpal tunnel. The trocar and sheath are initially inserted though the patient's hand and carpal tunnel, from the wrist side to the palmar side. Once the trocar and sheath have been fully inserted, the trocar is withdrawn, and an endoscope is then inserted into either one of the open ends of the sheath. The probe knife, triangular cutting instrument and retrograde knife are then used in sequence and inserted through the free end of the sheath to perform release of the carpal ligament.

A drawback of the solution disclosed in U.S. Pat. No. 5,029,573 A thus resides in the fact that the associated surgical operation is likewise not strictly percutaneous and requires two relatively large incisions in the palmar side of the patient's hand as well as on the wrist to allow insertion of the trocar, which necessitates corresponding sutures to close the relevant incisions following the surgical procedure. The surgical operation furthermore requires the use of a set of multiple instruments to complete the release procedure.

U.S. Pat. No. 8,603,124 B1 discloses a modified surgical scalpel for ultrasound assisted carpal tunnel surgery, which modified surgical scalpel is used in combination with a trocar to perform carpal tunnel release.

Percutaneous release procedures can be carried out using simple puncture needles. This solution is not satisfying however since the release procedure is not easy to carry out and potentially dangerous for adjacent structures.

U.S. Pat. No. 5,782,850 A discloses a medical instrument—also referred to as "HAKI knife"—for treating the trigger finger syndrome (TFS), which medical instrument has an operation portion consisting of a tapered cord pointed front end with a first tip pointing forwardly at the front end, a second pointed tip pointing rearwardly relative to the first tip, and a transverse groovelike depression with a hook-shaped cutting edge extending downwardly and rearwardly from and along the entire length of the second tip. Percutaneous release of the A1 pulley can be carried out by means of the aforementioned medical instrument, i.e. without any incision at the point of entry, the medical instrument being used in an anterograde manner, from a proximal to a distal border of the pulley, to progressively cut through the pulley.

A drawback of the medical instrument disclosed in U.S. Pat. No. 5,782,850 A resides in the fact that the configuration thereof is still relatively complex. Furthermore, the configuration of the medical instrument is such that the groovelike depression and hook-shaped cutting edge extending therein may cause unwanted damage to surrounding tissues and structures, especially during withdrawal of the medical instrument.

While these medical instruments may be reasonably satisfactory, there therefore remains a need for an improved solution, especially such a solution that allows minimally invasive surgical release procedures to be carried out, namely in a truly percutaneous manner, and that prevents occurrence of undesired damage to surrounding tissues and structures during insertion and/or withdrawal of the medical instrument.

SUMMARY OF THE INVENTION

A general aim of the invention is to provide an improved medical instrument for percutaneous release procedures, especially percutaneous release procedures on upper or lower limbs, such as percutaneous carpal tunnel release or percutaneous A1 pulley release, as well as other percutaneous release procedures used in the treatment of the conditions or syndromes as for instance listed in the introductory part of this description.

This general aim is achieved, in accordance with a first aspect of the invention, namely a medical instrument for percutaneous release procedures, comprising a handle portion designed to allow handling, orientation and manipulation of the medical instrument by a surgeon and an elongated rod member secured to the handle portion and extending substantially within a defined plane. A first portion of the elongated rod member extends substantially along a first direction within the defined plane away from the handle portion, and a second portion of the elongated rod member, downstream of the first portion, is curved and/or bent within the defined plane. Furthermore, a free end of the elongated rod member, at a terminal end of the second portion, is shaped as a bevelled end exhibiting a bevelled surface, which bevelled end is designed to act as a cutting device to sever tissue, said bevelled surface being inclined with respect to the defined plane.

Advantageous embodiments of the invention form the subject-matter of the dependent claims and are discussed below.

According to a preferred embodiment of the invention, an angle of inclination of a plane comprising the bevelled surface with respect to the defined plane is of the order of 10° to 40°. Even more preferably, the angle of inclination is of the order of 15° to 30°.

According to an advantageous embodiment of this first aspect of the invention, the bevelled end exhibits at least two bevelled surfaces with distinct angles of inclination. These at least two bevelled surfaces facilitate location and orientation of the terminal end of the medical instrument under sonography as the bevelled surfaces will generate different sonographic echoes or signatures due to the distinct angles of inclination.

According to a further embodiment of this first aspect of the invention, a leading edge of the bevelled end, at a distal extremity of the bevelled end, is provided with at least one side bevel defining a cutting edge.

In the aforementioned context, the elongated rod member may in particular be solid and non-hollow.

In accordance with a particularly preferred embodiment of this first aspect of the invention, the elongated rod member extends along a generatrix and a lateral breadth of the elongated rod member as measured at any point along the generatrix, up to and including the terminal end of the second portion, does not exceed 2 mm. This leads to an elongated rod member having a particularly thin configuration, which favours insertion and withdrawal of the medical instrument without causing damage to surrounding tissues or structures.

The aforementioned general aim is also achieved, in accordance with a second aspect of the invention, namely a medical instrument for percutaneous release procedures, comprising a handle portion designed to allow handling, orientation and manipulation of the medical instrument by a surgeon and an elongated rod member secured to the handle portion and extending substantially within a defined plane. A first portion of the elongated rod member extends substantially along a first direction within the defined plane away from the handle portion, and a second portion of the elongated rod member, downstream of the first portion, is curved and/or bent within the defined plane. Furthermore, a free end of the elongated rod member, at a terminal end of the second portion, is flattened to form a flattened section designed to act as a cutting device to sever tissue, which flattened section extends substantially parallel to the defined plane.

According to a preferred embodiment of this second aspect of the invention, the flattened section extends substantially within the defined plane.

Preferably, the flattened section is configured to exhibit a tapered leading edge acting as cutting edge.

The flattened section may in particular exhibit a thickness, as measured perpendicularly to the defined plane, of less than 0.5 mm.

The flattened section may furthermore exhibit a width, as measured in the defined plane, which does not exceed 2.5 mm.

In accordance with a particularly preferred embodiment of this second aspect of the invention, the elongated rod member extends along a generatrix and a lateral breadth of the elongated rod member as measured at any point along the generatrix, up to but not including the terminal end of the second portion, does not exceed 2 mm. This likewise leads to an elongated rod member having a particularly thin configuration, which favours insertion and withdrawal of the medical instrument without causing damage to surrounding tissues or structures.

In the aforementioned context, the elongated rod member preferably comprises a hollow tube member and the flattened section is a flattened free end of the hollow tube member.

Further embodiments of the invention, applicable in the context of both of the aforementioned first and second aspects of the invention, form the subject-matter of additional dependent claims and are discussed below.

Advantageously, an end section of the elongated rod member, at the terminal end of the second portion, extends substantially perpendicularly to the first direction. The end section of the elongated rod member may in particular extend along a second direction that forms an angle with respect to the first direction that is comprised between 80° and 120°.

By way of preference, the first portion of the elongated rod member is a substantially rectilinear section. The first portion of the elongated rod member may in particular have a length of the order of 30 to 60 mm.

According to an embodiment of the invention, the second portion includes at least one curved section extending over an angle that exceeds 30°. In accordance with a first variant of this embodiment, the second portion includes a single curved section extending over an angle that exceeds 60° and a radius of curvature of the curved section is preferably of the order of 30 to 45 mm. In this context, an end section of the elongated rod member, at the terminal end of the second portion, may in particular extend along a second direction perpendicularly to the first direction. In accordance with a second variant of this embodiment, the second portion includes multiple, especially three, curved sections each extending over an angle that does not exceed 40°. In this context, the multiple curved sections may in particular be separated by substantially rectilinear sections preferably having a length of the order of 15 to 25 mm.

According to a particularly advantageous embodiment of the invention, the elongated rod member is provided with a plurality of markings, such as embossings, designed to be distinguishable under sonography. These markings are preferably distributed over the second portion of the elongated rod member. Furthermore, dimensions and/or distribution of the markings along the elongated rod member may advantageously be non-uniform.

Advantageously, the handle portion of the medical instrument may be provided with a visible marking, such as a laser marking, which visible marking is preferably provided on an inner face of the handle portion which is oriented in a same direction as the second portion of the elongated rod member.

By way of preference, a cross-sectional area of the elongated rod member does not exceed 5 mm². Even more preferably, the cross-section area of the elongated rod member does not exceed 2 mm². A diameter of the elongated rod member, upstream of the terminal end, may in particular be of the order of 1 to 2 mm.

According to a particularly preferred embodiment of the invention, the elongated rod member has a substantially circular cross-section upstream of the terminal end.

Also claimed is the use of the medical instrument of the invention for the purpose of performing percutaneous release procedures on upper or lower limbs, especially for the purpose of performing percutaneous carpal tunnel release or for the purpose of performing percutaneous A1 pulley release.

By way of preference, the medical instrument of the invention is used for the purpose of performing percutaneous release procedures, the percutaneous release procedures being performed under the assistance of a sonography. Also claimed is the use of the medical instrument of the invention in combination with a sonography probe. In this context, the medical instrument may in particular be a medical instrument comprising the aforementioned plurality of markings, the plurality of markings being exploited for the purpose of orienting the medical instrument during the percutaneous release procedures. In that regard, an orientation of the medical instrument may especially be automatically detected in sonographic imagery. Advantageously, a virtual representation of the medical instrument may furthermore be superimposed in real time on the sonographic imagery.

BRIEF DESCRIPTION OF THE DRAWINGS

Other features and advantages of the present invention will appear more clearly from reading the following detailed description of embodiments of the invention which are presented solely by way of non-restrictive examples and illustrated by the attached drawings in which:

FIG. 6 is an enlarged view of a terminal end of the medical instrument of FIG. 1 as identified by detail A in FIG. 5;

FIG. 22A is a cross-sectional view of the terminal end of the elongated rod member of the medical instrument of FIGS. 21A and 21B as taken along sectional plane D-D reproduced in FIGS. 21A and 21B, upstream of the bevelled end;

FIG. 22B is a cross-sectional view of the terminal end of the elongated rod member of the medical instrument of FIGS. 21A and 21B as taken along sectional plane E-E reproduced in FIGS. 21A and 21B passing through a first portion of the bevelled end;

FIG. 22C is a cross-sectional view of the terminal end of the elongated rod member of the medical instrument of FIGS. 21A and 21B as taken along sectional plane F-F reproduced in FIGS. 21A and 21B passing through a second portion of the bevelled end;

FIG. 22D is a front view of the terminal end of the elongated rod member of the medical instrument of FIGS. 21A and 21B;

FIG. 37A is a side view of the elongated rod member of FIGS. 36A and 36B after flattening of the terminal end of the elongated rod member;

FIG. 37C is an enlarged view of the flattened end of the elongated rod member of FIG. 37A as identified by detail J in FIG. 37A;

FIG. 43A is a side view of the elongated rod member of FIGS. 42A and 42B after flattening of the terminal end of the elongated rod member;

FIG. 43C is an enlarged view of the flattened end of the elongated rod member of FIG. 43A as identified by detail K in FIG. 43A;

DETAILED DESCRIPTION OF EMBODIMENTS OF THE INVENTION

Figure 1:
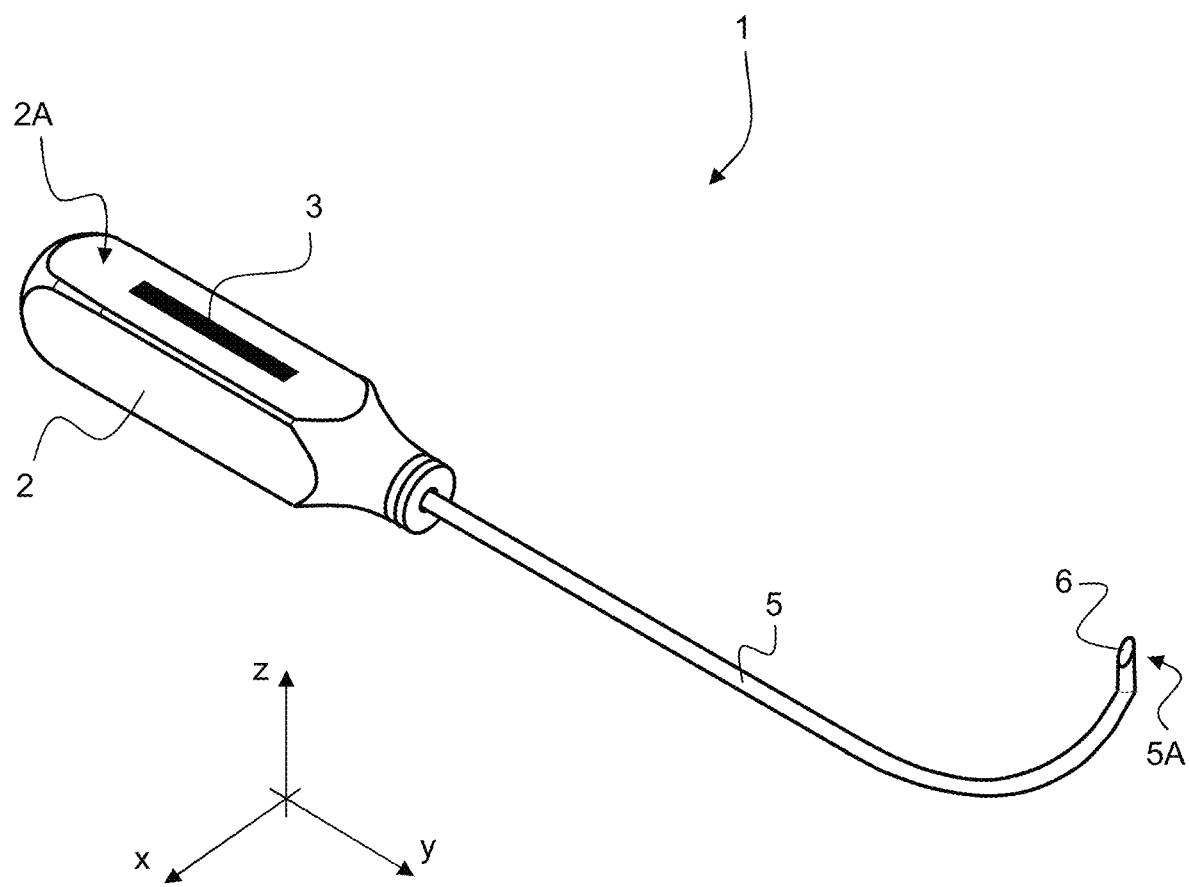
FIG. 1 is a perspective view of a medical instrument in accordance with a first embodiment of the invention, which medical instrument is particularly suited for percutaneous carpal tunnel release in the treatment of the carpal tunnel syndrome.
Figure 2:
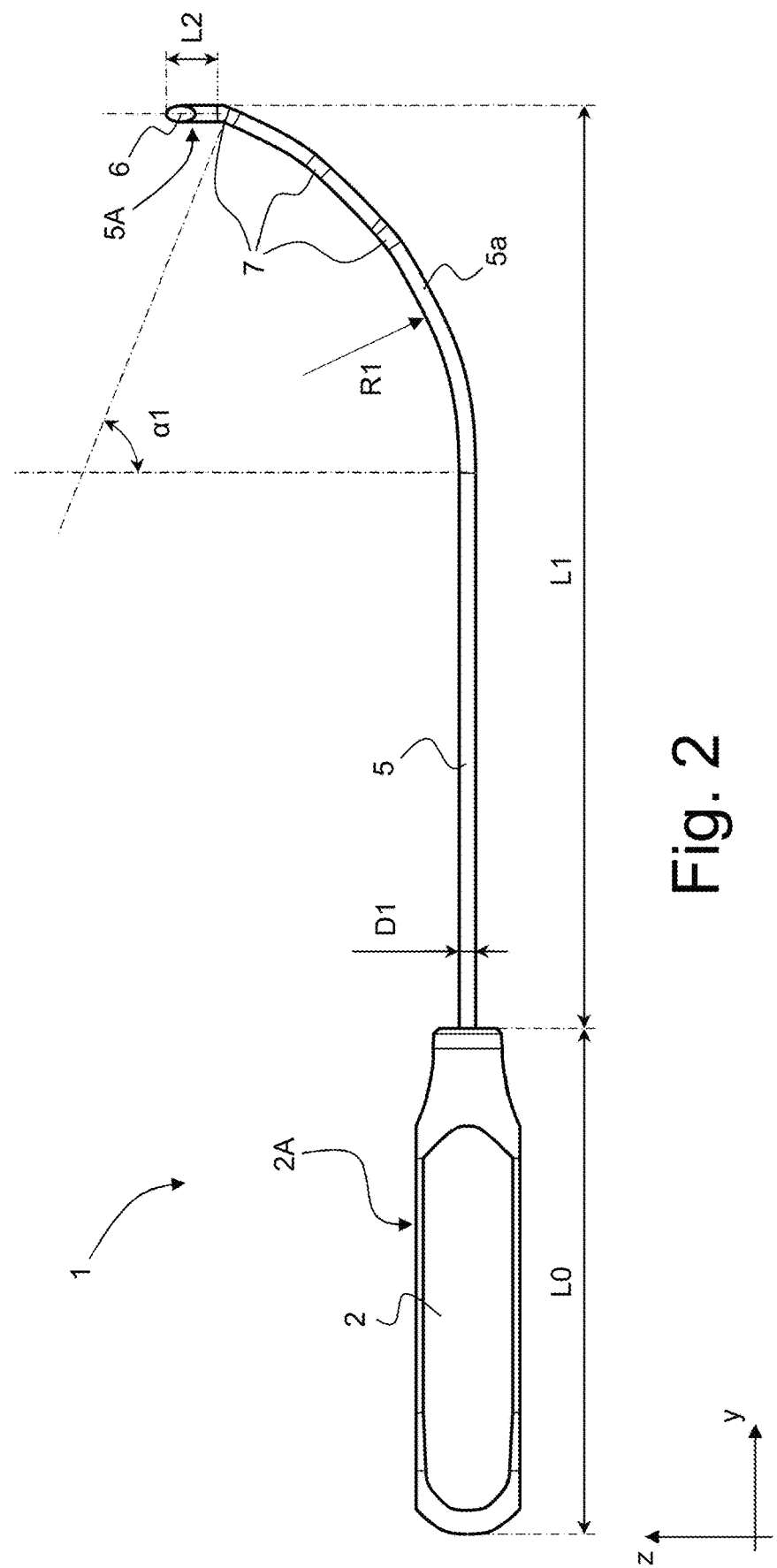
FIG. 2 is a side view of the medical instrument of FIG. 1 as seen along the x axis of a Cartesian coordinate system x-y-z as reproduced in FIG. 1, with the elongated rod member of the medical instrument extending substantially within a defined plane that is parallel to the vertical plane formed by the y and z axes.

The present invention will be described in relation to various illustrative embodiments. It shall be understood that the scope of the invention encompasses all combinations and sub-combinations of the features of the medical instruments disclosed herein.

As described herein, when two or more parts or components are described as being connected, attached, secured or coupled to one another, they can be so connected, attached, secured or coupled directly to each other or through one or more intermediary parts.

Referring to FIGS. 1 to 10, there is shown a first embodiment of a medical instrument, designated by reference numeral 1, in accordance with the present invention, which first embodiment is particularly suited for percutaneous carpal tunnel release in the treatment of the carpal tunnel syndrome (CTS). A variant of this first embodiment, designated by reference numeral 1*, is further shown in FIGS. 23 to 27.

Referring to FIGS. 11 to 20, there is shown another embodiment of a medical instrument, designated by reference numeral 10, in accordance with the present invention, which other embodiment is particularly suited for percutaneous A1 pulley release in the treatment of the trigger finger syndrome (TFS). A variant of this second embodiment, designated by reference numeral 10\*, is further shown in FIGS. 28 to 31.

Further embodiments of the invention are discussed with reference to FIGS. 32 to 43A-C. FIGS. 32 to 37A-C illustrate a further embodiment of a medical instrument 100 that is particularly suited for percutaneous carpal tunnel release in the treatment of the carpal tunnel syndrome (CTS), while FIGS. 38 to 43A-C illustrate another embodiment of a medical instrument 110 that is particularly suited for percutaneous A1 pulley release in the treatment of the trigger finger syndrome (TFS).

All embodiments share a number of common features, including a handle portion 2, 20, 200 resp. 200\*, designed to allow handling, orientation and manipulation of the medical instrument by a surgeon and an elongated rod member **5, 50, 5\*, 50\*, 105 resp. 150, secured to the handle portion 2, 20, 200, resp. 200\*, and extending substantially within a defined plane, designated by reference P0. Referring to the Cartesian coordinate system x-y-z reproduced in the drawings, this defined plane P0** is assumed to be a vertical plane parallel to the vertical plane formed by the y and z axes.

As shown in the illustrations (see especially FIGS. 3, 13, 23, 28, 32 and 38), a first portion of the elongated rod member **5, 50, 5\*, 50\*, 105, resp. 150, extends substantially along a first direction a1, resp. a1', within the defined plane P0 away from the handle portion 2, 20, 200, resp. 200\*, namely parallel to the y axis. This first portion can especially be a substantially rectilinear section. In addition, a second portion of the elongated rod member 5, 50, 5\*, 50\*, 105, resp. 150, downstream of the first portion, is curved and/or bent within the defined plane P0. Reference sign GX in the Figures designates a generatrix along which the elongated rod member 5, 50, 5\*, 50\*, 105, resp. 150**, extends.

Figure 28:
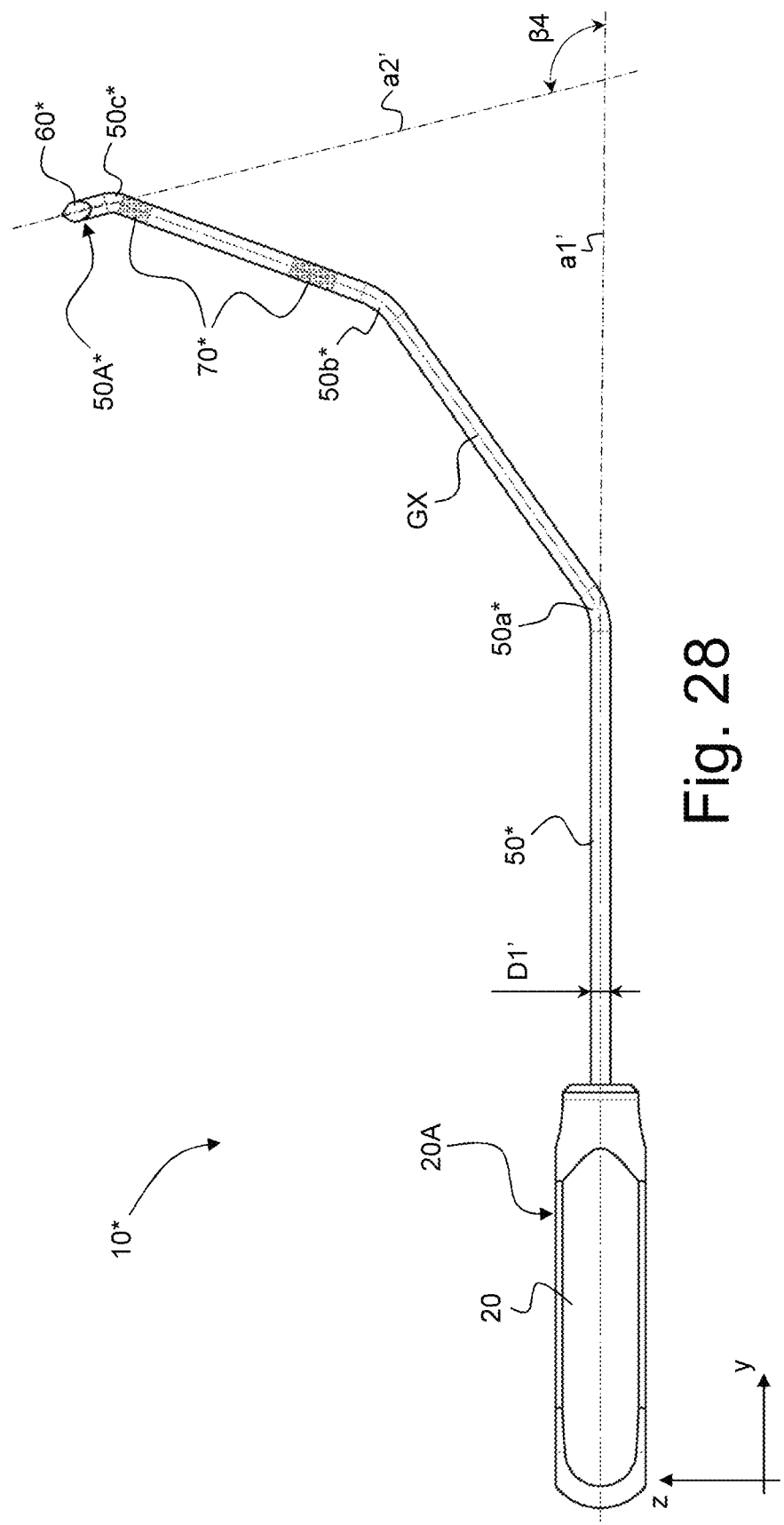
FIG. 28 is a side view of a variant of the medical instrument of FIGS. 11 to 20 as seen along the x axis of a Cartesian coordinate system x-y-z, with the elongated rod member of the medical instrument extending substantially within a defined plane that is parallel to the vertical plane formed by the y and z axes.
Figure 29:
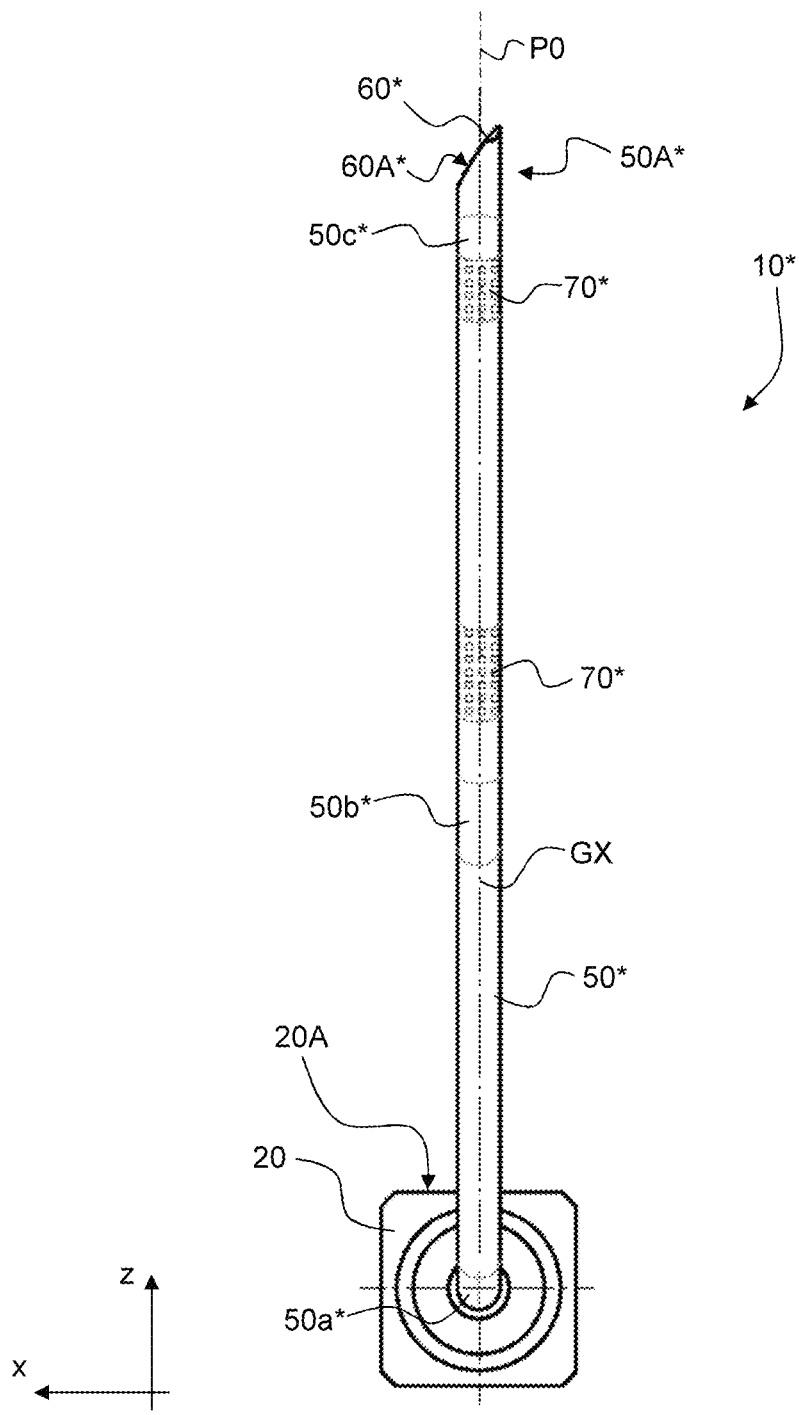
FIG. 29 is a front view of the medical instrument of FIG. 28 as seen along the y axis.
Figure 30:
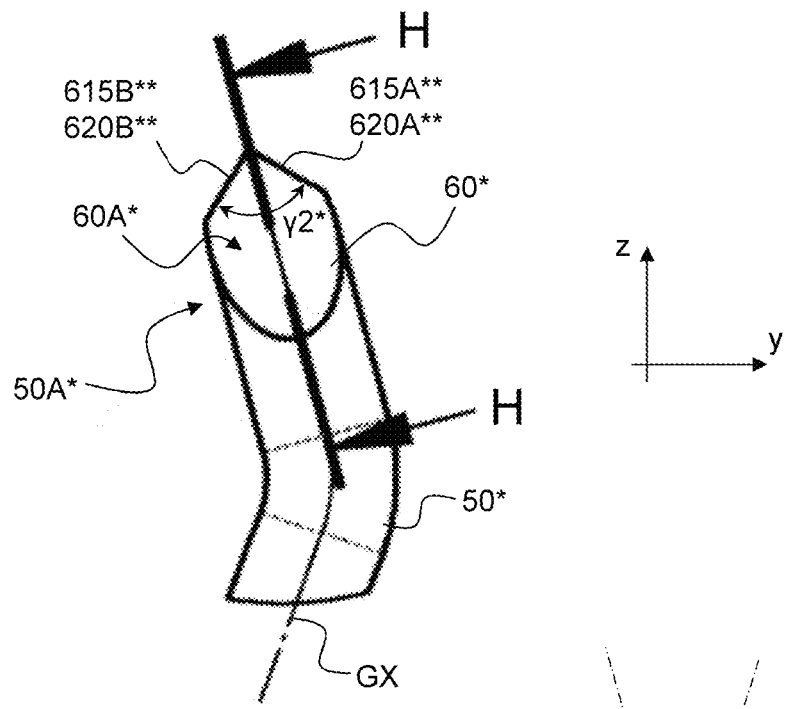
FIG. 30 is an enlarged view of a terminal end of the medical instrument of FIG. 28 as seen along the x axis.
Figure 31:
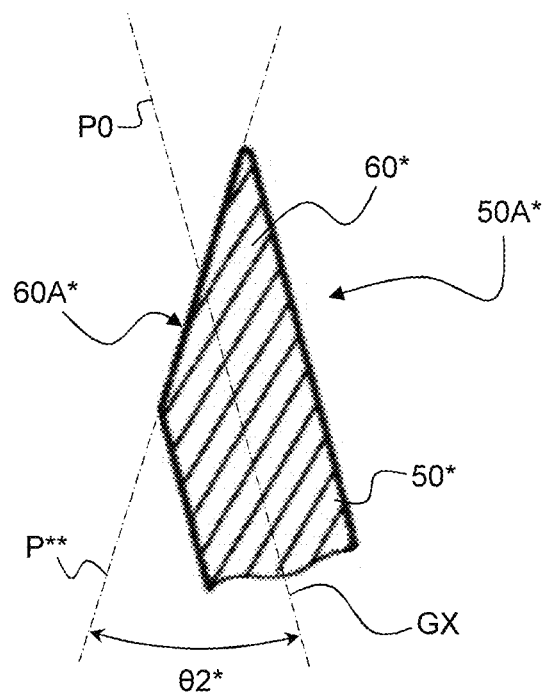
FIG. 31 is a cross-sectional view of the terminal end of the medical instrument of FIG. 28 as taken along sectional plane H-H reproduced in FIG. 30.

Furthermore, with regard to the embodiments illustrated in FIGS. 1 to 20 and 28 to 31, a free end of the elongated rod member 5, 50, 5\*, resp. 50\*, at a terminal end 5A, 50A, 5A\*, resp. 50A\*, of the second portion, is shaped as a bevelled end 6, 60, 6\*, resp. 60\*, exhibiting a bevelled surface 6A (see FIGS. 5 and 6), 60A (see FIGS. 14 to 16), 6A\* (see FIGS. 25 to 27), resp. 60A\* (see FIGS. 29 to 31). This bevelled end 6, 60, 6\*, resp. 60\*, is designed to act as a cutting device to sever tissue, the bevelled surface 6A, 60A, 6A\*, resp. 60A\*, being inclined with respect to the defined plane P0.

By way of preference, the angle of inclination θ1, θ2, θ1\*, resp. θ2\*, of a plane P, P', P\*, resp. P\*\*, comprising the bevelled surface 6A (see FIG. 6), 60A (see FIG. 16), 6A\* (see FIG. 27), resp. 60A\* (see FIG. 31) with respect to the defined plane P0 is of the order of 10° to 40°, even more preferably of the order of 15° to 30°. In the examples of FIGS. 1 to 20 and 28 to 31, angles of inclination θ1, θ2 and θ2\* are each of the order of 30°, whereas in the example of FIGS. 23 to 27, angle of inclination θ1\* is of the order of 15°.

FIGS. 21A-B and 22A-D show a configuration of a bevelled end 600, at a terminal end 500A of an elongated rod member 500 of a medical instrument in accordance with another embodiment of the present invention. This configuration is especially applicable in the context of the aforementioned medical instruments as shown in FIGS. 1 to 20.

In contrast to the embodiments shown in FIGS. 1 to 20 where the bevelled end 6, resp. 60, exhibits a single bevelled surface 6A, resp. 60A, the bevelled end 600 shown in FIGS. 21A-B and 22A-D exhibits at least two bevelled surfaces 600A, 610A having distinct angles of inclination 83 and 84 with respect to the defined plane P0 (references P'' and P''' here designating the relevant planes comprising the bevelled surfaces 600A, 610A, respectively). This configuration is particularly advantageous for the purpose of locating and orienting the terminal end 500A of the medical instrument under sonography as the bevelled surfaces 600A, 610A will generate different sonographic echoes or signatures due to the distinct angles of inclination 83, 84.

In the context of the configuration shown in FIGS. 21A-B and 22A-D, the angle of inclination θ3 of the plane P''' comprising the bevelled surface 600A with respect to the defined plane P0 is of the order of 15° and the angle of inclination 64 of the plane P'''' comprising the bevelled surface 610A with respect to the defined plane P0 is of the order of 30°.

FIGS. 21A-B and 22A-D further illustrate another advantageous feature in accordance with a further embodiment of the invention, which feature is likewise applicable in the context of the aforementioned medical instruments as shown in FIGS. 1 to 20, independently of the number of bevelled surfaces. As shown in FIGS. 21A-B and 22A-D, a leading edge of the bevelled end 600, at a distal extremity of the bevelled end 600, is provided with at least one side bevel 615A, 615B defining a corresponding cutting edge 620A, 620B. In the example of FIGS. 21A-B and 22A-D, two side bevels 615A and 615B are provided at the leading edge of the bevelled end 600, leading to the definition of two corresponding cutting edges 620A and 620B. As this can be appreciated from looking at the cross-sectional view of FIG. 22C, the provision of the side bevels 615A, 615B leads to sharper cutting edges 620A, 620B, improving the ability to cut through tissues. It shall be appreciated that only one side bevel could be provided on one or the other side of the bevelled end 600, rather than on both sides as illustrated.

In the illustrations of FIGS. 21A-B and 22A-D, the side bevels 615A, 615B are angled with respect to the longitudinal axis of the terminal end 500A of the elongated rod member 500 and form an angle γ1 of the order of 50°.

Figure 26:
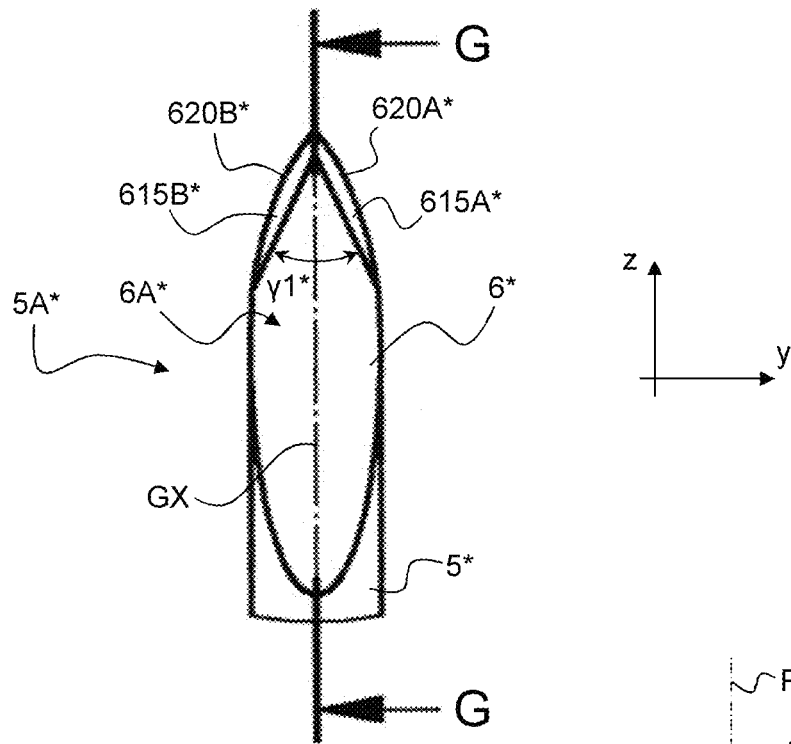
FIG. 26 is an enlarged view of a terminal end of the medical instrument of FIG. 23 as seen along the x axis.
Figure 27:
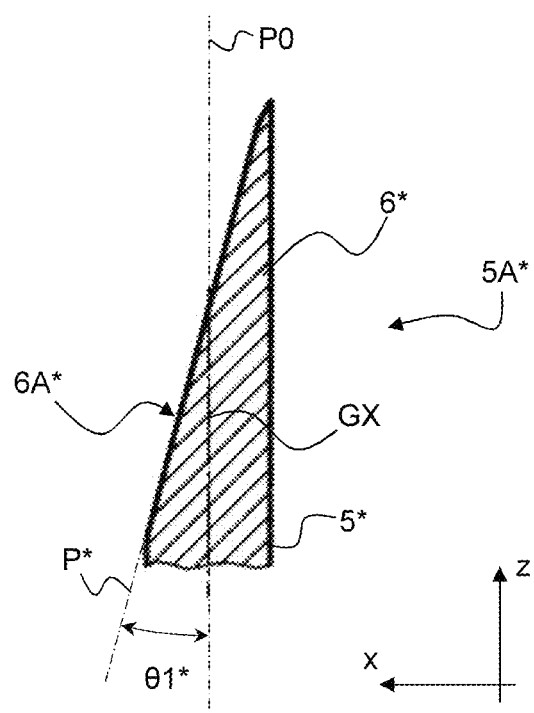
FIG. 27 is a cross-sectional view of the terminal end of the medical instrument of FIG. 23 as taken along sectional plane G-G reproduced in FIG. 26.

A similar feature is embodied in the variant shown in FIGS. 23 to 27, where a leading edge of the bevelled end 6\*, at a distal extremity of the bevelled end 6\*, is provided with at least one side bevel **615A\*, 615B\* defining a corresponding cutting edge 620A\*, 620B\* (see FIG. 26). In the example of FIGS. 23 to 27, two side bevels 615A\* and 615B\* are likewise provided at the leading edge of the bevelled end 6\*, leading to the definition of two corresponding cutting edges 620A\* and 620B\*. The provision of the side bevels 615A\*, 615B\* similarly leads to sharper cutting edges 620A\*, 620B\*, improving the ability to cut through tissues. The side bevels 615A\*, 615B\* are likewise angled with respect to the longitudinal axis of the terminal end 5A\* of the elongated rod member 5\* and form an angle γ1\*** of the order of 50°.

FIGS. 28 to 31 illustrate yet another embodiment of the aforementioned feature, where a leading edge of the bevelled end 60\*, at a distal extremity of the bevelled end 60\*, is provided with at least one side bevel **615A\*\*, 615B\*\* defining a corresponding cutting edge 620A\*\*, 620B\*\* (see FIG. 30). In the example of FIGS. 28 to 31, two side bevels 615A\*\* and 615B\*\* are once again provided at the leading edge of the bevelled end 60\*, leading to the definition of two corresponding cutting edges 620A\*\* and 620B\*\*. In contrast to the previous examples, the side bevels 615A\*\* and 615B\*\* are more pronounced, leading to a more angular configuration of the resulting cutting edges 620A\*\*, 620B\*\*, which likewise improves the ability to cut through tissues. The side bevels 615A\*\*, 615B\*\*, and resulting cutting edges 620A, 620B are angled with respect to the longitudinal axis of the terminal end 50A* of the elongated rod member 50* and form an angle γ2* of the order of 90° in this other example.

With regard to the embodiments illustrated in FIGS. 32 to 37A-C and 38 to 43A-C, a free end of the elongated rod member 105, resp. 150, at a terminal end 105A, resp. 150A, of the second portion, is flattened to form a flattened section 106, resp. 160, designed to act as a cutting device to sever tissue. This flattened section 106, resp. 160, extends substantially parallel to the defined plane P0. By way of preference, as illustrated in FIGS. 33, 34, 37B, 39, 40 and 43B, the flattened section 106, resp. 160, extends substantially within the defined plane P0.

In the illustrated example, the elongated rod member 105, resp. 150, advantageously comprises a hollow tube member 105.1, resp. 150.1, the flattened section 106, resp. 160, being formed by flattening (e.g. crushing) the free end of the hollow tube member 105.1, resp. 150.1.

Figure 35A:
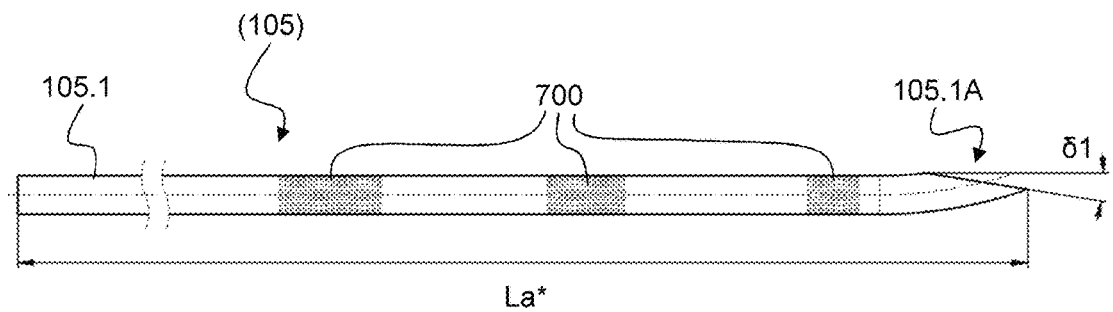
FIG. 35A is a side view of the elongated rod member of the medical instrument of FIGS. 32 to 34 prior to shaping and flattening thereof.
Figure 35B:
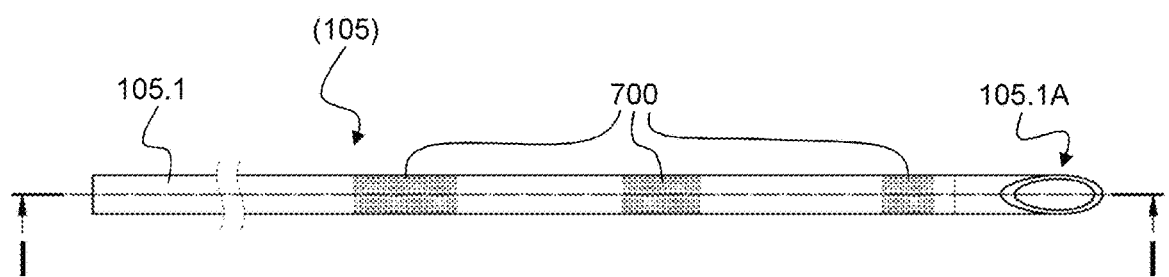
FIG. 35B is a top view of the elongated rod member of FIG. 35A.
Figure 35C:
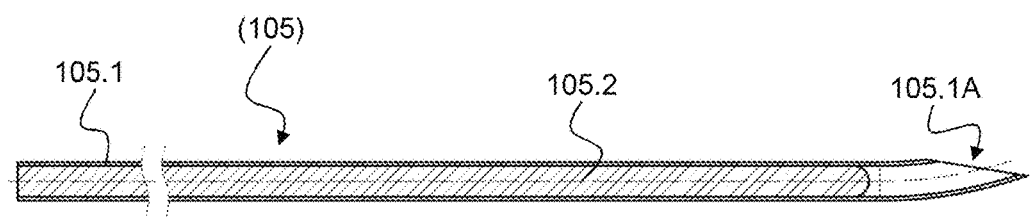
FIG. 35C is a cross-sectional view of the elongated rod member of FIGS. 35A and 35B as taken along sectional plane I-I reproduced in FIG. 35B.
Figure 36A:
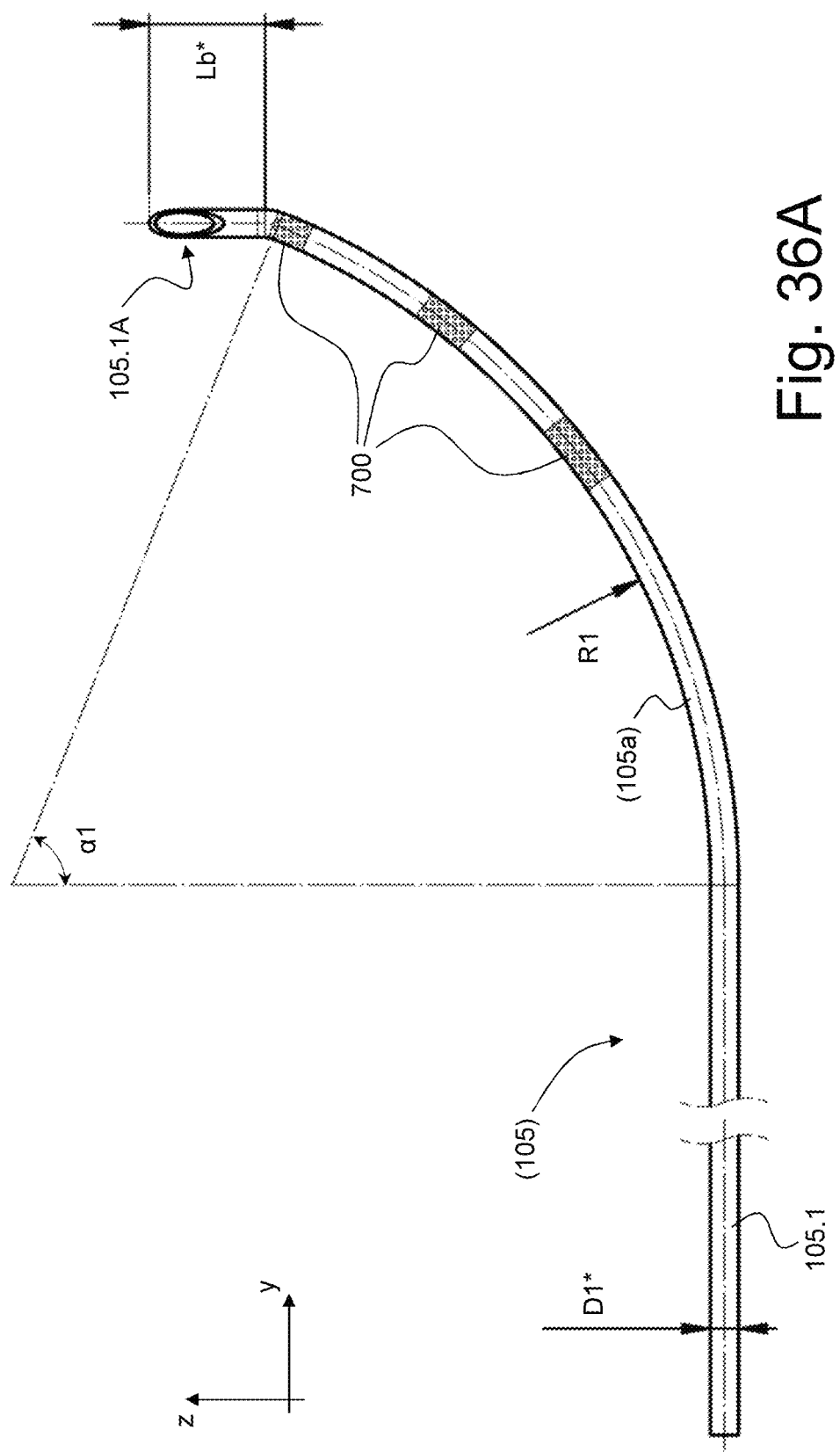
FIG. 36A is a side view of the elongated rod member of FIGS. 35A to 35C after shaping thereof and prior to flattening of a terminal end of the elongated rod member.
Figure 36B:
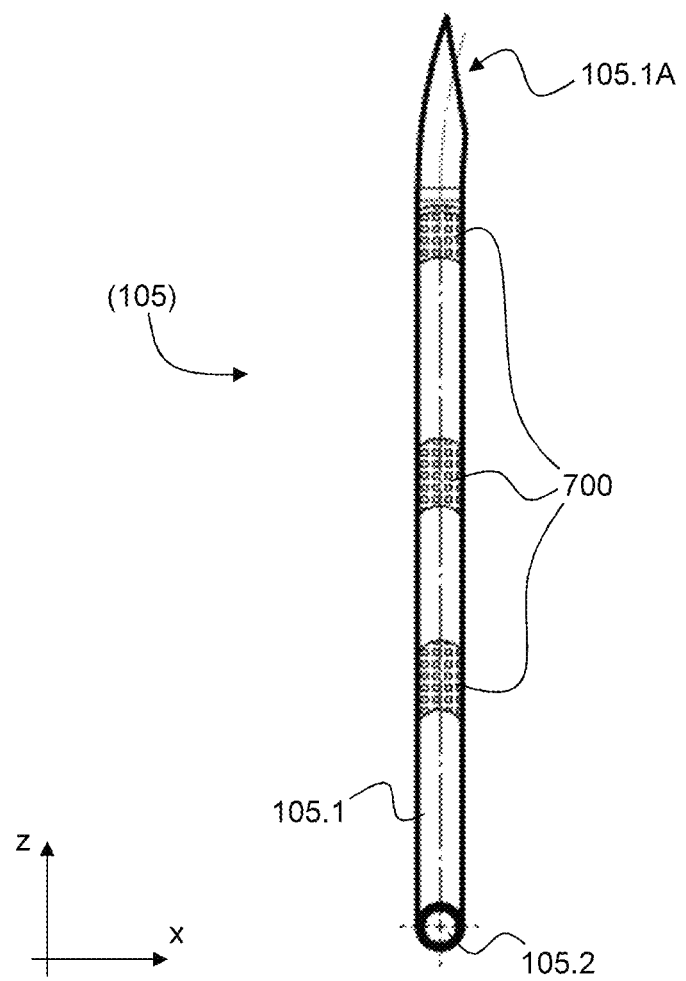
FIG. 36B is a rear view of the elongated rod member of FIG. 36A.
Figure 37B:
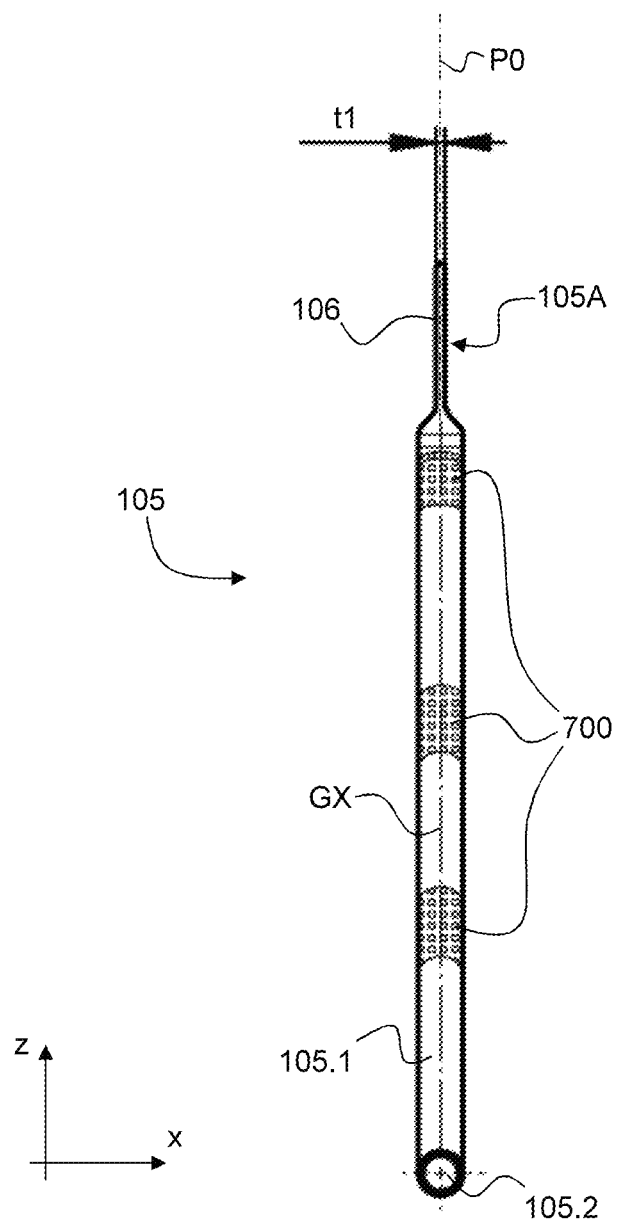
FIG. 37B is a rear view of the elongated rod member of FIG. 37A.

FIGS. 35A-C illustrate the elongated rod member 105 prior to shaping and flattening thereof to form the elongated rod member 105 as shown in FIGS. 32 to 34 and 37A-C. More specifically, in the illustrated example, the elongated rod member 105 further includes an inner member 105.2 (see especially FIG. 35C) inserted through a portion of the hollow tube member 105.1, leaving a free end 105.1A of the hollow tube member 105.1. In the state illustrated in FIGS. 35A-C, the elongated rod member 105 is still substantially rectilinear. By way of illustration, the overall length La* of the elongated rod member 105 in this state (i.e. prior to shaping into a curved configuration as shown in FIGS. 36A-B) is of the order of 110 mm. The elongated rod member 105 is subsequently shaped into the curved configuration shown in FIGS. 36A-B and the free end 105.1A of the hollow tube member 105.1 is then crushed to form the flattened section 106 as shown in FIGS. 37A-C.

By way of preference, the free end 105.1A of the hollow tube member 105.1 is initially machined to be slightly curved and to exhibit a bevelled end with a defined angle of inclination δ1 as shown in FIG. 35A. By way of illustration, the angle of inclination δ1 is here chosen to be of the order of 9°. Crushing of the free end 105.1A of the hollow tube member 105.1 thus leads to the formation of a flattened section 106 having the configuration as generally depicted in FIGS. 37A-C, with a characteristic tapered leading edge 106A acting as cutting edge. Preferably, the thickness t1 of the flattened section 106, as measured perpendicularly to the defined plane P0, is reduced to less than 0.5 mm, while the width w1 of the flattened section 106, as measured in the defined plane P0, does not exceed 2.5 mm. By way of illustration, thickness t1 and width w1 are here of 0.3 mm and 2.3 mm, respectively.

Figure 41A:
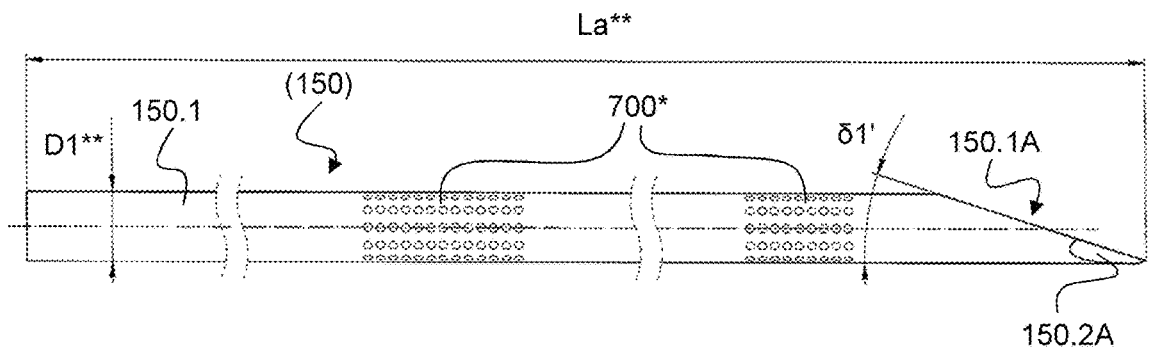
FIG. 41A is a side view of the elongated rod member of the medical instrument of FIGS. 38 to 40 prior to shaping and flattening thereof.
Figure 41B:
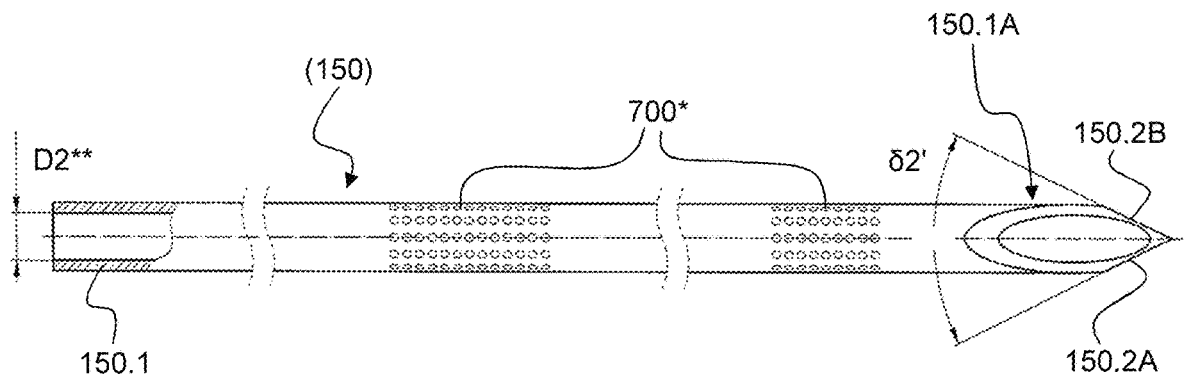
FIG. 41B is a top view of the elongated rod member of FIG. 41A.
Figure 42A:
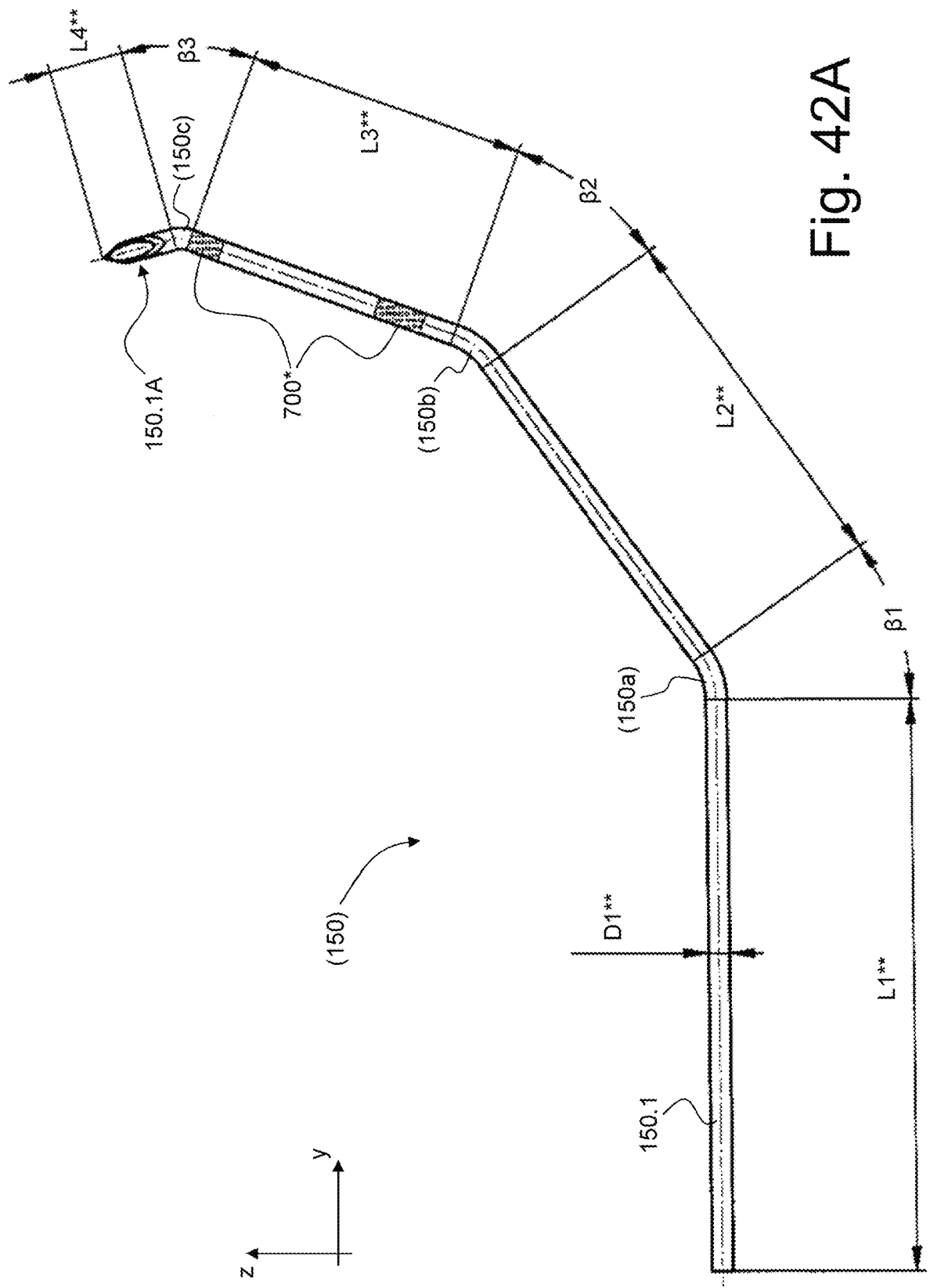
FIG. 42A is a side view of the elongated rod member of FIGS. 41A and 41B after shaping thereof and prior to flattening of a terminal end of the elongated rod member.
Figure 42B:
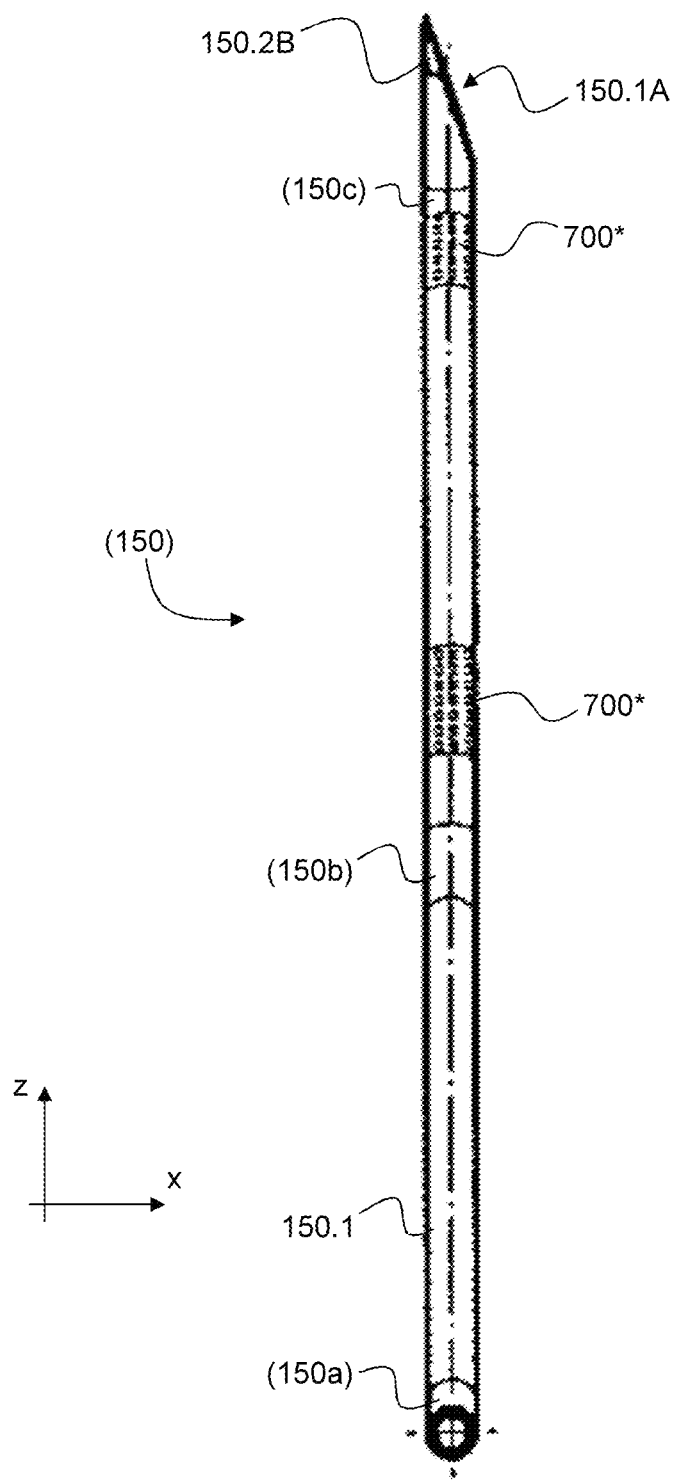
FIG. 42B is a rear view of the elongated rod member of FIG. 42A.
Figure 43B:
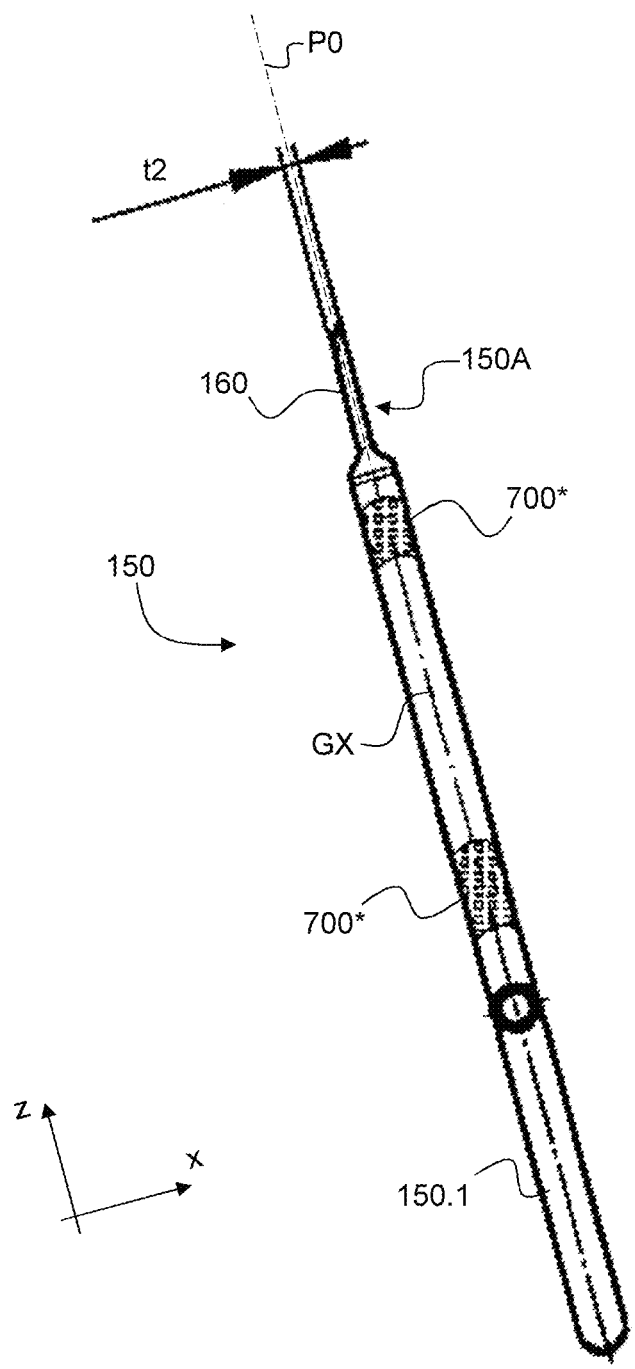
FIG. 43B is a rear view of the elongated rod member of FIG. 43A.

FIGS. 41A-B illustrate the elongated rod member 150 prior to shaping and flattening thereof to form the elongated rod member 150 as shown in FIGS. 38 to 40 and 43A-C. While this is not illustrated, the elongated rod member 150 may likewise include an inner member inserted through a portion of the hollow tube member 150.1. In the state illustrated in FIGS. 41A-B, the elongated rod member 150 is still substantially rectilinear. By way of illustration, the overall length La** of the elongated rod member 150 in this state (i.e. prior to shaping into the curved and bent configuration as shown in FIGS. 42A-B) is of the order of 85 mm. The elongated rod member 150 is subsequently shaped into the curved and bent configuration shown in FIGS. 42A-B and the free end 150.1A of the hollow tube member 150.1 is then crushed to form the flattened section 160 as shown in FIGS. 43A-C.

By way of preference, the free end 150.1A of the hollow tube member 150.1 is initially machined to exhibit a bevelled end with a defined angle of inclination δ1' as shown in FIG. 41A. Furthermore, two side bevels 150.2A, 150.2B forming an angle δ1' may be formed at the leading edge of the free end 150.1A of the hollow tube member 150.1 as shown in FIG. 41B. By way of illustration, the angle of inclination δ1' is here chosen to be of the order of 17.5°, while the angle δ2' formed by the side bevels 150.2A, 150.2B is of the order of 52°. Crushing of the free end 150.1A of the hollow tube member 150.1 thus leads to the formation of a flattened section 160 having the configuration as generally depicted in FIGS. 43A-C, with a characteristic tapered leading edge 160A acting as cutting edge. Preferably, the thickness t2 of the flattened section 160, as measured perpendicularly to the defined plane P0, is likewise reduced to less than 0.5 mm, while the width w2 of the flattened section 160, as measured in the defined plane P0, similarly does not exceed 2.5 mm. By way of illustration, thickness t2 and width w2 are here of 0.4 mm and 1.8 mm, respectively.

Turning back to the illustrations of FIGS. 1 to 20, 23 to 31 and 32 to 43A-C, parts of the curved or bent second portion of the elongated rod member 5, 50, 5*, 50*, 105 resp. 150, can especially be exploited during surgery as a fulcrum to facilitate severance of the desired tissue. In effect, parts of the curved or bent second portion can suitably be used to bear on underlying tissues or onto an additional instrument inserted for that very purpose, thereby providing support for manipulation of the medical instrument during the severance operation.

It will also be appreciated that the medical instrument of the invention advantageously exhibits a minimal cross-section that in essence corresponds to the cross-section of the elongated rod member, which greatly facilitates penetration through the tissues, with minimal interference both during insertion of the medical instrument in the area to be treated and during withdrawal thereof. Furthermore, the limited cross-sectional area of the elongated member (which by way of preference does not exceed 5 mm$^2$, and even more preferably is less than 2 mm$^2$) is such that surgery can be carried out in a truly percutaneous manner without this necessitating any incision at the point of entry of the medical instrument, but merely a puncture, which therefore heals without any noticeable scar for the patient, much like an intravenous infusion.

By way of preference, referring to the embodiments illustrated in FIGS. 1 to 31, a lateral breadth of the elongated rod member 5A, 50A, 500A, 5A*, resp. 50A*, as measured at any point along the generatrix GX, up to and including the terminal end 5A, 50A, 500A, 5A*, resp. 50A*, of the second portion, does not exceed 2 mm. More specifically, in the illustrated examples, the lateral breadth of the elongated rod member 5A, 50A, 500A, 5A*, resp. 50A* does not exceed diameter D1, resp. D1'. Similarly, referring to the embodiments illustrated in FIGS. 32 to 43A-C, a lateral breadth of the elongated rod member 105, resp. 150, as measured at any point along the generatrix GX, up to but not including the terminal end 105A, resp. 150A, of the second portion, preferably does not exceed 2 mm. More specifically, in the illustrated examples, the lateral breadth of the elongated rod member 105, resp. 150, up to the flattened section 106, resp. 160, does not exceed diameter D1*, resp. D1 **. In other words, the elongated rod member 5A, 50A, 500A, 5A*, 50A*, 105, resp. 150, is of a particularly thin configuration, which favours insertion and withdrawal of the medical instrument without causing damage to surrounding tissues or structures.

As this will be appreciated from reading further the following description, the medical instrument of the invention is of simple construction and is therefore economical to produce.

Figure 3:
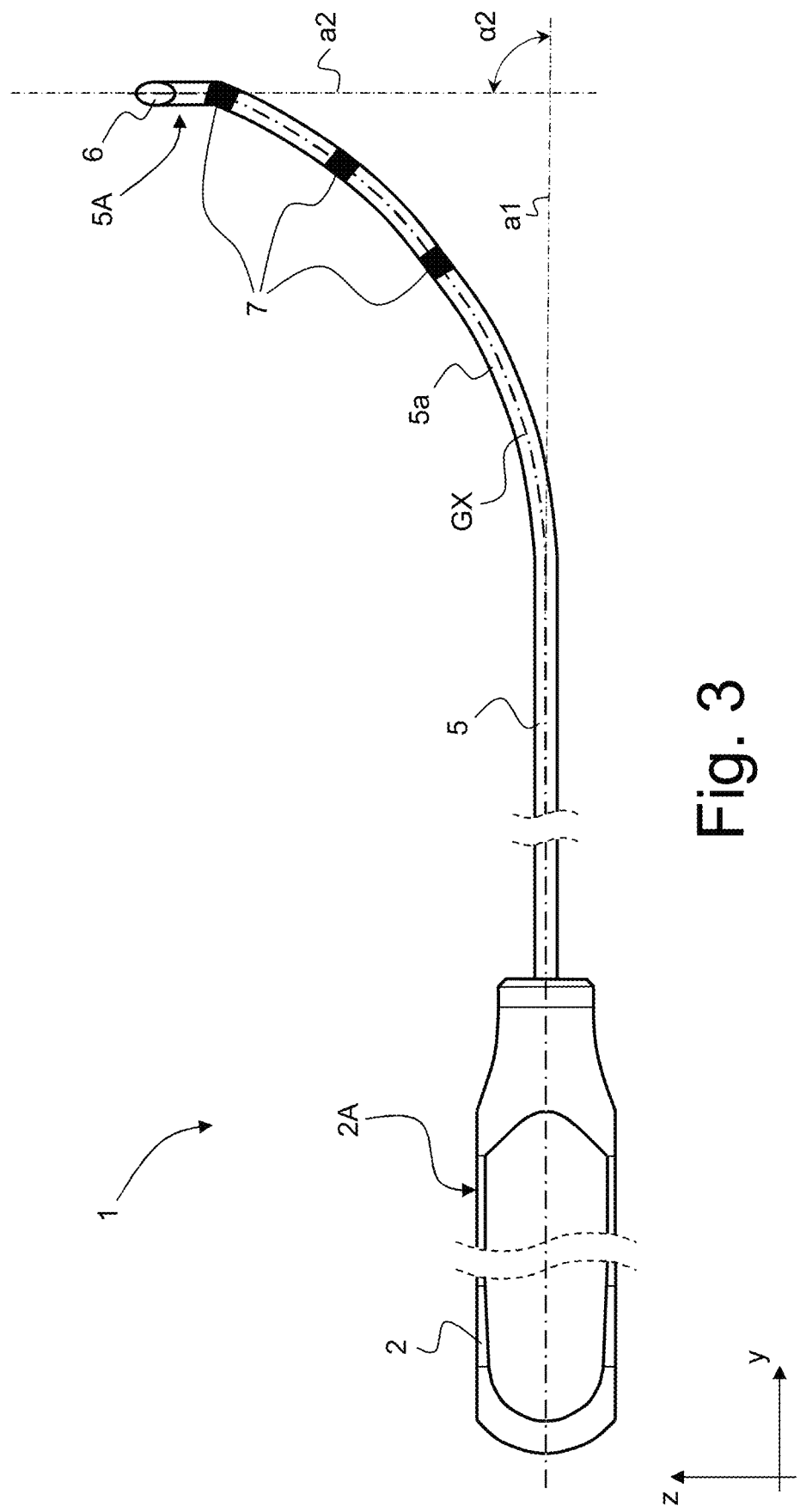
FIG. 3 is another side view of the medical instrument of FIG. 1 as seen along the x axis.
Figure 4:
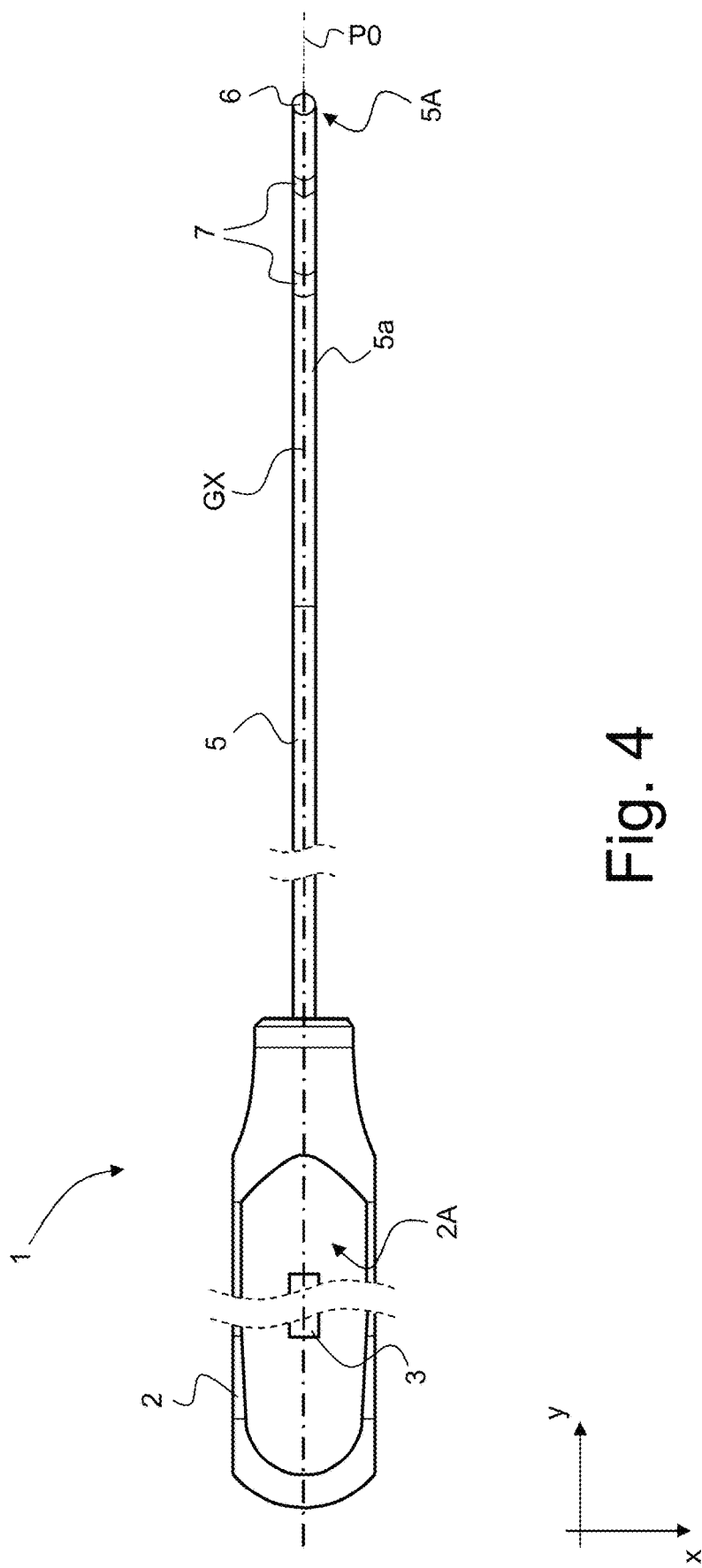
FIG. 4 is a top view of the medical instrument of FIG. 1 as seen along the z axis.
Figure 5:
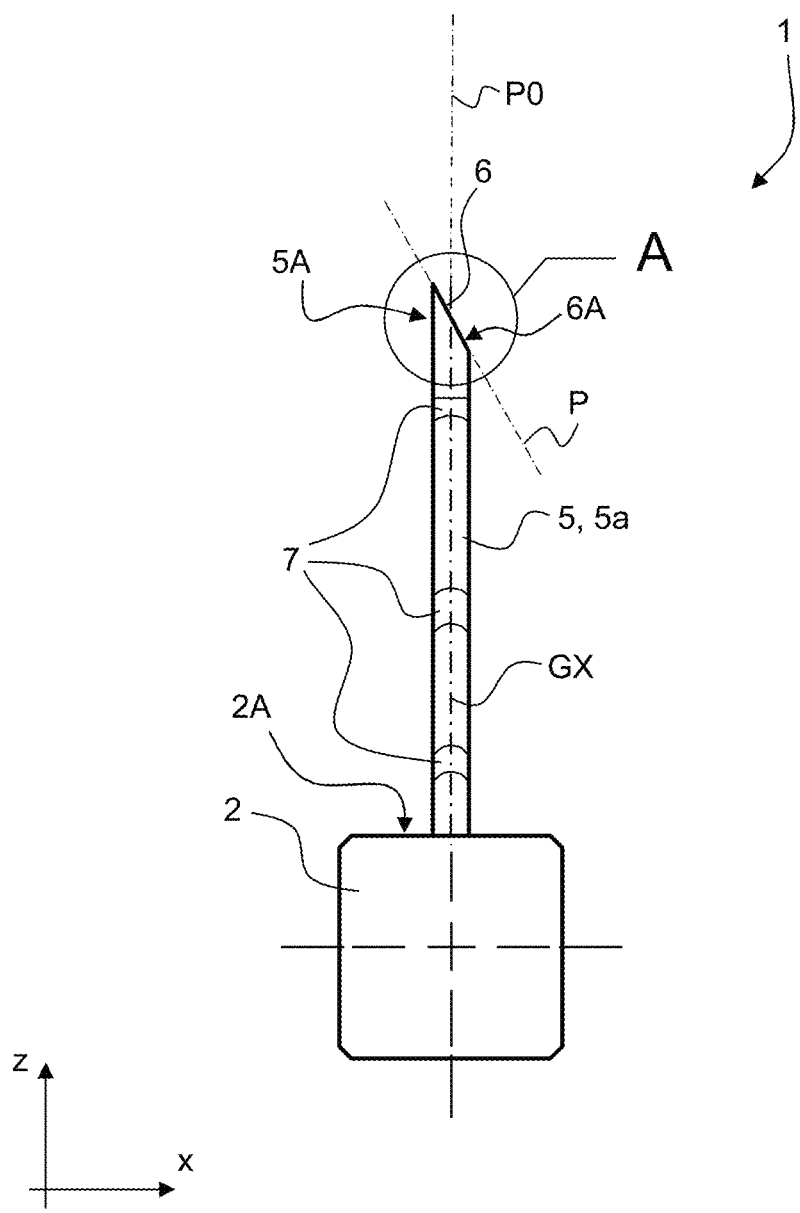
FIG. 5 is a rear view of the medical instrument of FIG. 1 as seen along the y axis.
Figure 7:
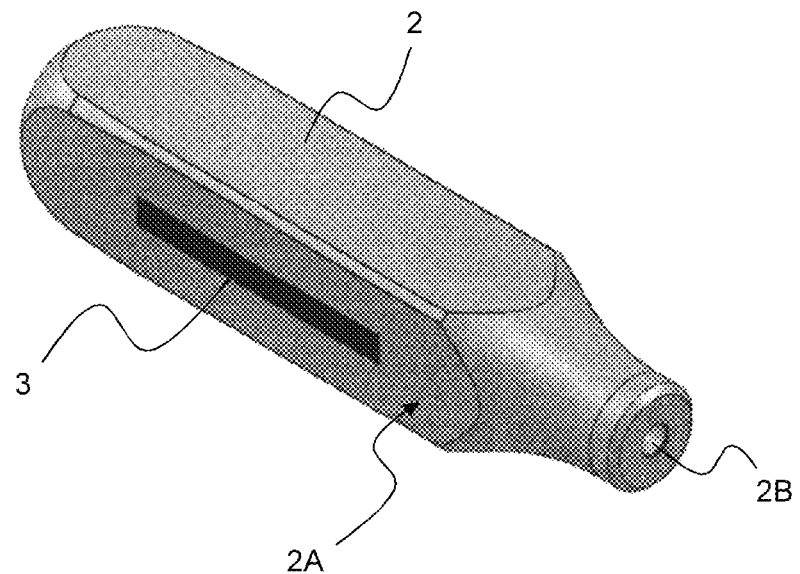
FIG. 7 is a perspective view of a handle portion of the medical instrument of FIG. 1.
Figure 8:
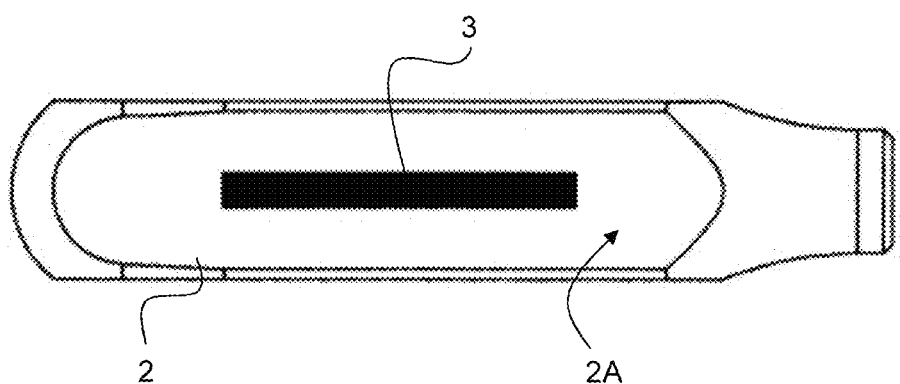
FIG. 8 is a side view of the handle portion of FIG. 7 where a visible marking is provided.
Figure 9:
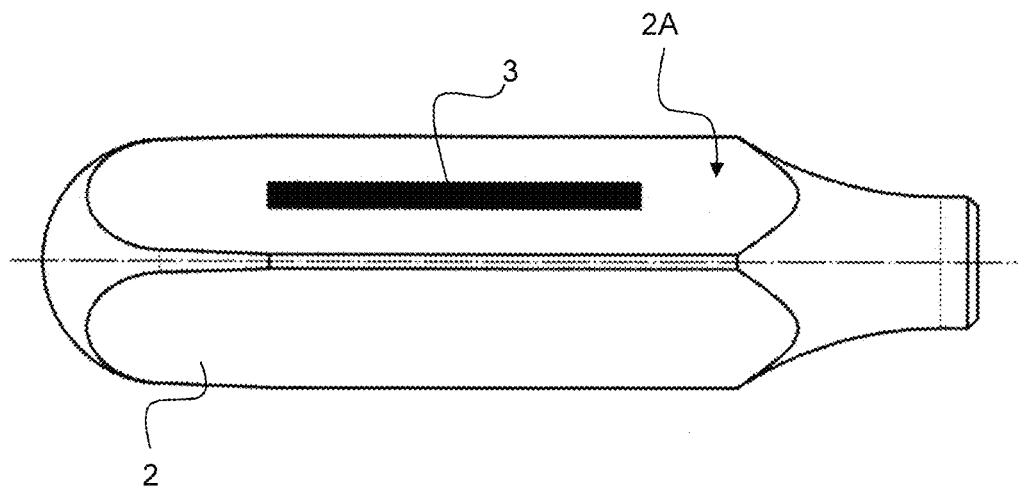
FIG. 9 is another side view of the handle portion of FIG. 7 taken from a different perspective.
Figure 10:
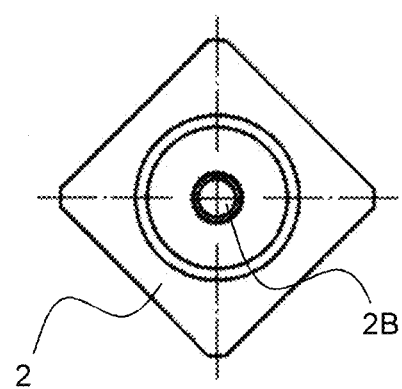
FIG. 10 is a front view of the handle portion of FIG. 7 where the handle portion is secured to the elongated rod member of the medical instrument.
Figure 11:
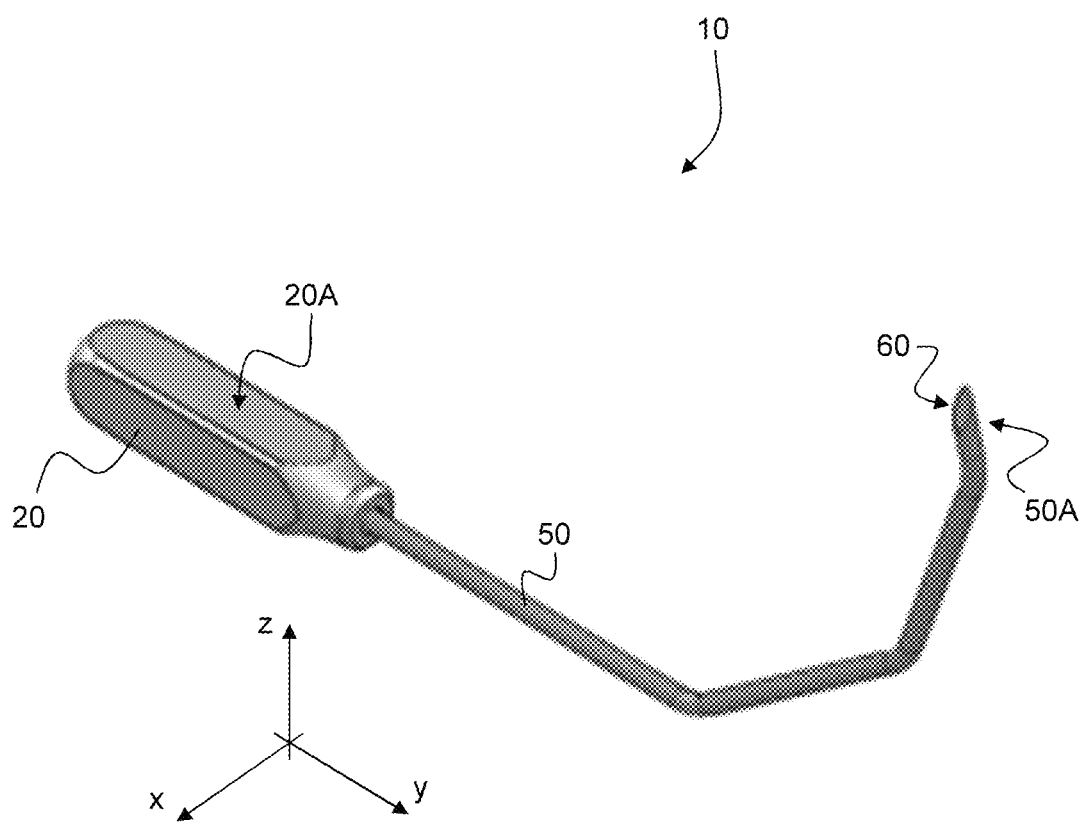
FIG. 11 is a perspective view of a medical instrument in accordance with another embodiment of the invention, which medical instrument is particularly suited for percutaneous A1 pulley release in the treatment of the trigger finger syndrome.
Figure 12:
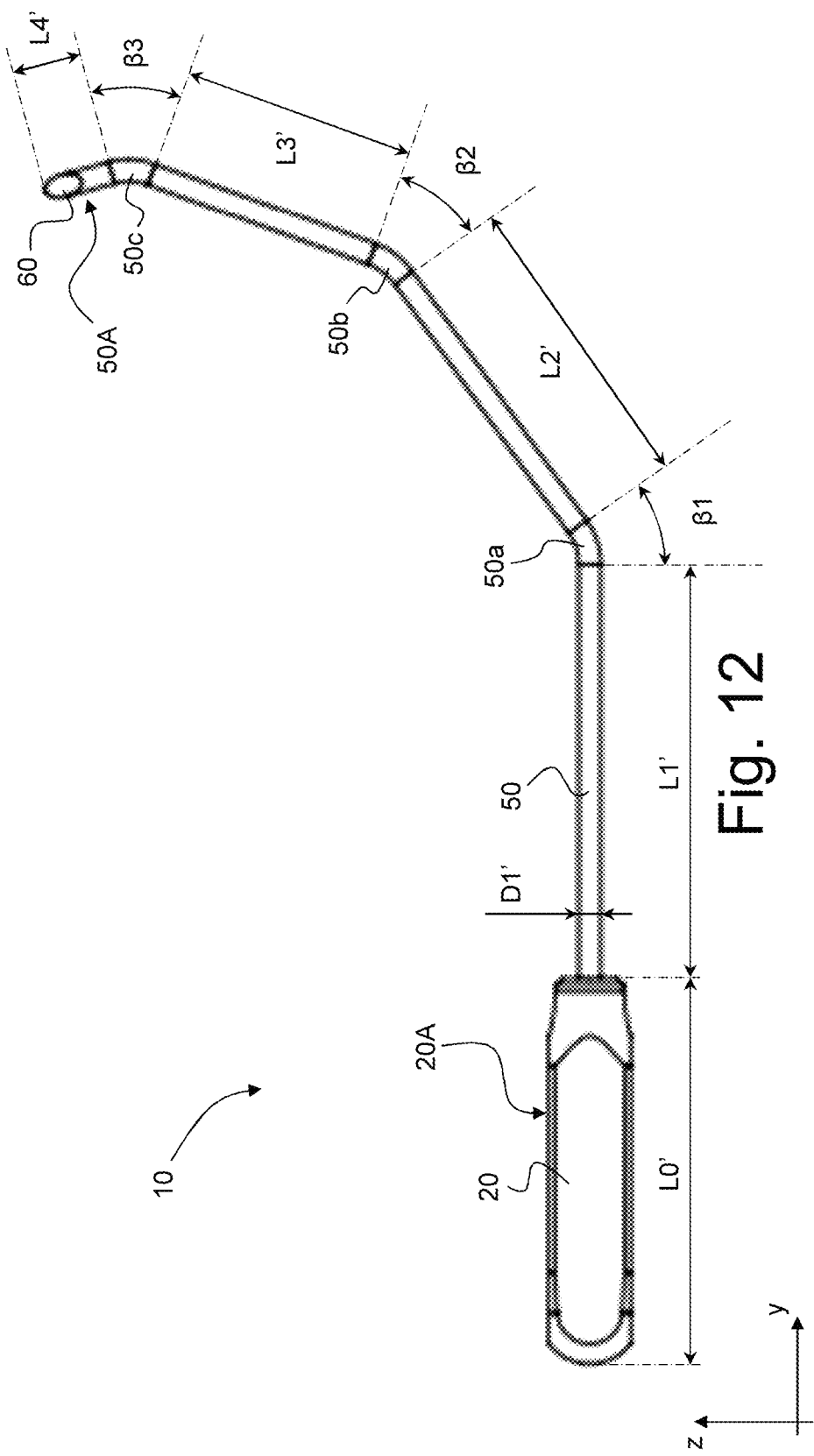
FIG. 12 is a side view of the medical instrument of FIG. 11 as seen along the x axis of a Cartesian coordinate system x-y-z as reproduced in FIG. 11, with the elongated rod member of the medical instrument extending substantially within a defined plane that is parallel to the vertical plane formed by the y and z axes.
Figure 23:
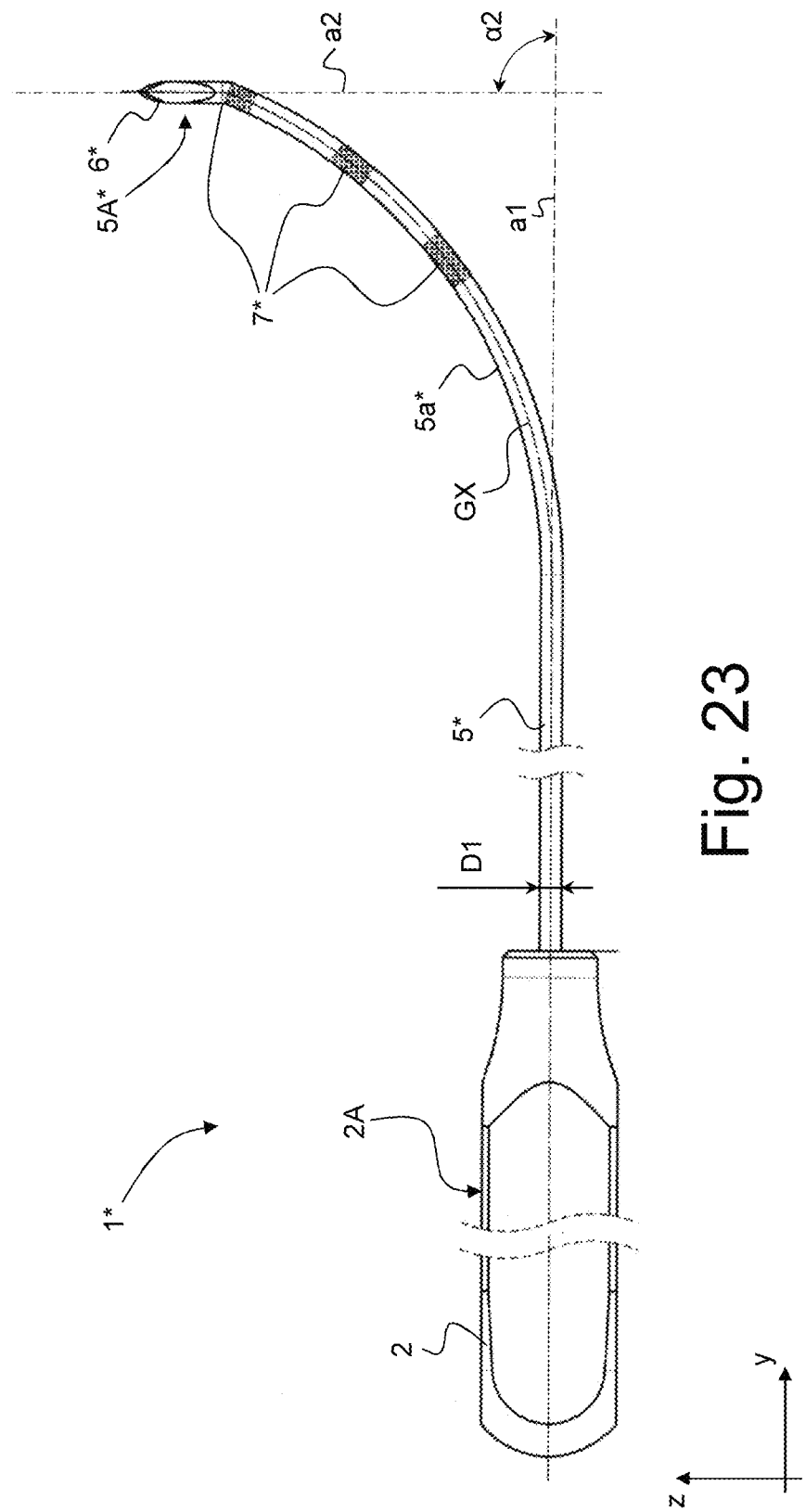
FIG. 23 is a side view of a variant of the medical instrument of FIGS. 1 to 10 as seen along the x axis of a Cartesian coordinate system x-y-z, with the elongated rod member of the medical instrument extending substantially within a defined plane that is parallel to the vertical plane formed by the y and z axes.
Figure 24:
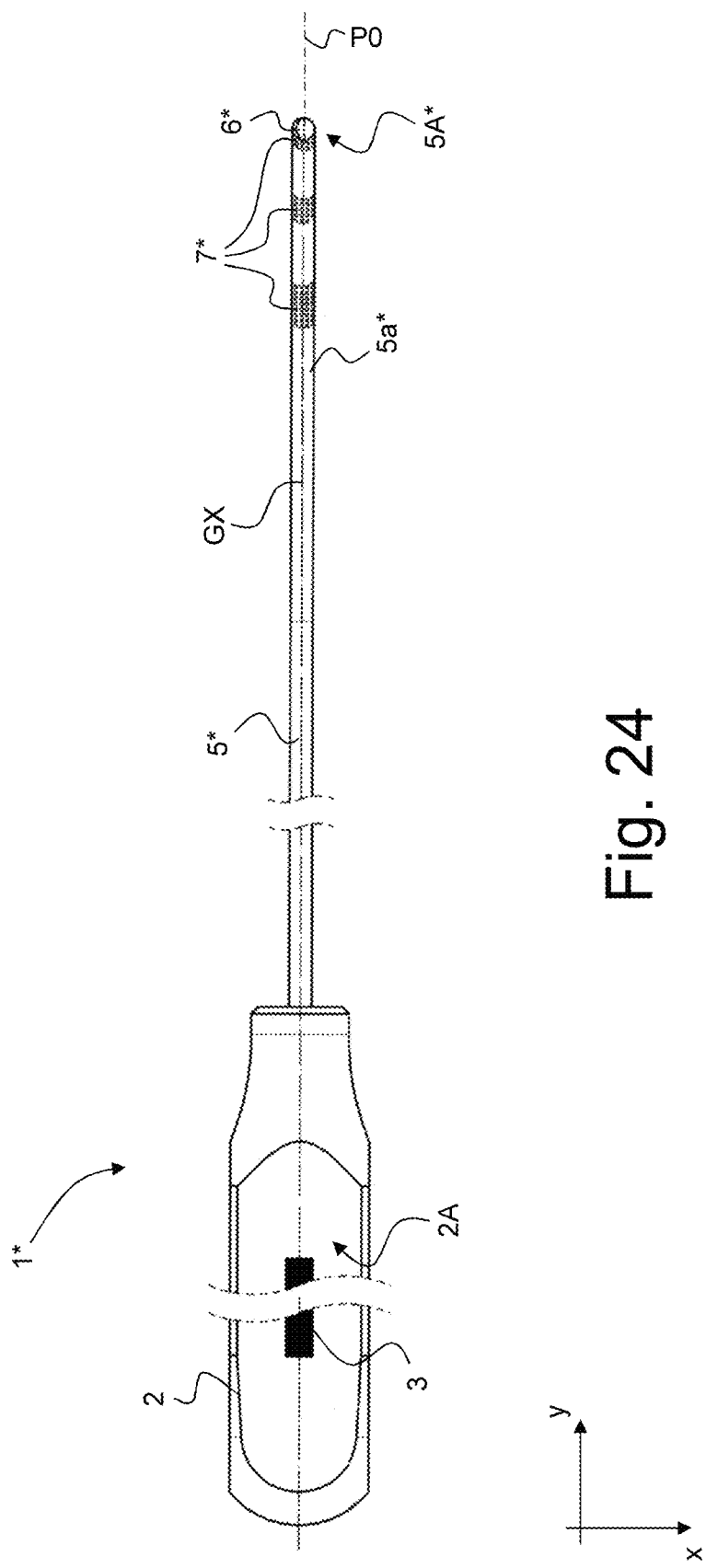
FIG. 24 is a top view of the medical instrument of FIG. 23 as seen along the z axis.
Figure 25:
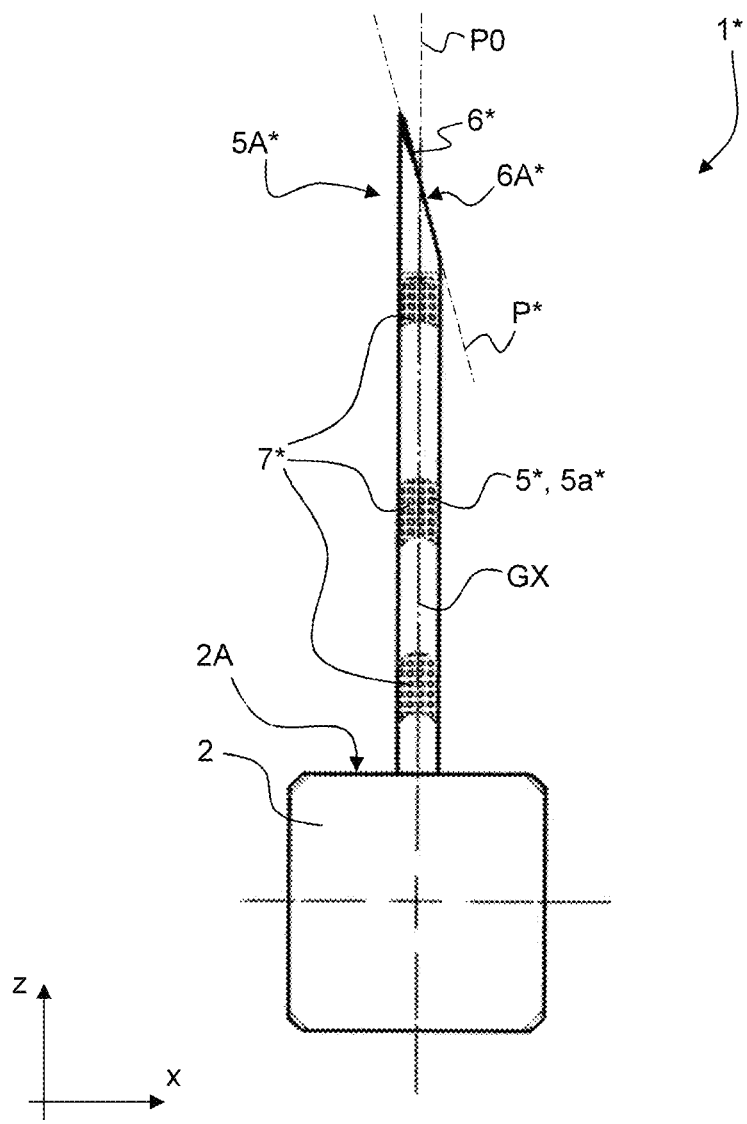
FIG. 25 is a rear view of the medical instrument of FIG. 23 as seen along the y axis.
Figure 32:
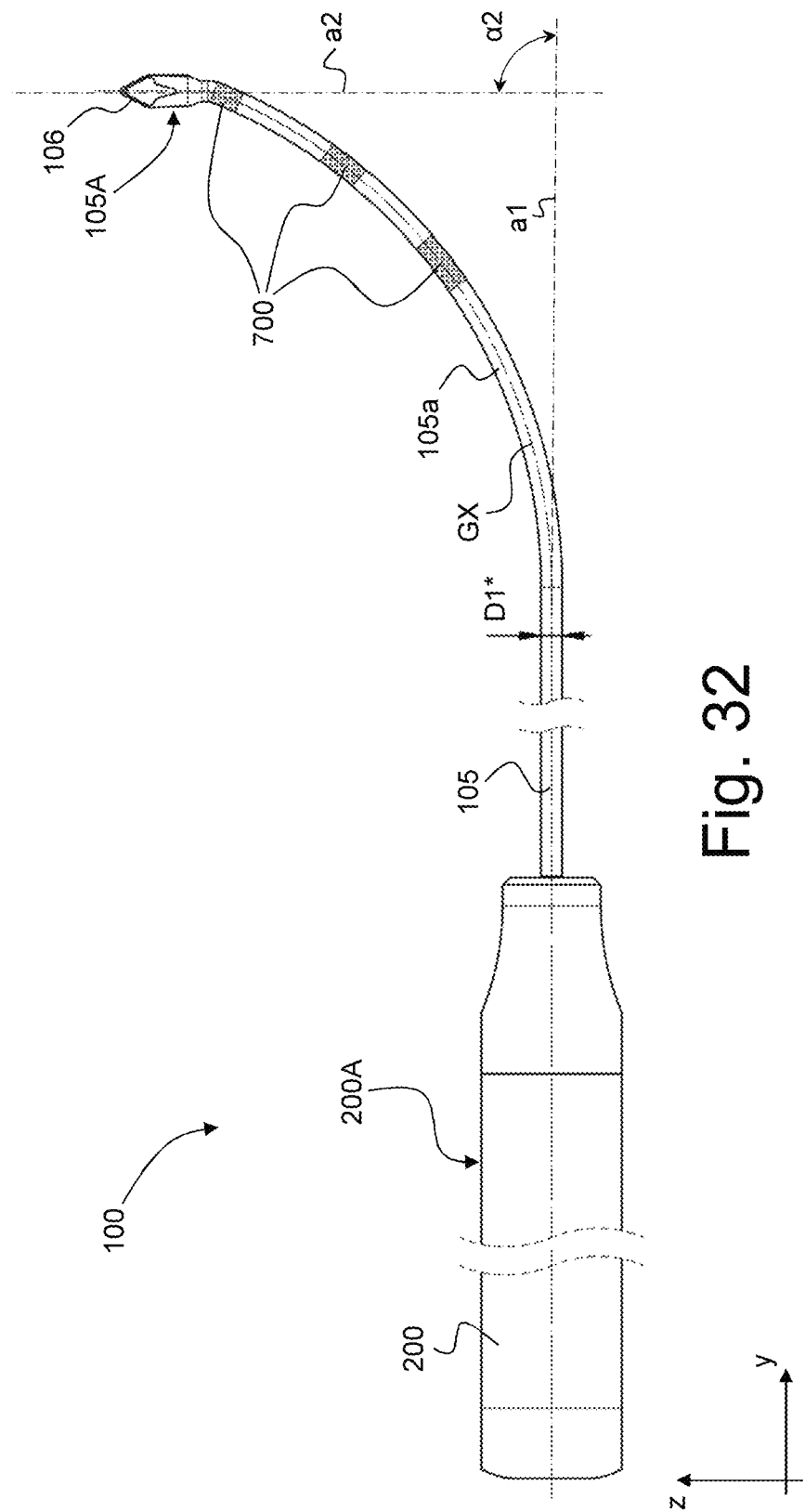
FIG. 32 is a side view of a medical instrument in accordance with a further embodiment of the invention, as seen along the x axis of a Cartesian coordinate system x-y-z, with the elongated rod member of the medical instrument extending substantially within a defined plane that is parallel to the vertical plane formed by the y and z axes.
Figure 33:
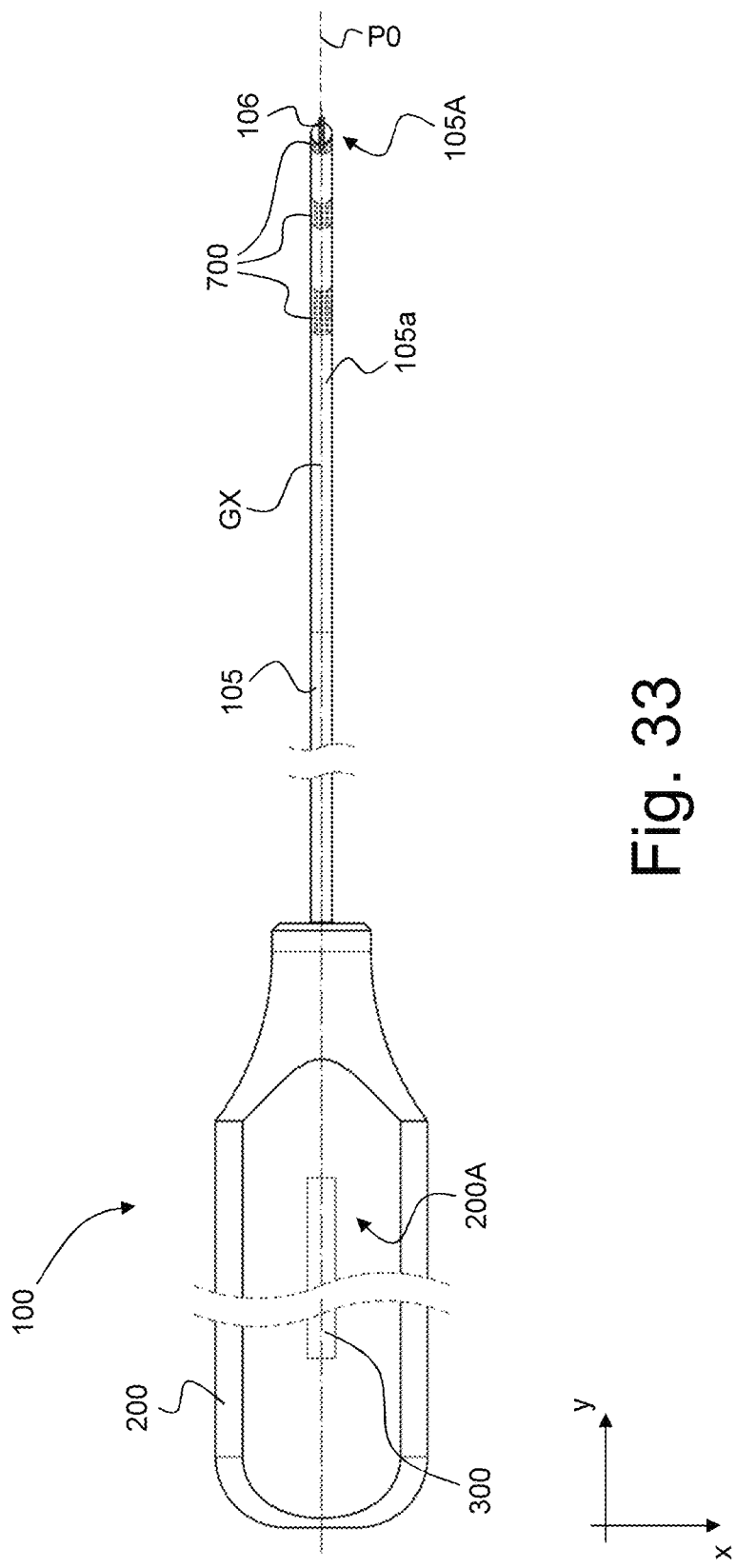
FIG. 33 is a top view of the medical instrument of FIG. 32 as seen along the z axis.
Figure 34:
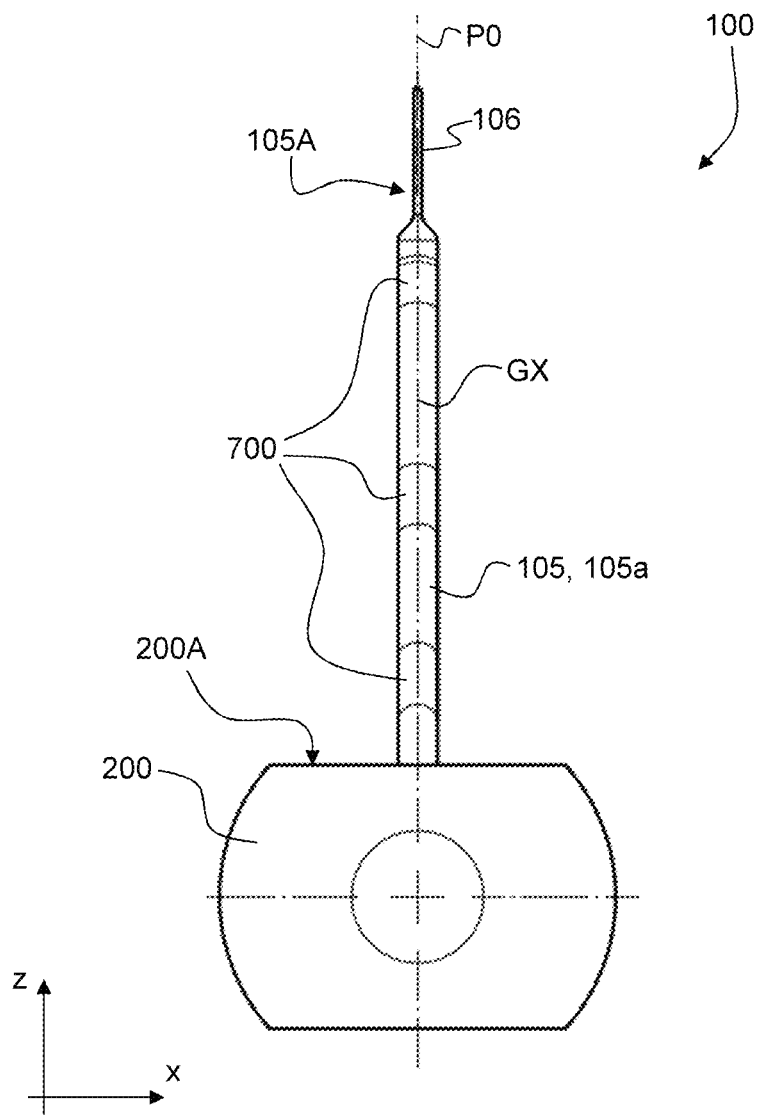
FIG. 34 is a rear view of the medical instrument of FIGS. 23 and 24 as seen along the y axis.

Referring more particularly to the first embodiment of FIGS. 1 to 10, to the variant of FIGS. 23 to 27, and to the embodiment of FIGS. 32 to 37A-C, one can note that an end section of the elongated rod member 5, 5* resp. 105, at the terminal end 5A, 5A*, resp. 105A, of the second portion, extends substantially perpendicularly to the first direction a1, namely along a second direction a2 that is parallel to the z axis. In other words, angle α2 depicted in FIGS. 3, 23 and 32 is substantially 90°.

In the illustrated examples, the second portion of the elongated rod member 5, 5*, resp. 105, includes a single curved section 5a, 5a*, resp. 105a, extending over an angle α1 (see FIG. 2 which applies by analogy to the variant of FIGS. 23 to 27 and to the embodiment of FIGS. 32 to 37A-C) that exceeds 60° and a radius of curvature R1 of the curved section 5a, 5a* resp. 105a, is of the order of 30 to 45 mm. By way of illustration, angle α1 and radius of curvature R1 can be selected to equal approximately 68° and 37 mm, respectively, which values are not to be considered as limiting the scope of the invention. In this instance, it may be appreciated that the end section of the elongated rod member 5, 5*, resp. 105, at the terminal end 5A, 5A*, resp. 105A, of the second portion, is bent with respect to the end of the curved section 5a, 5a*, resp. 105a, by an angle of approximately 20°, so that the end section extends substantially perpendicularly to the first direction a1.

The illustrated arc shape allows the instrument to be introduced under or against the structure to be released into the sonography field without any interference between the handle portion of the instrument and the sonography probe all over the procedure. This shape also allows to withdraw the instrument without risk of causing involuntary lesion to surrounding soft tissue.

By way of further illustration, a length L0 of handle portion 2, resp. 200, along the y axis can be of the order of 50 mm, while an overall length L1 of elongated rod member 5, 5*, resp. 105, along the y axis can be of the order of 90 mm. A length L2 of the end section, along the z axis, at the terminal end 5A, 5A*, resp. 105A of elongated rod member 5, 5*, resp. 105, can be of the order of 5 mm (or more).

Referring more particularly to the other embodiments of FIGS. 11 to 20, 28 to 31, and 38 to 43A-C, one can note that the second portion of the elongated rod member 50, 50*, resp. 150, includes a multiplicity of, namely three, curved sections 50a, 50b, 50c, 50a*, 50b*, 50c*, resp. 150a, 150b, 150c, each extending over an angle β1, β2, resp. β3 (see FIG. 12 which applies by analogy to the variant of FIGS. 28 to 31 and to the embodiment of FIGS. 39 to 43A-C) that does not exceed 40°. By way of illustration, angles β1, β2, and β3 can be selected to equal approximately 35°, which value is once again not to be considered as limiting the scope of the invention.

In accordance with this other embodiment, the three curved sections 50a, 50b, 50c, 50a*, 50b*, 50c*, resp. 150a, 150b, 150c, are separated by two substantially rectilinear sections having a length L2', L2, resp. L3', L3 of the order of 15 to 25 mm. By way of illustration, lengths L2', L2 and L3', L3 are respectively of 22 mm and 17 mm.

By way of further illustration, a length L0' of handle portion 20, resp. 200*, along the y axis can be of the order of 25 to 35 mm, while a length L1' of the first, rectilinear portion of elongated rod member 50, 50*, resp. 150, can be of the order of 30 mm. A length L4', L4** of the end section, at the terminal end 50A, 50A*, resp. 150A, of elongated rod member 50, 50*, resp. 150, can likewise be of the order of 5 mm (or less). In the variant of FIGS. 28 to 31, such length L4' can for instance be reduced to approximately 2 to 3 mm.

Figure 13:
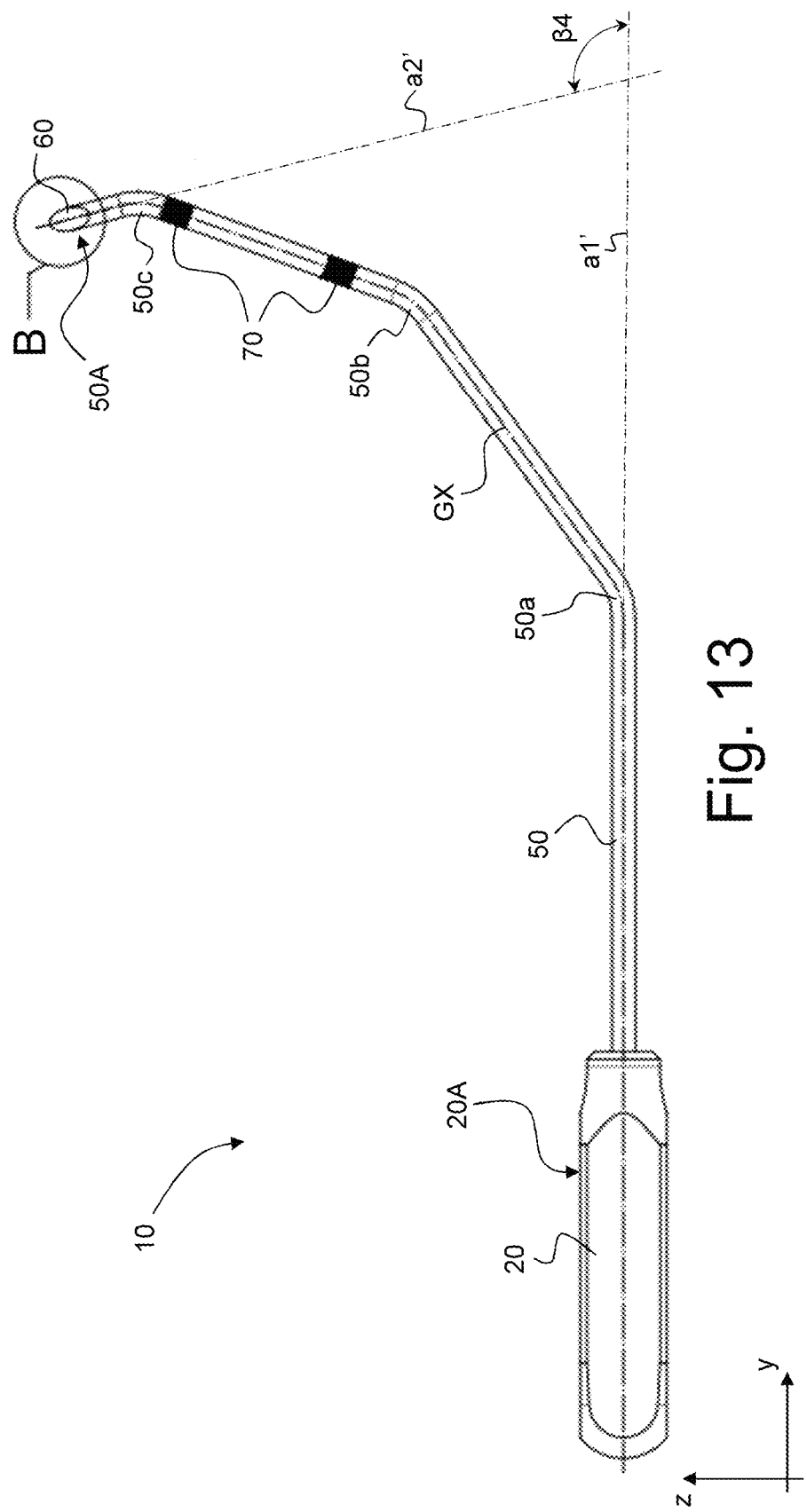
FIG. 13 is another side view of the medical instrument of FIG. 11 as seen along the x axis.
Figure 14:
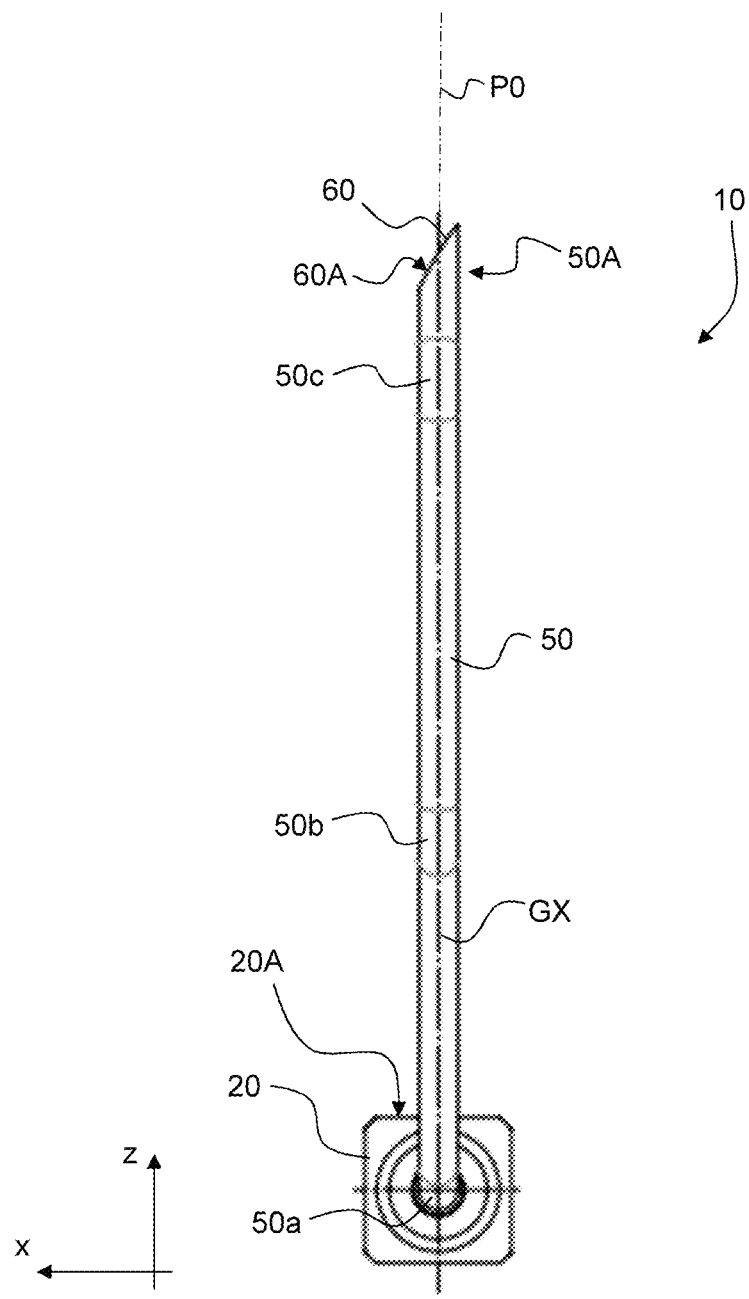
FIG. 14 is a front view of the medical instrument of FIG. 11 as seen along the y axis.
Figure 15:
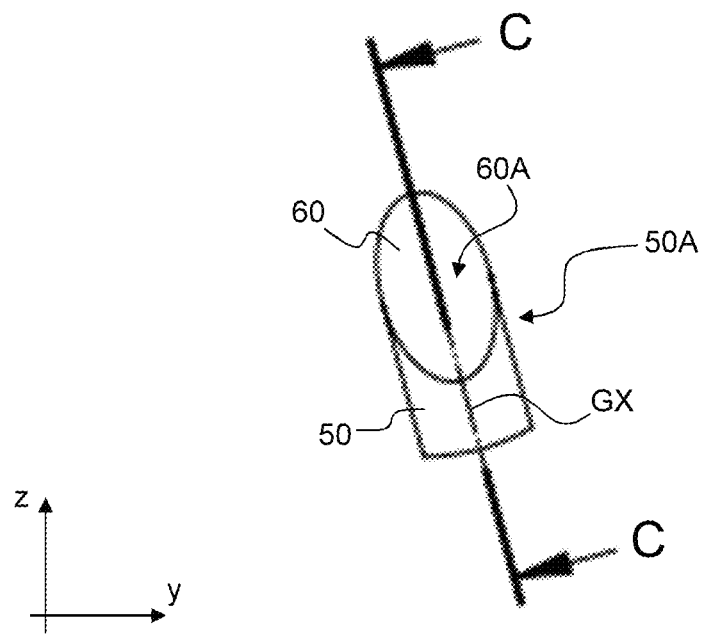
FIG. 15 is an enlarged view of a terminal end of the medical instrument of FIG. 11 as identified by detail B in FIG. 13.
Figure 16:
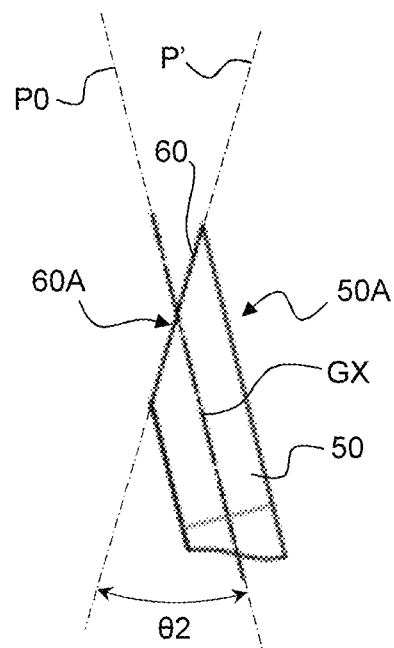
FIG. 16 is a cross-sectional view of the terminal end of the medical instrument of FIG. 11 as taken along sectional plane C-C reproduced in FIG. 15.
Figure 17:
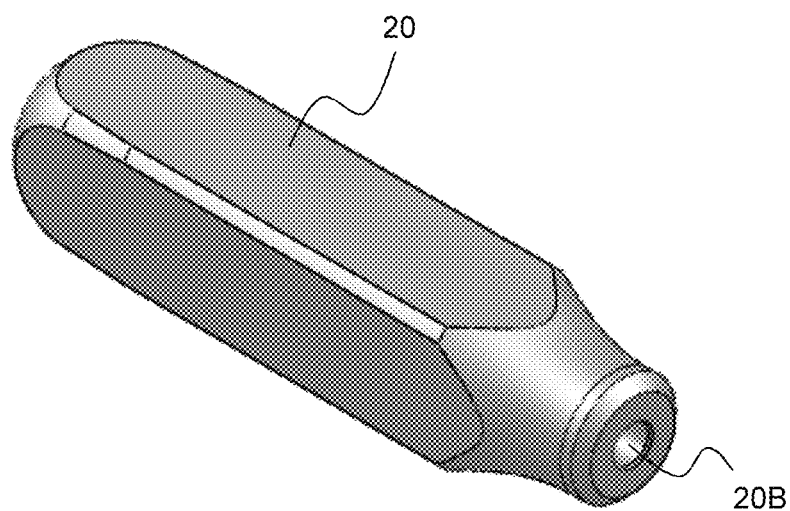
FIG. 17 is a perspective view of a handle portion of the medical instrument of FIG. 11.
Figure 18:
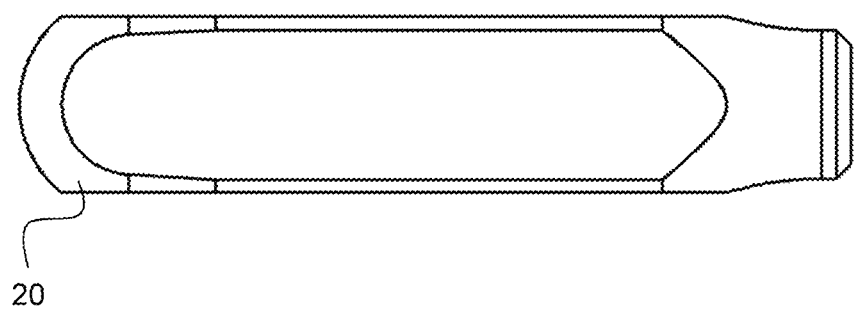
FIG. 18 is a side view of the handle portion of FIG. 17.
Figure 19:
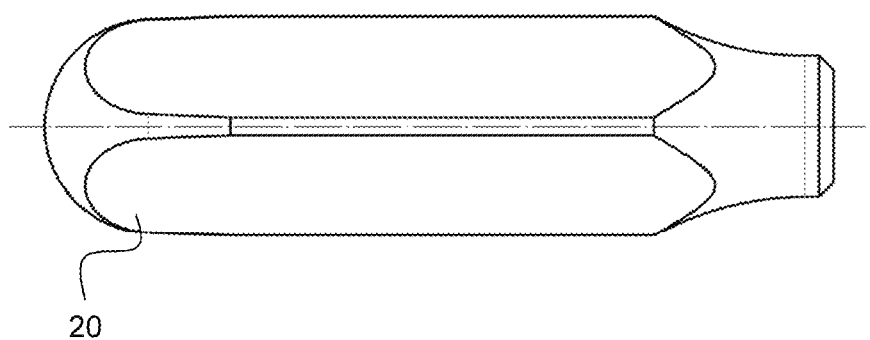
FIG. 19 is another side view of the handle portion of FIG. 17 taken from a different perspective.
Figure 20:
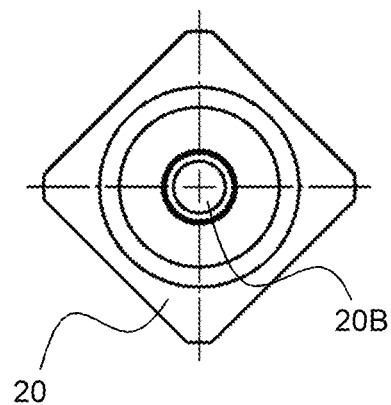
FIG. 20 is a front view of the handle portion of FIG. 17 where the handle portion is secured to the elongated rod member of the medical instrument.
Figure 21A:
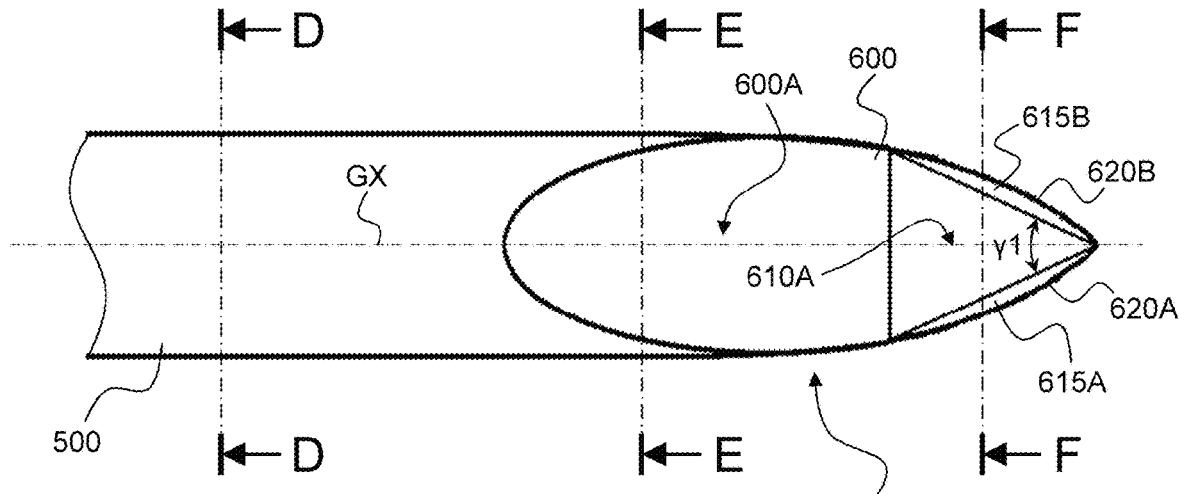
FIG. 21A is a top view of a terminal end of a medical instrument showing a configuration of the bevelled end of the medical instrument in accordance with another embodiment of the present invention, which configuration is also applicable in the context of the medical instruments of FIGS. 1 to 20.
Figure 21B:
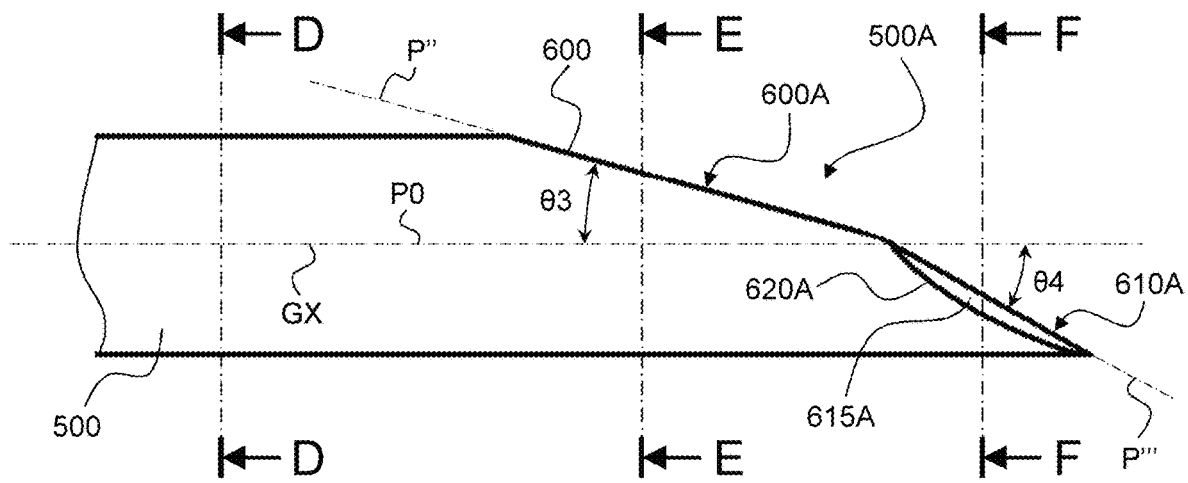
FIG. 21B is a side view showing the configuration of the bevelled end of the medical instrument of FIG. 21A.
Figure 38:
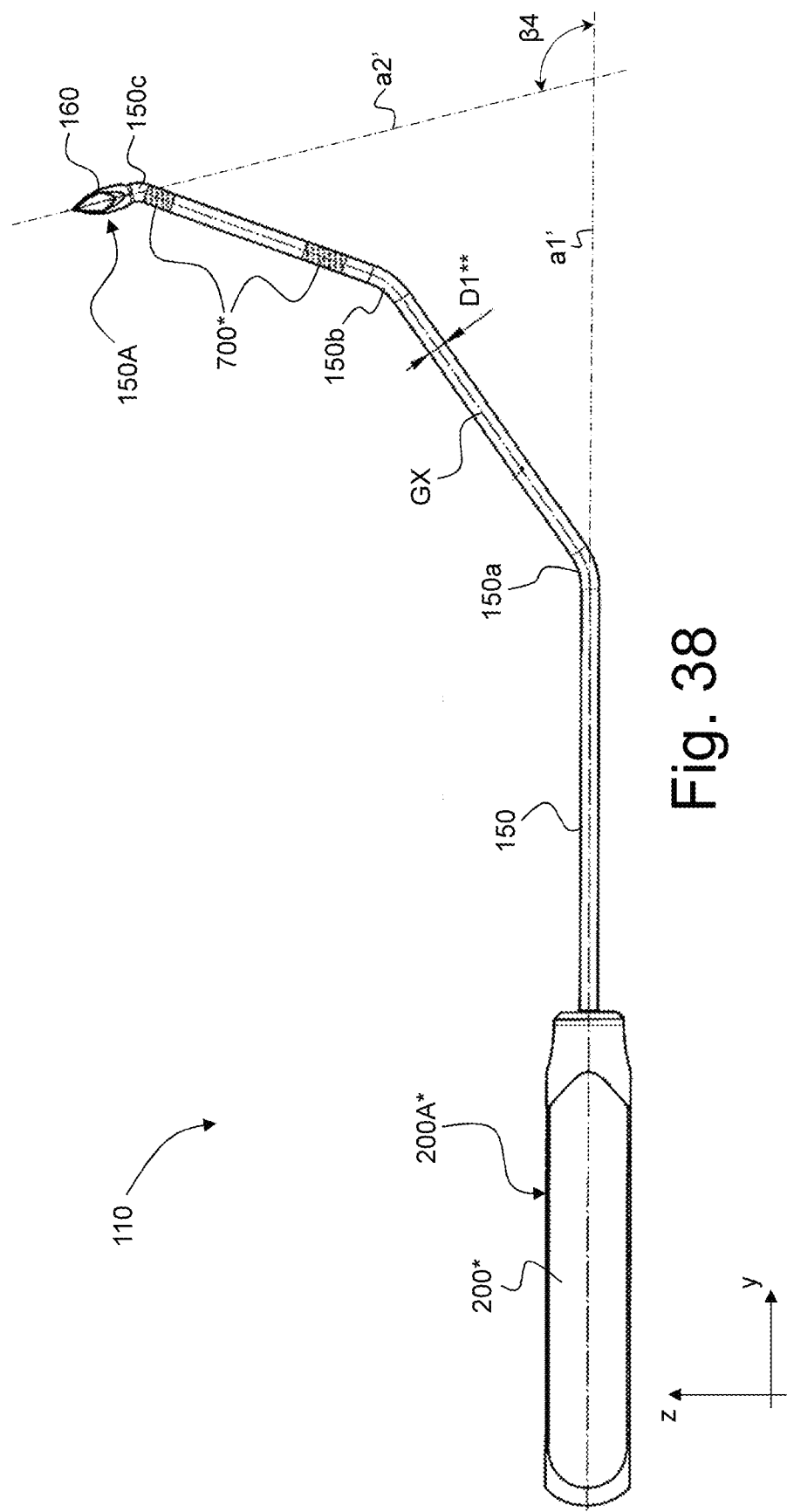
FIG. 38 is a side view of a medical instrument in accordance with yet another embodiment of the invention, as seen along the x axis of a Cartesian coordinate system x-y-z, with the elongated rod member of the medical instrument extending substantially within a defined plane that is parallel to the vertical plane formed by the y and z axes.
Figure 39:
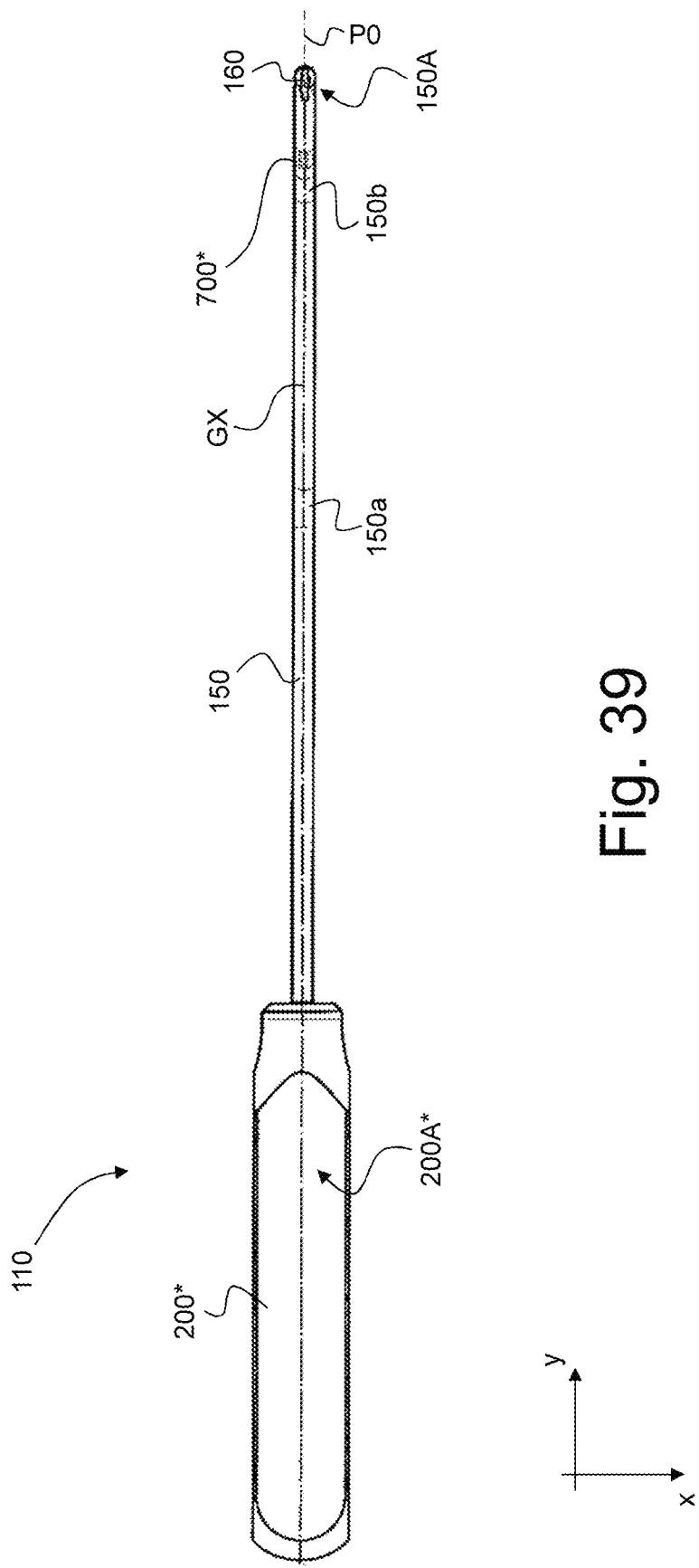
FIG. 39 is a top view of the medical instrument of FIG. 38 as seen along the z axis.
Figure 40:
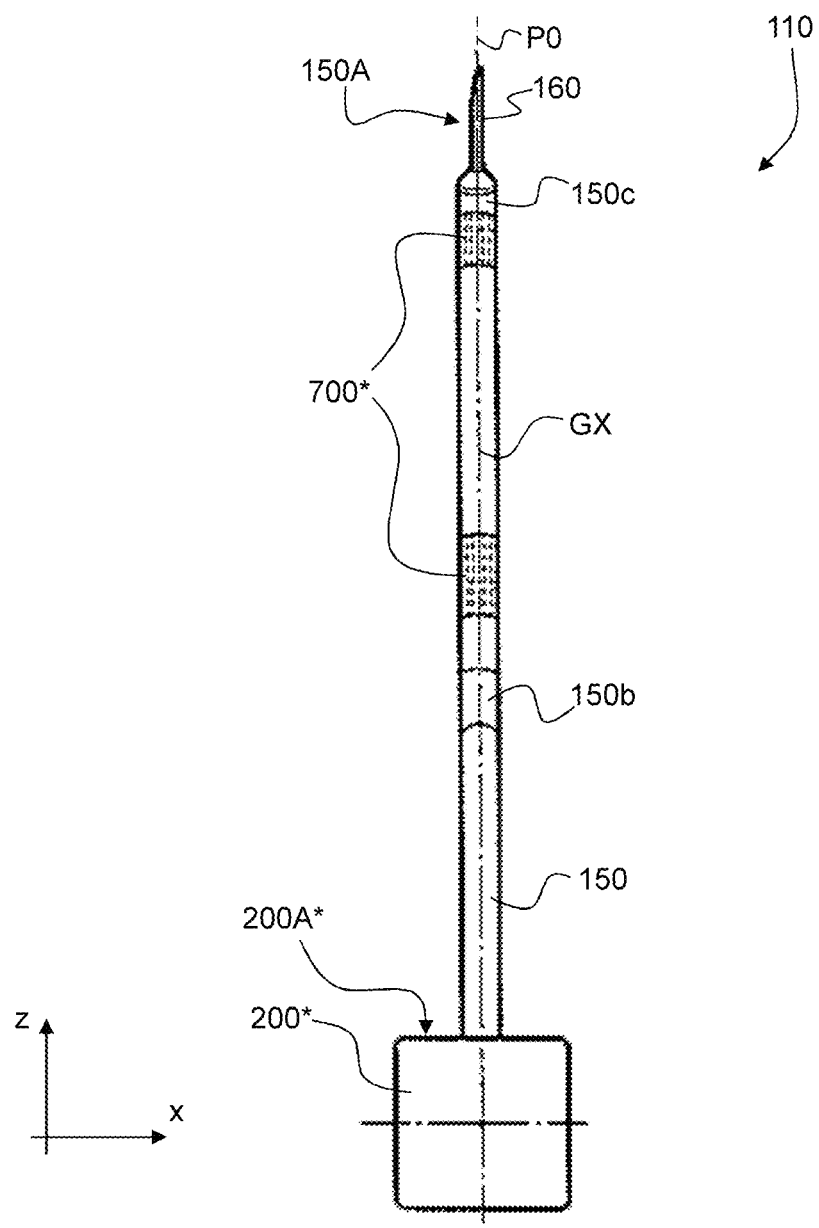
FIG. 40 is a rear view of the medical instrument of FIGS. 38 and 39 as seen along the y axis.

With regard to the embodiments of FIGS. 11 to 20, 28 to 31, and 38 to 43A-C, one can note that the end section of the elongated rod member 50, 50*, resp. 150, at the terminal end 50A, 50A*, resp. 150A, of the second portion, extends along the second direction a2' substantially perpendicularly to the first direction a1', however with an angle β4, as depicted in FIGS. 13, 28 and 38, that is of approximately 105° in the present instance.

The illustrated angled shape similarly allows the instrument to be introduced under or against the structure to be released into the sonography field without any interference between the handle portion of the instrument and the sonography probe all over the procedure. This shape likewise also allows to withdraw the instrument without risk of causing involuntary lesion to surrounding soft tissue.

By way of preference, the elongated rod member is provided with a plurality of markings that are designed to be distinguishable under sonography. Such markings are illustrated for instance in FIGS. 2 to 5, 13, 23 to 25, 28, 29, and 32 to 43A-C, and are identified by reference numerals 7, 70, 7*, 70*, 700 and 700*, respectively. These markings 7, 70, 7*, 70*, 700, resp. 700*, can in particular be embossings and can conveniently be distributed over the second portion of the elongated rod member 5, 50, 5*, 50*, 105, resp. 150, thus allowing the surgeon to precisely monitor the position of the medical instrument when performing percutaneous release procedures under the assistance of a sonography. Alignment of the markings 7, 70, 7*, 70*, 700, resp. 700*, in the sonography field with respect to the sonography probe in particular allows to ensure a proper and precise orientation of the medical instrument in the area to be treated. In that context, it could in particular be contemplated to use the relevant markings 7, 70, 7*, 70*, 700, resp. 700*, to automatically locate and detect the orientation of the medical instrument in the sonographic imagery, and provide visual assistance to the surgeon. This visual assistance could furthermore include the superimposition in real time of a virtual representation of the medical instrument on the sonographic imagery, if need be.

By way of preference, as schematically illustrated in FIGS. 23 to 25, 28, 29, and 32 to 43A-C, the dimensions and/or distribution of the markings 7*, 70*, 700, resp. 700*, along the elongated rod member 5*, 50*, 105, resp. 150, could be non-uniform, to facilitate identification of the relevant orientation of the medical instrument under sonography.

Advantageously, as illustrated in FIGS. 1 to 10 (see also FIGS. 23 to 27), a visible marking 3 (such as a laser marking) may be provided on the handle portion 2 to likewise identify an orientation of the medical instrument when performing surgery. A similar visual marking 300 is provided in the context of the embodiment of FIGS. 32 to 37A-C. This visible marking 3, resp. 300, may in particular be provided on an inner face 2A, resp. 200A, of the handle portion 2, resp. 200, which is oriented in a same direction as the second portion of the elongated rod member 5, 5*, resp. 105. While not specifically illustrated in FIGS. 11 to 20, 28 to 31, and 38 to 43A-C, a similar visible marking may be provided on the inner face 20A, resp. 200A\*, of the handle portion 20, resp. 200\*, of medical instrument 10, 10\*, resp. 110.

By way of preference, the elongated rod member **5, 50, 500, 5\*, 50\*, 105, resp. 150, has a substantially circular cross-section upstream of the terminal end 5A, 50A, 500A, 5A, 50A, 105A, resp. 150A. A diameter D1, D1, D1\*, resp. D1\*\*, of the elongated rod member 5, 50, 500, 5\*, 50\*, 105, resp. 150, may in particular be of the order of 1 to 2 mm. By way of illustration, diameter D1, resp. D1\*, of elongated rod member 5, 5\*, resp. 105, is of the order of 1.5 mm, while diameter resp. D1\*\*, of elongated rod member 50, 50\*, resp. 150**, is of the order of 1.3 mm.

In the illustrations of FIGS. 1 to 31, one may appreciate that the elongated rod member 5, 50, 500, 5\*, resp. 50\*, is shown as being solid and non-hollow. One may however possibly contemplate to use a hollow rod member instead (similar to the embodiments discussed with reference to FIGS. 32 to 43A-C), which would provide for the ability to detect a possible bleeding through the relevant rod cavity, in case of damage to a blood vessel, and/or to inject a local anaesthetic using a dedicated syringe inserted in the relevant rod cavity. In this case, it is advantageous to further adapt the handle of the medical instrument to likewise exhibit a corresponding cavity communicating with the rod cavity to e.g. allow injection of the local anaesthetic. The use of a solid and non-hollow rod member however remains particularly advantageous in the context of the embodiments discussed with reference to FIGS. 1 to 31 in that the medical instrument is simpler and more cost-efficient to produce.

In the context of the embodiments of FIGS. 32 to 43A-C, the elongated rod member 105, resp. 150, preferably includes a hollow tube member as discussed above, which facilitates formation of the flattened section 106, resp. 160, as such flattened section can simply be produced by crushing the free end of the hollow tube member 105.1, resp. 150.1. This being said, a solid and non-hollow rod member could still be contemplated.

The medical instrument of the invention can in particular be used for the purpose of performing percutaneous release procedures on upper or lower limbs, especially under the assistance of a sonography. Other uses could however be contemplated.

Surgical release of the transverse carpal ligament (TCL) using e.g. the medical instrument 1, 1\* or 100 as discussed above is in essence carried out as follows:

1. Installation of the Patient

The patient is in supine position, with the arm placed on a lateral table. After disinfection of the arm, from fingertips towards the elbow, sterile drapes are placed. Sterile sonographic gel and cover for the sonography probe are used. The procedure begins with the sonography probe placed on the heel of the patient's hand. Different anatomical structures are identified in coronal and sagittal planes: flexor tendons, radial artery, ulnar artery, superficial volar arch, median and ulnar nerves, median motor branch and Berrettini branch if present. The flexor retinaculum (transverse carpal ligament—TCL) is identified as well. All potential structures that could contraindicate the percutaneous release are ruled out (intraductal mass, ectopic muscle or artery, etc.).

2. Local Anaesthesia

Under sonography guidance, a 18 Gauge needle is introduced 1 cm proximal to the volar wrist crease between the ulnar artery and the median nerve. Care is taken to avoid entering the Guyon canal. 3 ml of xylocaine are injected under sonography guidance into the carpal tunnel, and 3 ml of xylocaine is further injected subcutaneously above the TCL from its proximal border to its distal border. The latter injection may be slightly painful.

3. Making of the Entry Point for the Instrument

A 14 Gauge needle is introduced through the same skin entry point with a 35° inclination angle in the sagittal plane and through the volar carpal ligament up to the carpal tunnel, between the ulnar artery and the median nerve. Once in the carpal tunnel, the tip of the needle is accurately identified by slightly rotating its bevel.

The 14 Gauge needle is then withdrawn, and a rounded end probe is introduced through the entry point to the carpal tunnel. The probe allows to palpate the TCL from its proximal to its distal border, defining the pathway of future section. The probe is placed just lateral to the hook of the hamate. The probe cannot pass from the carpal tunnel to the subcutaneous plane. During this step, the sonography probe is placed alternately longitudinally and transversally, to obtain long and axial views.

4. Insertion of the Instrument Through the Entry Point

Figure 44A:
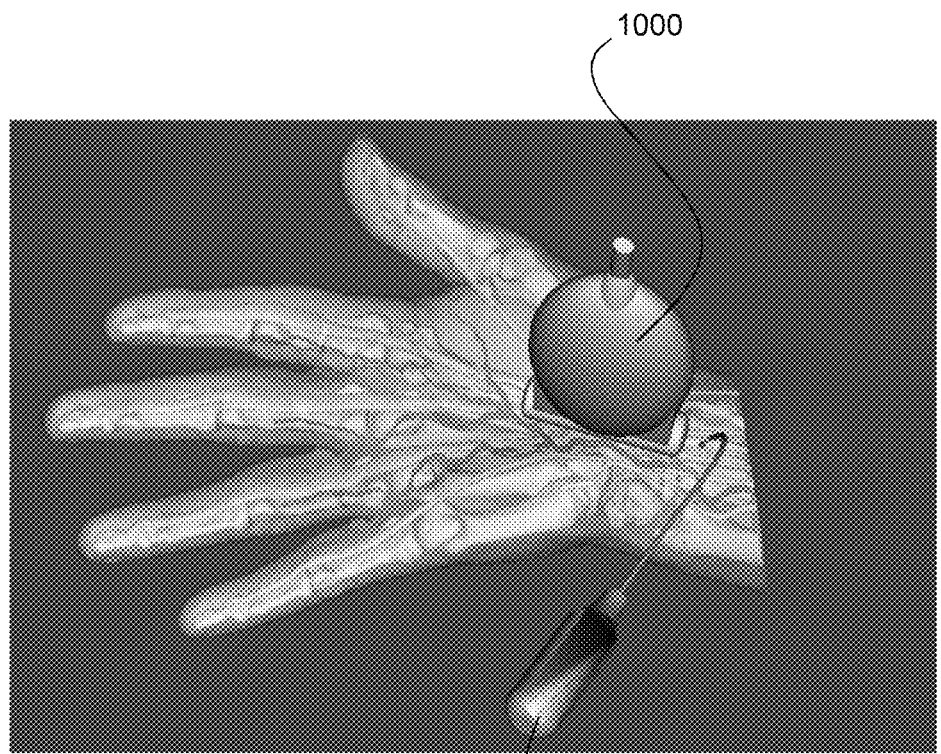
FIGS. 44A and 44B are schematic illustrations showing the medical instrument of FIGS. 32 to 37A-C being used under sonography guidance for release of the transverse carpal ligament (TCL), prior to insertion of the instrument.
Figure 44B:
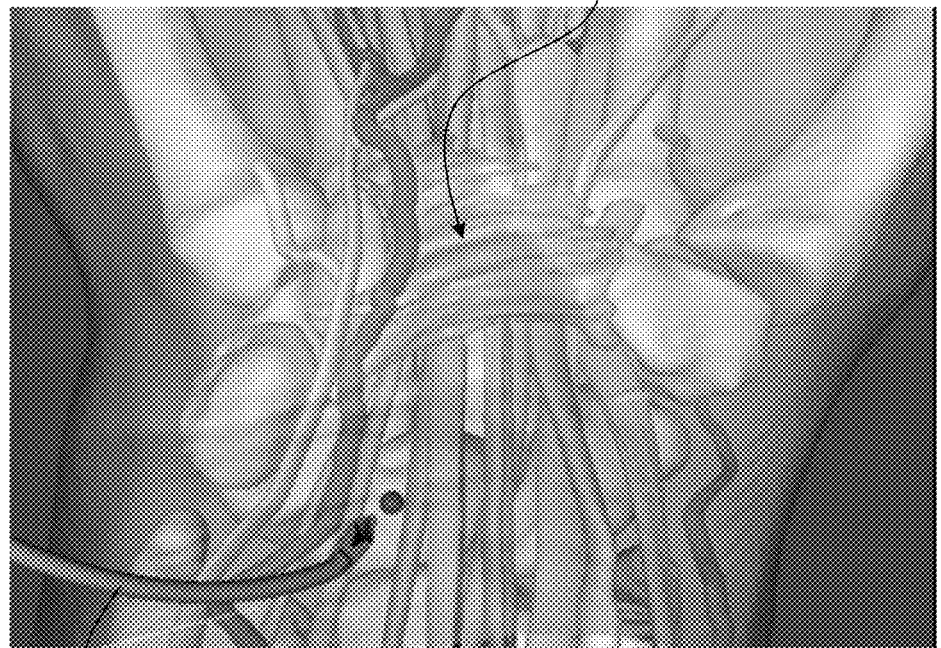

Keeping the longitudinal view, the rounded end probe is withdrawn, and the aforementioned medical instrument (also referred to as Carpal Tunnel release Sono-Instrument, or CTrSI) is introduced through the entry point, under sonography control. In the illustrated example as shown in FIGS. 44A and 44B, medical instrument 100 is used and is introduced first with the flattened section 106 oriented volarly, with the leading edge 106A oriented substantially parallel to the TCL plane.

Figure 45A:
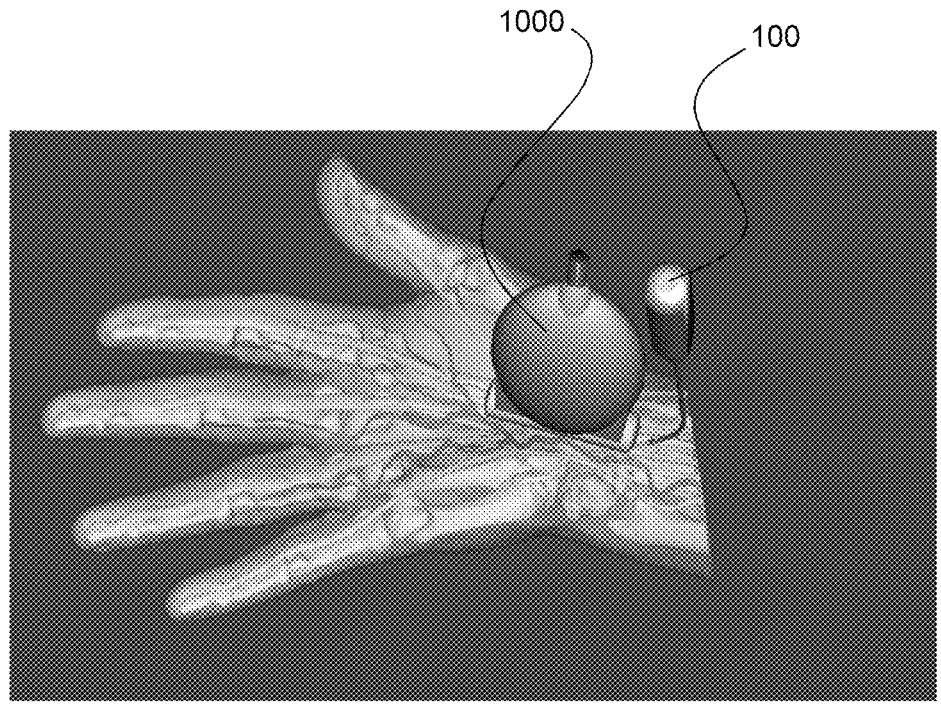
FIGS. 45A and 45B are schematic illustrations showing the medical instrument of FIGS. 32 to 37A-C during insertion of the instrument.
Figure 45B:
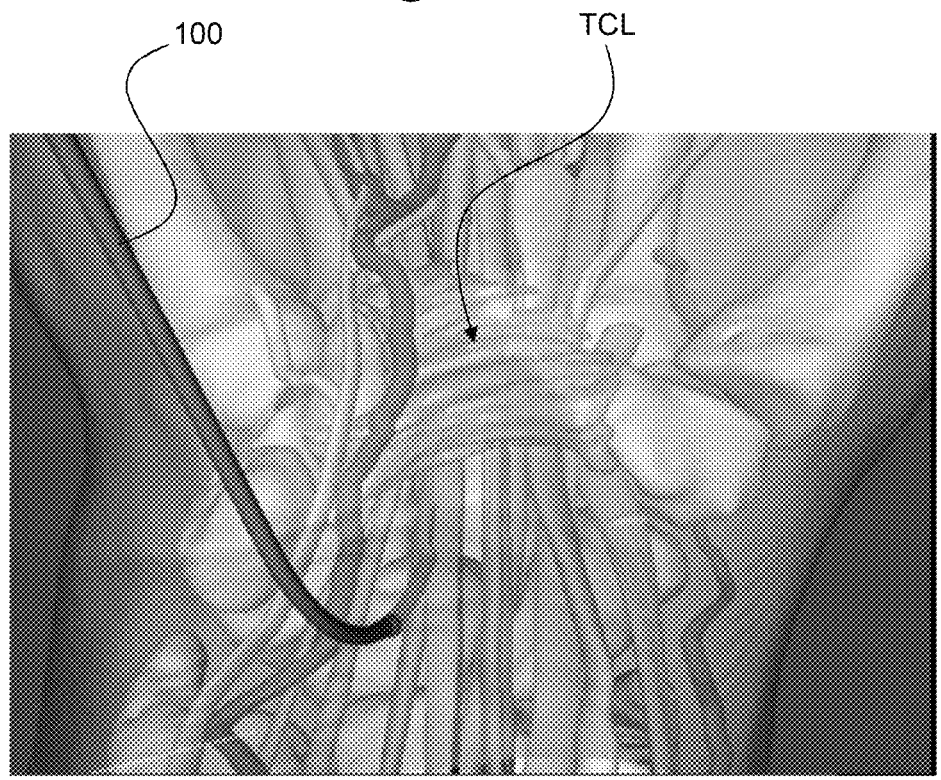

Once the tip of the medical instrument 100 is passed through the volar carpal ligament, a 90° clockwise rotation of the instrument 100 is performed, allowing to turn the flattened section 106 and leading edge 106A of the instrument 100 in the sagittal plane, substantially perpendicular to the TCL plane, as schematically illustrated by FIGS. 45A and 45B.

5. Section of the Transverse Carpal Ligament (TCL)

Figure 46A:
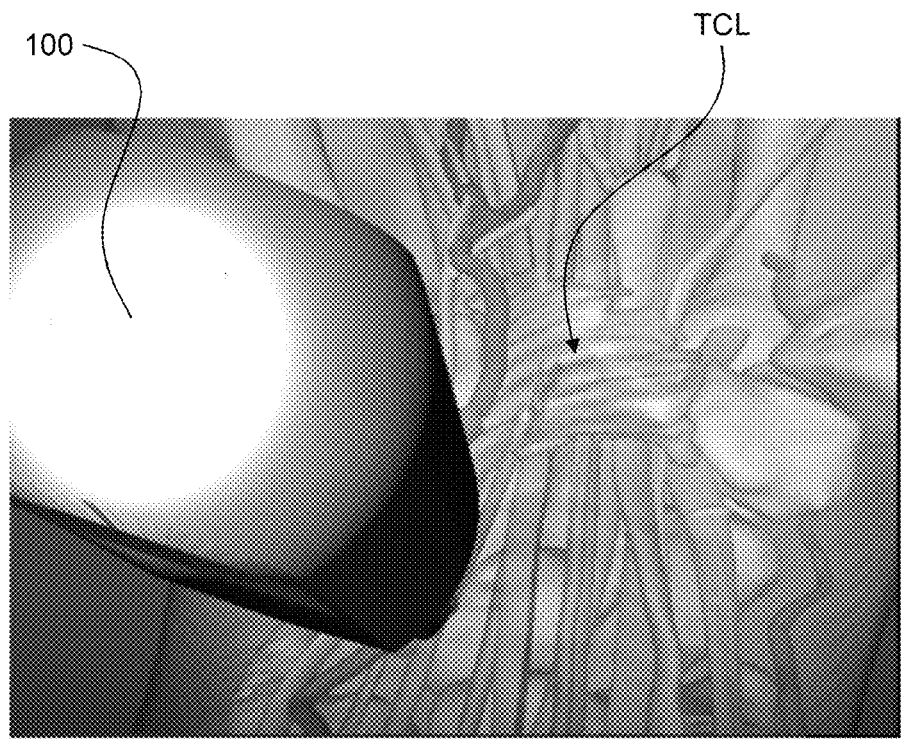
FIGS. 46A to 46C are schematic illustrations showing the medical instrument of FIGS. 32 to 37A-C during section of the TCL.
Figure 46B:
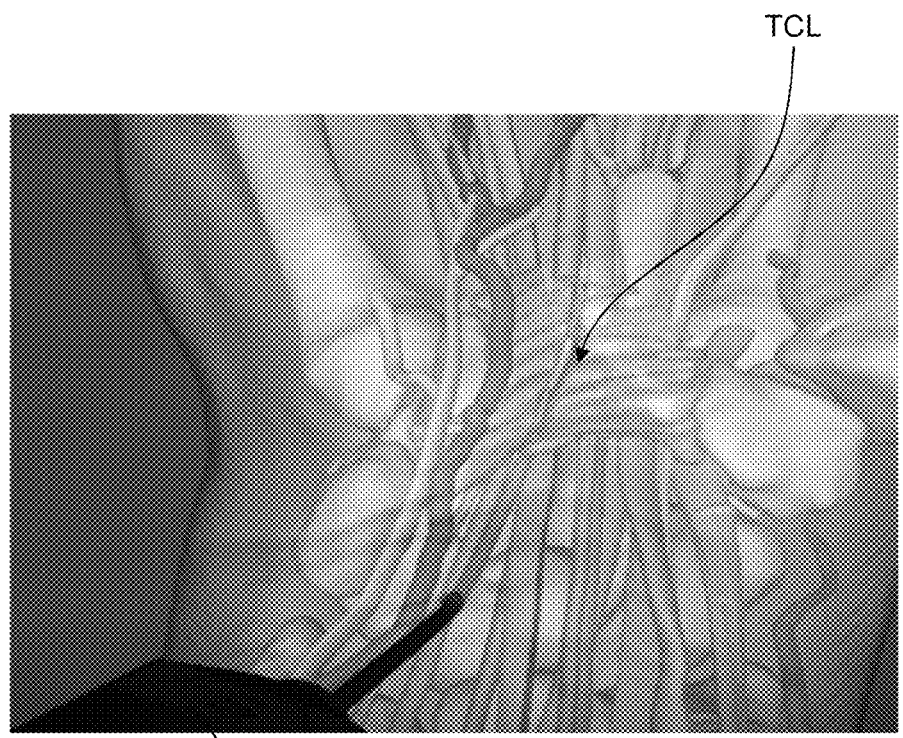
Figure 46C:
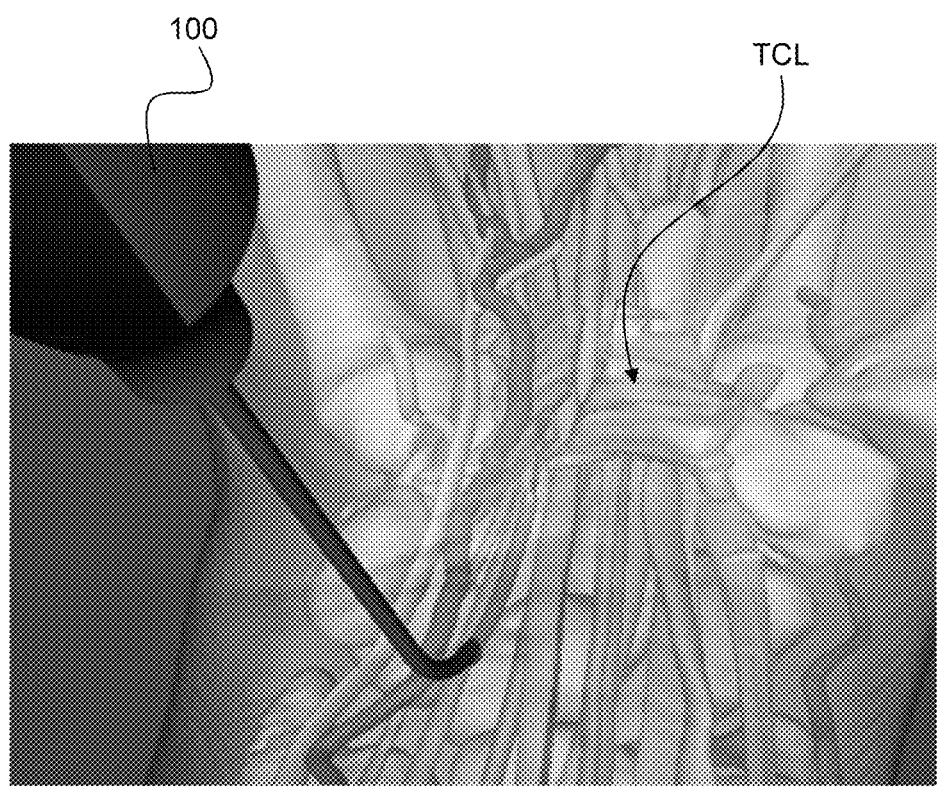

The proximal part of the volar carpal ligament is first addressed and progressively cut in an anterograde manner. Each millimetre, the tip of leading edge 106A is introduced between the tendons and the TCL doing crocheting movements. The TCL is then progressively cut in the same anterograde manner by handling of the instrument 100 to induce an oscillating motion to its leading edge 106A from the dorsal to volar part of the TCL, as schematically illustrated by FIGS. 46A to 46C.

Figure 47:
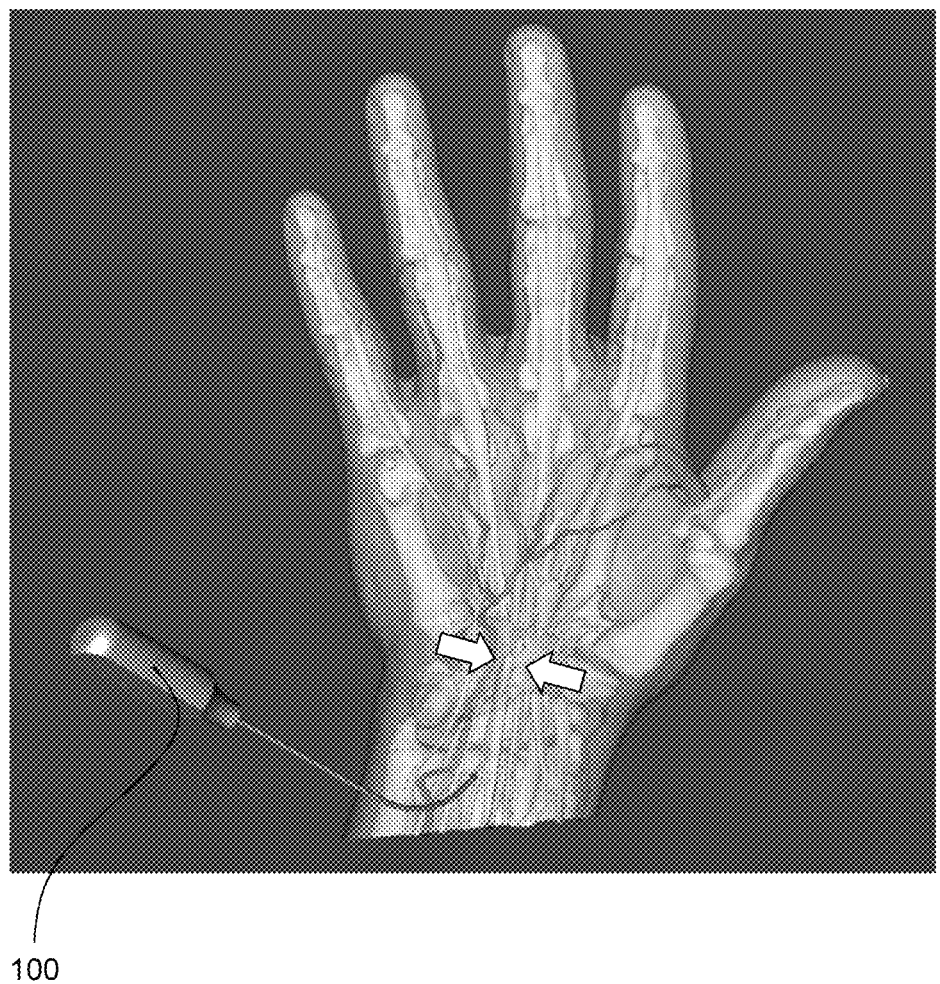
FIG. 47 is a schematic illustration showing withdrawal of the instrument of FIGS. 32 to 37A-C following completion of the release of the TCL.

At the beginning of the TCL release, a crack sound may be heard, depending on the TCL stiffness. The release is performed at the safe zone level that is located just laterally to the hook of the hamate, with constant sonographic control of the ulnar artery location and the median nerve, medially and laterally, respectively. The section of the TCL is performed quite obliquely, from dorsal to volar and from medial to lateral. All over the procedure, short axial views are regularly performed to control the position of the instrument 100. The distal border of the TCL is released with great care because of the close vicinity of the volar superficial carpal arch, by identifying accurately the instrument tip and the arch with the sonographic probe. At the end of the procedure, the tip of the instrument 100 is used as a hook to evaluate completion of the release. FIG. 47 schematically illustrates withdrawal of the instrument 100 following completion of the release of the TCL.

6. Confirmation That the Release is Complete

The instrument 100 is withdrawn and the rounded end probe is introduced again, to palpate the remains of the TCL and confirm that the release is complete, which can be verified by observing that the probe can be displaced, from the carpal tunnel to the subcutaneous plane, without any resistance.

7. Postoperative Care

A compressive dressing is made, at the site of introduction and over the carpal tunnel. This dressing is entirely removed, twelve hours after the procedure, and no more dressing is then needed. The patient is allowed to do all his/her daily activities without any limitation, the day after the procedure. During the first ten days after the procedure, the patient is advised to wear a sling when the hand is not used, and to move actively the fingers to prevent finger swelling and possible complex regional pain syndrome (CRPS).

Surgical release of the A1 pulley using e.g. the medical instrument 10, 10* or 110 as discussed above is in essence carried out as follows:

1. Installation of the Patient

The patient is in supine position, with the arm placed on a lateral table. After disinfection of the arm, from fingertips towards the elbow, sterile drapes are placed. Sterile sonographic gel and cover for the sonography probe are used. The procedure begins with the sonography probe placed on the palm just proximal to the metacarpophalangeal (MCP) joint. Different anatomical structures are identified in coronal and sagittal planes: flexor tendon(s), digital collateral nerves and arteries, digital pulleys. In particular, the A1 pulley is identified, and its thickness measured.

2. Local Anaesthesia

A 22 Gauge bent needle is introduced just distal to the MCP skin crease and 2 to 3 ml of xylocaine are injected under sonography guidance, above the A1 pulley and inside the digital canal. The patient is then asked to fully flex his/her finger in order to observe the triggering phenomenon, the gliding of the tendon(s) and the finger's joint range of motion (ROM). Once pain has been eliminated, it is frequent to better observe the triggering and the irregular tendon gliding compared to when the patient is not anesthetized.

3. Making of the Entry Point for the Instrument

A 14 Gauge needle is introduced through the same skin entry point and through the digital canal, just distally to the A1 pulley. The tip of the needle is accurately identified by slightly rotating its bevel.

4. Insertion of the Instrument Through the Entry Point

Figure 48A:
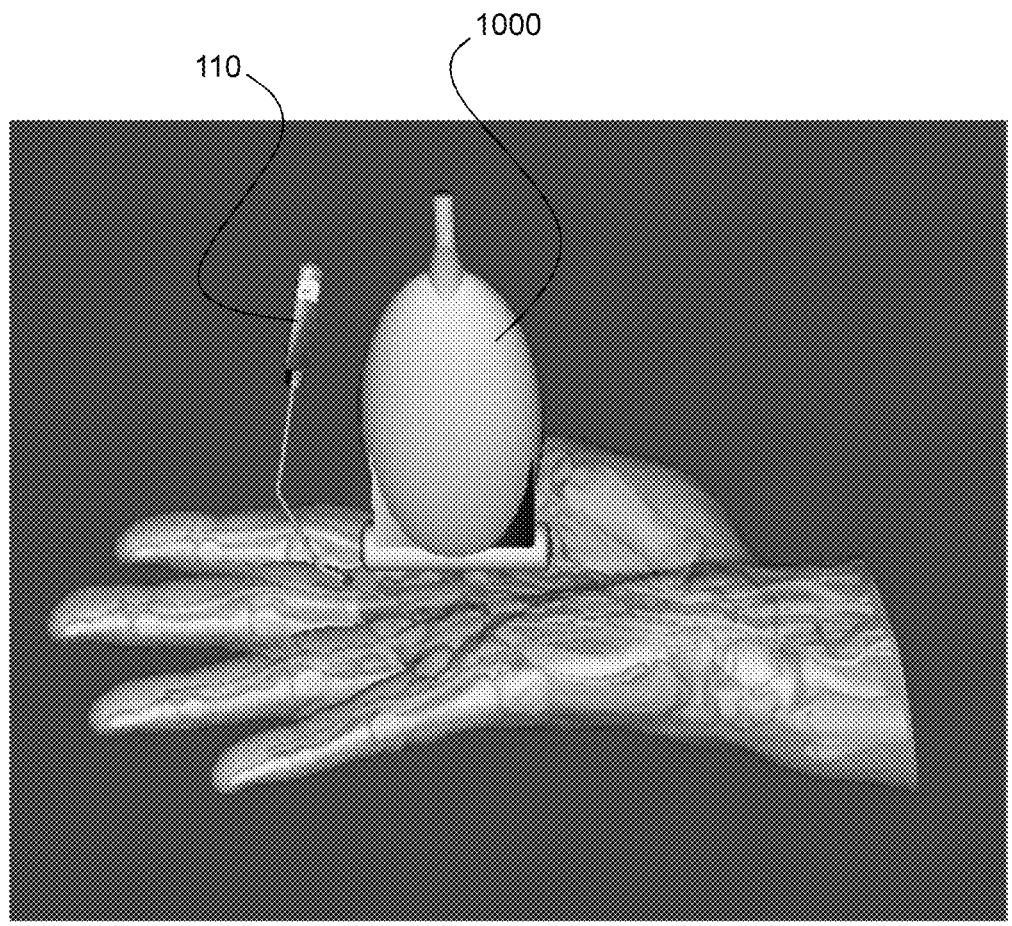
FIGS. 48A and 48B are schematic illustrations showing the medical instrument of FIGS. 39 to 43A-C being used under sonography guidance for release of the A1 pulley, during insertion of the instrument.

The 14 Gauge needle is withdrawn and the aforementioned medical instrument (also referred to as Trigger Finger release Sono-Instrument, or TFrSI) is introduced through the same entry point, under sonography control. In the illustrated example as shown in FIG. 48A, medical instrument 110 is used and is introduced first with the flattened section 160 oriented volarly, with the leading edge 160A oriented substantially parallel to the volar plane of the pulley.

Figure 48B:
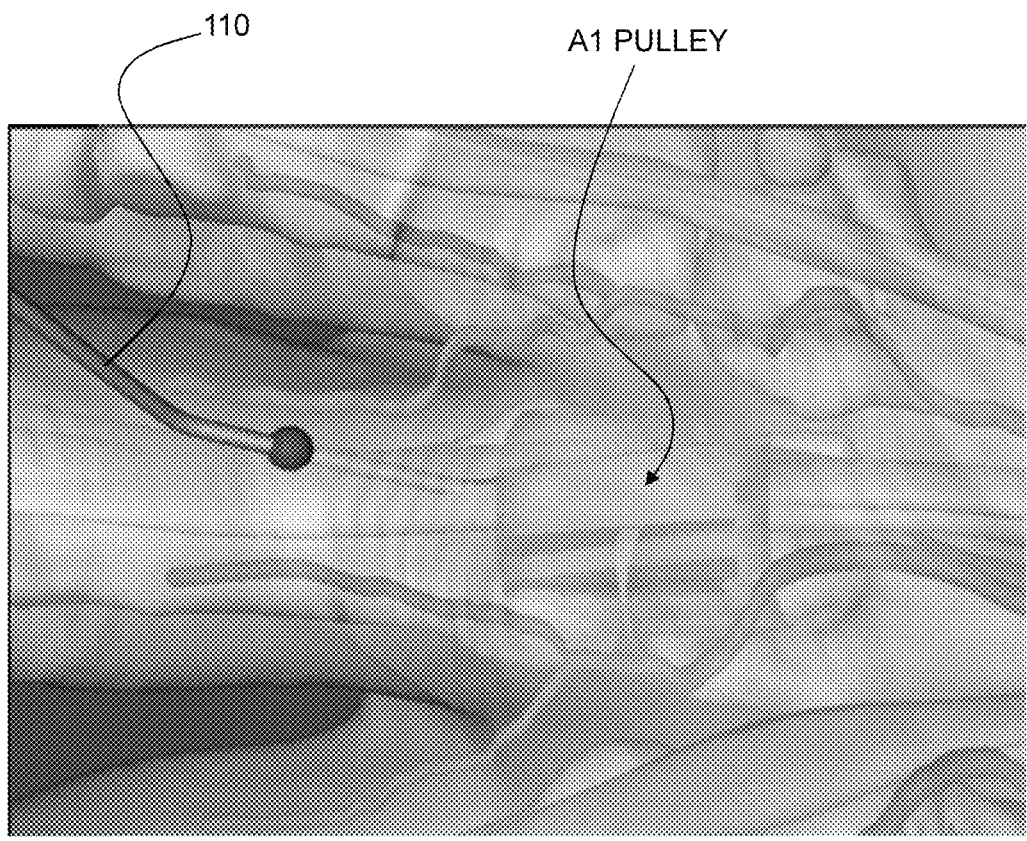

When the tip of the instrument 110 arrives against the A1 pulley, a 90° clockwise rotation of the instrument 110 is performed, allowing to turn the flattened section 160 and leading edge 160A of the instrument 110 in the sagittal plane, substantially perpendicular to the volar plane of the A1 pulley, as schematically illustrated by FIG. 48B.

5. Section of the A1 Pulley

Figure 49A:
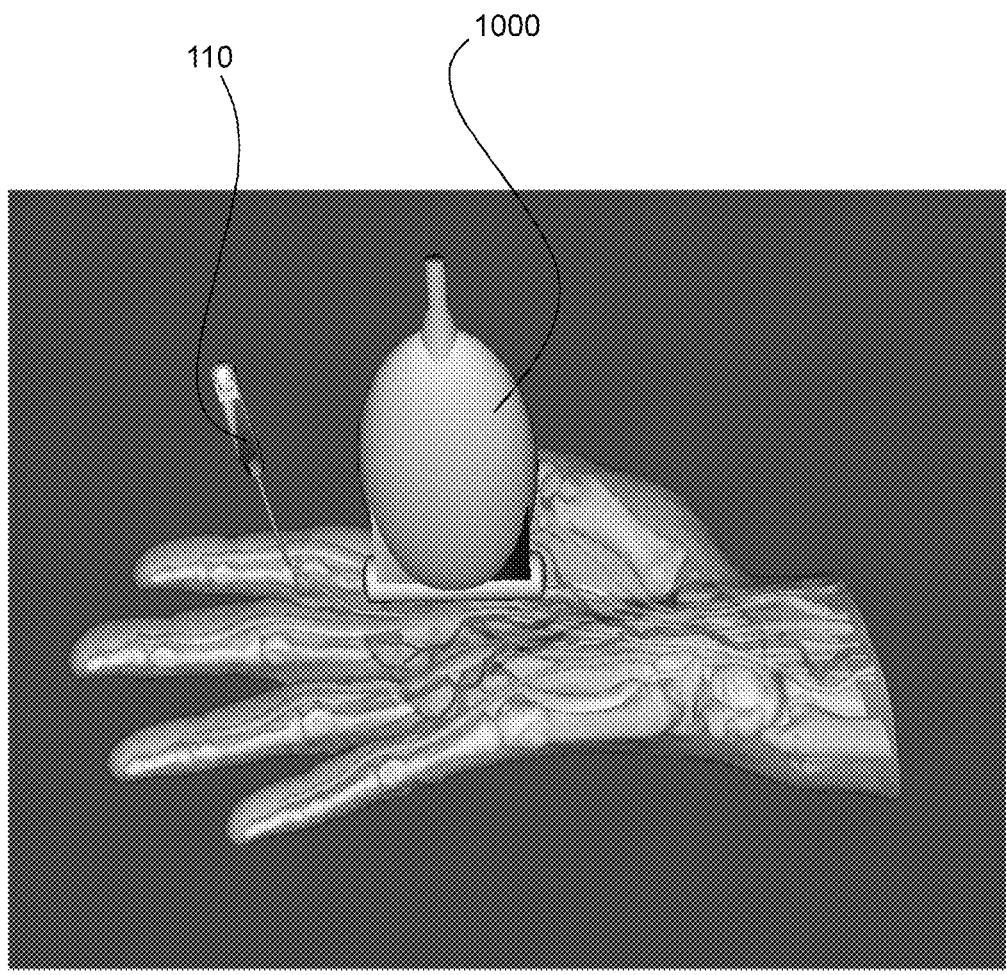
FIGS. 49A and 49B are schematic illustrations showing the medical instrument of FIGS. 39 to 43A-C during section of the A1 pulley.
Figure 49B:
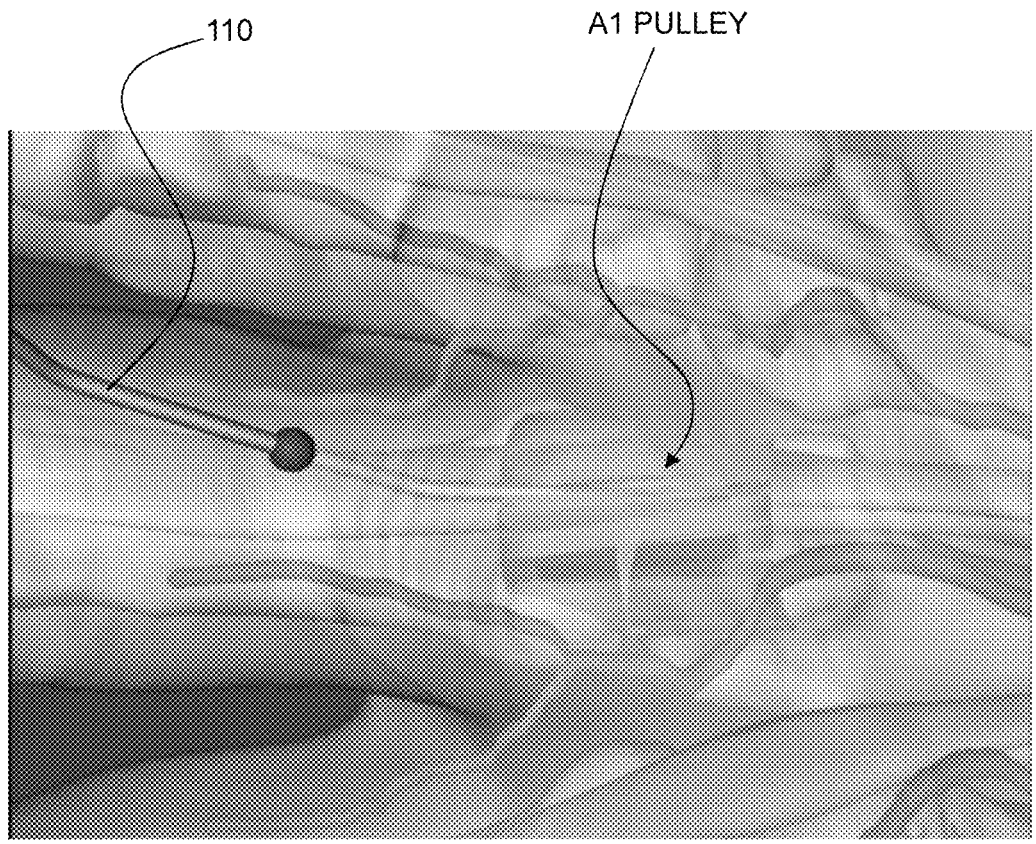

Each millimetre, the tip of leading edge 160A is introduced between the tendon and the pulley and the section is carried out by a crocheting movement. The A1 pulley is progressively cut in a retrograde manner by handling of the instrument 110 to induce an oscillating motion to its leading edge 160A from the dorsal to volar part of the A1 pulley, as schematically illustrated by FIGS. 49A and 49B. The release is performed in the safe zone level that is located at the apex of the pulley in the coronal plane. All over the procedure, short axial views are regularly performed to control the position of the instrument 110. At the end of the procedure, the tip of the instrument 110 is used as a hook to make sure that the entire A1 pulley has been fully released.

6. Confirmation That the Release is Complete

Figure 50:
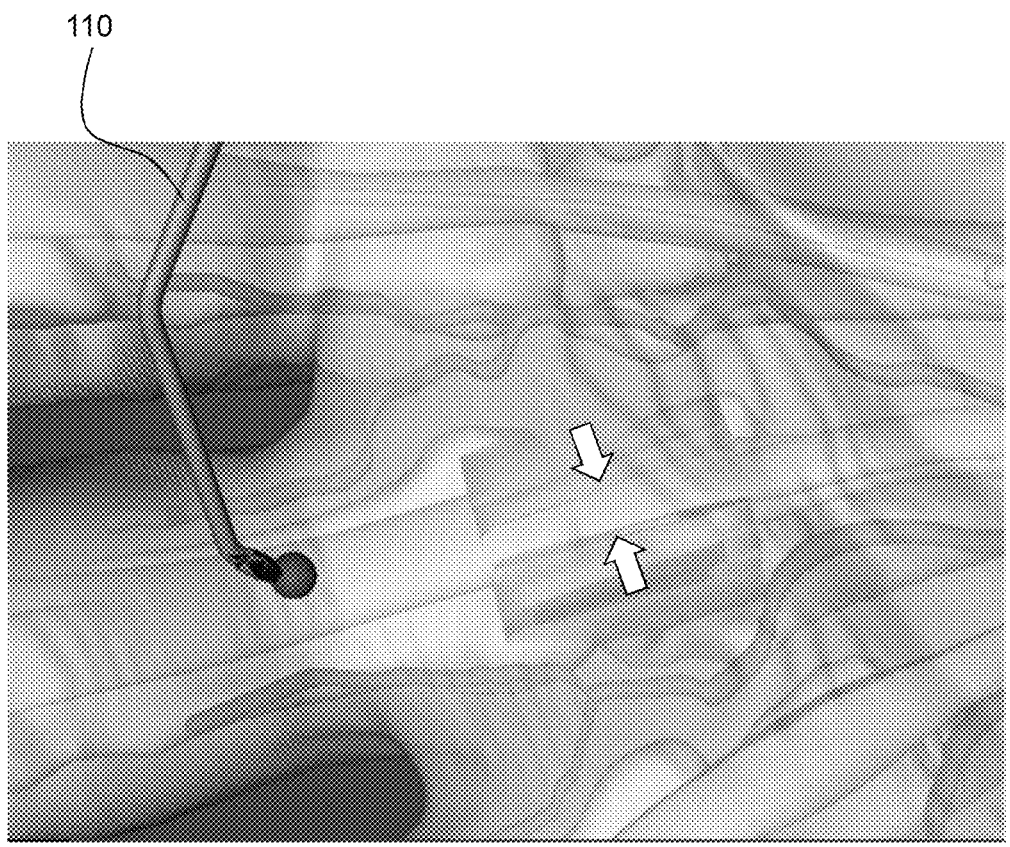
FIG. 50 is a schematic illustration showing withdrawal of the instrument of FIGS. 39 to 43A-C following completion of the release of the A1 pulley.

The instrument 110 is withdrawn and the patient is asked to fully flex the finger to make sure that the triggering has disappeared. FIG. 50 schematically illustrates withdrawal of the instrument 110 following completion of the release of the A1 pulley.

7. Postoperative Care

A compressive dressing is made, to be entirely removed, twelve hours after the procedure. No more dressing is then needed. The patient is allowed to do all his/her daily activities without any limitation, the day after the procedure. Passive proximal interphalangeal (PIP) hyperextension motion exercises are advised to prevent PIP postoperative flessum.

Surgical release procedures are very similar for the treatment of conditions commonly affecting upper limb extremities, like de Quervain tendinopathy (including section of the intracompartmental septum) and tennis elbow (lateral epicondylalgy).

Various modifications and/or improvements may be made to the above-described embodiments without departing from the scope of the invention as defined by the annexed claims. In particular, while embodiments of the invention have been described for the purpose of carrying out percutaneous carpal tunnel release and percutaneous A1 pulley release, the invention is generally applicable to any percutaneous release procedure, be it on upper or lower limbs, or other parts of the body, such as the neck or spine.

Furthermore, while the embodiments of FIGS. 1 to 31 show medical instruments where the bevelled end exhibits one or more strictly planar bevelled surfaces, the claims shall be construed as encompassing all variants where each bevelled surface is substantially planar or exhibits a slight curvature, be it slightly concave or convex. By way of convention, the plane of the bevelled surface can generally be defined as a plane that best approximates the bevelled surface.

The medical instrument of the invention could be specifically designed for single use. In that respect, and in order to prevent reuse of the medical instrument, the handle portion could be specifically designed to melt in case of resterilization, for instance by using a thermoplastic material.

LIST OF REFERENCE NUMERALS AND SIGNS USED THEREIN 1 medical instrument according to the invention (first embodiment)
2 handle portion of medical instrument 1, resp. 1*
2A inner face of handle portion 2
2B mounting hole provided on handle portion 2 for securing the elongated rod member 5, resp. 5* (e.g. by mechanical press-in insertion and/or gluing)
3 marking (e.g. laser marking) on inner face 2A of handle portion 2
5 elongated rod member of medical instrument 1 extending within defined plane P0
5a (single) curved section of elongated rod member 5
5A terminal end of (second portion of) elongated rod member 5

6 bevelled end, at terminal end 5A of elongated rod member 5, designed to act as a cutting device to sever tissue
6A bevelled surface of bevelled end 6
7 markings (e.g. embossings) provided along elongated rod member 5 designed to be distinguishable under sonography
1* medical instrument according to the invention (variant of first embodiment)
5* elongated rod member of medical instrument 1* extending within defined plane P0
5a* (single) curved section of elongated rod member 5*
5A* terminal end of (second portion of) elongated rod member 5*
6* bevelled end, at terminal end 5A* of elongated rod member 5*, designed to act as a cutting device to sever tissue
6A* bevelled surface of bevelled end 6*
7* markings (e.g. embossings) provided along elongated rod member 5* designed to be distinguishable under sonography
100 medical instrument according to the invention (embodiment with flattened end section)
200 handle portion of medical instrument 100
200A inner face of handle portion 2
300 marking (e.g. laser marking) on inner face 200A of handle portion 200
105 elongated rod member of medical instrument 100 extending within defined plane P0
105.1 hollow tube member
105.1A terminal end of hollow tube member 105.1 prior to flattening
105.2 inner member inserted inside a portion of hollow tube member 105.1
105a (single) curved section of elongated rod member 105
105A terminal end of (second portion of) elongated rod member 105
106 flattened section of free end of elongated rod member 105, at terminal end 105A of elongated rod member 105, designed to act as a cutting device to sever tissue
106A tapered leading edge of flattened section 106 (cutting edge)
700 markings (e.g. embossings) provided along elongated rod member 105 designed to be distinguishable under sonography
D1 diameter of elongated rod member 5, resp. 5*, upstream of terminal end 5A, resp. 5A* (of the order of e.g. 1.5 mm)
L0 length of handle portion 2 along the y axis
L1 overall length of elongated rod member 5 along the y axis
L2 length of end section at terminal end 5A of elongated rod member 5 along the z axis
D1* outer diameter of elongated rod member 105 upstream of terminal end 105A (of the order of e.g. 1.5 mm)
La* overall length of hollow tube member 105.1 prior to shaping
Lb* length of end section at terminal end 105.1A of hollow tube member 105.1 along the z axis prior to flattening
R1 radius of curvature of curved section 5a, 5a*, resp. 105a
a1 general direction of extension of first portion of elongated rod member 5, 5*, resp. 105 ("first direction")
a2 general direction of extension of end section at terminal end 5A, 5A*, resp. 105A of elongated member 5, 5*, resp. 105 ("second direction")
α1 angle of curved section 5a, 5a*, resp. 105a
α2 total angle of curvature of elongated rod member 5, 5*, resp. 105/angle formed between first and second directions a1 and a2 (e.g. ~90°)
θ1 angle of bevelled surface 6A with respect to defined plane P0
θ1* angle of bevelled surface 6A* with respect to defined plane P0
δ1 angle of surface at terminal end 105.1A of hollow tube member 105.1 prior to shaping and flattening
w1 width of flattened section 106 as measured in plane P0 (less than 2.5 mm, e.g. 2.3 mm)
t1 thickness of flattened section 106 as measured perpendicularly to plane P0 (less than 0.5 mm, e.g. 0.3 mm)
medical instrument according to the invention (second embodiment)
20 handle portion of medical instrument 10, resp. 10*
20A inner face of handle portion 20
20B mounting hole provided on handle portion 20 for securing the elongated rod member 50, resp. 50* (e.g. by mechanical press-in insertion and/or gluing)
50 elongated rod member of medical instrument 10 extending within defined plane P0
50a (first) curved section of elongated rod member 50
50b (second) curved section of elongated rod member 50
50c (third) curved section of elongated rod member 50
50A terminal end of (second portion of) elongated rod member 50
60 bevelled end, at terminal end 50A of elongated rod member 50, designed to act as a cutting device to sever tissue
60A bevelled surface of bevelled end 60
70 markings (e.g. embossings) provided along elongated rod member 50 designed to be distinguishable under sonography
10* medical instrument according to the invention (variant of second embodiment)
50* elongated rod member of medical instrument 10* extending within defined plane P0
50a* (first) curved section of elongated rod member 50*
50b* (second) curved section of elongated rod member 50*
50c* (third) curved section of elongated rod member 50*
50A* terminal end of (second portion of) elongated rod member 50*
60* bevelled end, at terminal end 50A* of elongated rod member 50*, designed to act as a cutting device to sever tissue
60A* bevelled surface of bevelled end 60*
70* markings (e.g. embossings) provided along elongated rod member 50* designed to be distinguishable under sonography
110 medical instrument according to the invention (further embodiment with flattened end section)
200* handle portion of medical instrument 110
200A* inner face of handle portion 200*
150 elongated rod member of medical instrument 110 extending within defined plane P0
150.1 hollow tube member
150.1A terminal end of hollow tube member 150.1 prior to flattening
150.2A (first) side bevel provided on leading edge of terminal end 150.1A of hollow tube member 150.1 prior to flattening 150.2B (second) side bevel provided on leading edge of terminal end 150.1A of hollow tube member 150.1 prior to flattening
150a (first) curved section of elongated rod member 150
150b (second) curved section of elongated rod member 150
150c (third) curved section of elongated rod member 150
150A terminal end of (second portion of) elongated rod member 150
160 flattened section of free end of elongated rod member 150, at terminal end 150A of elongated rod member 150, designed to act as a cutting device to sever tissue
160A tapered leading edge of flattened section 160 (cutting edge)
700* markings (e.g. embossings) provided along elongated rod member 150 designed to be distinguishable under sonography
D1' diameter of elongated rod member 50, resp. 50*, upstream of terminal end 50A, resp. 50A* (of the order of e.g. 1.3 mm)
L0' length of handle portion 20 along the y axis
L1' length of first portion of elongated rod member 50, resp. 50* along the y axis
L2' length of rectilinear section between first and second curved sections 50a, 50b, resp. 50a*, 50b*
L3' length of rectilinear section between second and third curved sections 50b, 50c, resp. 50b*, 50c*
L4' length of end section at terminal end 50A, resp. 50A* of elongated rod member 50, resp. 50*
D1** outer diameter of elongated rod member 150 upstream of terminal end 150A (of the order of e.g. 1.3 mm)
D2** inner diameter of elongated rod member 150 upstream of terminal end 150A (of the order of e.g. 0.9 mm)
La** overall length of hollow tube member 150.1 prior to shaping
L1** length of first portion of elongated rod member 150 along the y axis
L2** length of rectilinear section between first and second curved sections 150a, 150b
L3** length of rectilinear section between second and third curved sections 150b, 150c
L4** length of end section at terminal end 150A of elongated rod member 150
a1' general direction of extension of first portion of elongated rod member 50, 50*, resp. 150 ("first direction")
a2' general direction of extension of end section at terminal end 50A, 50A*, resp. 150A of elongated member 50, 50*, resp. 150 ("second direction")
β1 angle of first curved section 50a, 50a*, resp. 150a
β2 angle of second curved section 50b, 50b*, resp. 150b
β3 angle of third curved section 50c, 50c*, resp. 150c
β4 total angle of curvature of elongated rod member 50, 50*, resp. 150/angle formed between first and second directions a1' and a2' (e.g.) ~105°
θ2 angle of bevelled surface 60A with respect to defined plane P0
θ2* angle of bevelled surface 60A* with respect to defined plane P0
δ1' angle of surface at terminal end 150.1A of hollow tube member 150.1 prior to shaping and flattening
δ2' angle formed by side bevels 150.2A, 150.2B
w2 width of flattened section 160 as measured in plane P0 (less than 2.5 mm, e.g. 1.8 mm)
t2 thickness of flattened section 160 as measured perpendicularly to plane P0 (less than 0.5 mm, e.g. 0.4 mm)
500 elongated rod member of medical instrument extending within defined plane P0
500A terminal end of (second portion of) elongated rod member 500
600 bevelled end, at terminal end 500A of elongated rod member 500, designed to act as a cutting device to sever tissue
600A (first) bevelled surface of bevelled end 600
610A (second) bevelled surface of bevelled end 600
615A (first) side bevel provided on leading edge of bevelled end 600 and defining a corresponding (first) cutting edge 620A
615B (second) side bevel provided on leading edge of bevelled end 600 and defining a corresponding (second) cutting edge 620B
620A (first) cutting edge at leading edge of bevelled end 600
620B (second) cutting edge at leading edge of bevelled end 600
γ1 angle formed by side bevels 615A, 615B
θ3 angle of bevelled surface 600A with respect to defined plane P0
θ4 angle of bevelled surface 610A with respect to defined plane P0
615A* (first) side bevel provided on leading edge of bevelled end 6* and defining a corresponding (first) cutting edge 620A*
615B* (second) side bevel provided on leading edge of bevelled end 6* and defining a corresponding (second) cutting edge 620B*
620A* (first) cutting edge at leading edge of bevelled end 6*
620B* (second) cutting edge at leading edge of bevelled end 6*
γ1* angle formed by side bevels 615A*, 615B*
615A** (first) side bevel provided on leading edge of bevelled end 60* and defining a corresponding (first) cutting edge 620A**
615B** (second) side bevel provided on leading edge of bevelled end 60* and defining a corresponding (second) cutting edge 620B**
620A** (first) cutting edge at leading edge of bevelled end 60*
620B** (second) cutting edge at leading edge of bevelled end 60*
γ2* angle formed by cutting edges 620A, 620B
1000 sonography probe
x, y, z Cartesian coordinate system
GX generatrix along which the elongated rod member 5, 50, 5*, 50*, 500, 105, resp. 150, extends
P0 defined plane in which the elongated rod member 5, 50, 5*, 50*, 500, 105, resp. 150, extends
P plane of bevelled surface 6A
P' plane of bevelled surface 60A
P'', P''' plane of bevelled surface 600A, resp. 610A
P* plane of bevelled surface 6A*
P** plane of bevelled surface 60A*

The invention claimed is:

1. A method of performing a percutaneous release procedure on a human body using a medical instrument comprising a handle portion designed to allow handling, orientation and manipulation of the medical instrument by a surgeon, and an elongated rod member secured to the handle portion and extending substantially within a defined plane, wherein a first portion of the elongated rod member extends substantially along a first direction within the defined plane away from the handle portion, wherein a second portion of the elongated rod member, downstream of the first portion, is curved within the defined plane, wherein a free end of the elongated rod member, at a terminal end of the second portion, is shaped as a beveled end exhibiting at least a first beveled surface, wherein the beveled end is designed to act as a cutting device to sever tissue, said at least a first beveled surface being inclined with respect to the defined plane, and wherein an end section of the elongated rod member, at the terminal end of the second portion, extends substantially perpendicularly to the first direction, the method comprising:

percutaneously inserting the free end of the elongated rod member through an entry point and introducing the free end of the elongated rod member through surrounding tissue to an area of the human body to be treated; and manipulating the medical instrument to cause the beveled end, acting as the cutting device, to sever tissue in the area to be treated, wherein manipulating the medical instrument includes using the second portion of the elongated rod member as a fulcrum to perform crocheting movements inducing an oscillating motion to a leading edge of the beveled end.

2. The method according to claim 1, wherein an angle of inclination of a plane comprising the at least a first beveled surface with respect to the defined plane is of the order of 10° to 40°.

3. The method according to claim 2, wherein the angle of inclination is of the order of 15° to 30°.

4. The method according to claim 1, wherein the beveled end further exhibits at least a second beveled surface, the at least a first beveled surface and the at least a second beveled surface having distinct angles of inclination.

5. The method according to claim 1, wherein the leading edge of the beveled end, at a distal extremity of the beveled end, is provided with at least one side bevel defining a cutting edge.

6. The method according to claim 1, wherein the elongated rod member is solid and non-hollow.

7. The method according to claim 1, wherein the elongated rod member extends along a generatrix and wherein a lateral breadth of the elongated rod member as measured at any point along the generatrix, up to and including the terminal end of the second portion, does not exceed 2 mm (0.079 inches).

8. The method according to claim 1, wherein the end section of the elongated rod member extends along a second direction that forms an angle with respect to the first direction that is comprised between 80° and 120°.

9. The method according to claim 1, wherein the first portion of the elongated rod member is a substantially rectilinear section.

10. The method according to claim 9, wherein the first portion of the elongated rod member has a length of the order of 30 to 60 mm (1.181 to 2.362 inches).

11. The method according to claim 1, wherein the second portion is curved to include at least one curved section extending over an angle that exceeds 30°.

12. The method according to claim 11, wherein the at least one curved section includes a single curved section extending over an angle that exceeds 60°.

13. The method according to claim 12, wherein a radius of curvature of the single curved section is of the order of 30 to 45 mm (1.181 to 1.772 inches).

14. The method according to claim 11, wherein the at least one curved section includes multiple curved sections each extending over an angle that does not exceed 40°.

15. The method according to claim 14, wherein the multiple curved sections include three curved sections.

16. The method according to claim 14, wherein the multiple curved sections are separated by substantially rectilinear sections.

17. The method according to claim 16, wherein the substantially rectilinear sections separating the multiple curved sections each have a length of the order of 15 to 25 mm (0.591 to 0.984 inches).

18. The method according to claim 1, wherein the elongated rod member is provided with a plurality of markings designed to be distinguishable under sonography.

19. The method according to claim 18, wherein the plurality of markings are embossings.

20. The method according to claim 18, wherein the plurality of markings are distributed over the second portion of the elongated rod member.

21. The method according to claim 18, wherein dimensions and/or distribution of the plurality of markings along the elongated rod member are/is non-uniform.

22. The method according to claim 1, wherein the handle portion is provided with a visible marking.

23. The method according to claim 22, wherein the visible marking is a laser marking.

24. The method according to claim 22, wherein the visible marking is provided on an inner face of the handle portion which is oriented in a same direction as the second portion of the elongated rod member.

25. The method according to claim 1, wherein a cross-sectional area of the elongated rod member does not exceed 5 mm$^2$ (0.0078 square inches).

26. The method according to claim 25, wherein the cross-sectional area of the elongated rod member does not exceed 2 mm$^2$ (0.0031 square inches).

27. The method according to claim 1, wherein a diameter of the elongated rod member, upstream of the terminal end, is of the order of 1 to 2 mm (0.039 to 0.079 inches).

28. The medical instrument method according to claim 1, wherein the elongated rod member has a substantially circular cross-section upstream of the terminal end.

29. The method according to claim 1, wherein the percutaneous release procedure is performed on upper or lower limbs of the human body.

30. The method according to claim 29, wherein the percutaneous release procedure is a percutaneous carpal tunnel release procedure or a percutaneous A1 pulley release procedure.

31. The method according to claim 1, comprising performing the percutaneous release procedure under sonographic assistance.

32. The method according to claim 31, further comprising the step of manipulating a sonography probe in combination with the medical instrument.

33. The method according to claim 31, wherein the elongated rod member is provided with a plurality of markings that are distinguishable under sonography, and wherein the method comprises exploiting the plurality of markings to monitor a position and an orientation of the medical instrument.

34. The method according to claim 33, comprising automatically locating and detecting the orientation of the medical instrument in sonographic imagery.

35. The method according to claim 34, comprising superimposing a virtual representation of the medical instrument in real time on the sonographic imagery.

* * * * *